(12) United States Patent
Ng et al.

(10) Patent No.: US 10,233,179 B2
(45) Date of Patent: Mar. 19, 2019

(54) THIAZOLES AND USES THEREOF

(71) Applicant: AbbVie Inc., North Chicago, IL (US)

(72) Inventors: Iok Chan Ng, Arlington Heights, IL (US); M-akhteruzzaman Molla, Gurnee, IL (US); Tami J. Pilot-Matias, Green Oaks, IL (US); Anil Vasudevan, Union Grove, WI (US); Tatyana Dekhtyar, Libertyville, IL (US); Artour Gomtsian, Vernon Hills, IL (US); Kathy Sarris, Mundelein, IL (US); Ana Aguirre, Chicago, IL (US); Mikhail Chafeev, Khimki (RU)

(73) Assignee: Abbvie Inc., North Chicago, IL (US)

( * ) Notice: Subject to any disclaimer, the term of this patent is extended or adjusted under 35 U.S.C. 154(b) by 0 days.

(21) Appl. No.: 14/786,454

(22) PCT Filed: Apr. 22, 2014

(86) PCT No.: PCT/US2014/035014
§ 371 (c)(1),
(2) Date: Oct. 22, 2015

(87) PCT Pub. No.: WO2014/176268
PCT Pub. Date: Oct. 30, 2014

(65) Prior Publication Data
US 2016/0068521 A1    Mar. 10, 2016

Related U.S. Application Data

(60) Provisional application No. 61/814,523, filed on Apr. 22, 2013.

(51) Int. Cl.
| | | |
|---|---|---|
| C07D 417/14 | (2006.01) | |
| C07D 403/14 | (2006.01) | |
| A61K 45/06 | (2006.01) | |
| A61K 31/4178 | (2006.01) | |
| A61K 31/427 | (2006.01) | |
| A61K 31/433 | (2006.01) | |
| A61K 31/4439 | (2006.01) | |
| A61K 31/501 | (2006.01) | |
| A61K 31/506 | (2006.01) | |

(52) U.S. Cl.
CPC ........ *C07D 417/14* (2013.01); *A61K 31/4178* (2013.01); *A61K 31/427* (2013.01); *A61K 31/433* (2013.01); *A61K 31/4439* (2013.01); *A61K 31/501* (2013.01); *A61K 31/506* (2013.01); *A61K 45/06* (2013.01); *C07D 403/14* (2013.01)

(58) Field of Classification Search
CPC ............................ C07D 403/14; C07D 417/14
See application file for complete search history.

(56) References Cited

U.S. PATENT DOCUMENTS

| | | | |
|---|---|---|---|
| 6,723,743 B1 | 4/2004 | Thurkauf et al. | |
| 7,279,497 B2 | 10/2007 | Yi et al. | |
| 2002/0099208 A1 | 7/2002 | Yu et al. | |
| 2006/0148798 A1 | 7/2006 | Lundstedt et al. | |
| 2006/0178414 A1 | 8/2006 | Gao et al. | |
| 2007/0135403 A1 | 6/2007 | Merla et al. | |
| 2008/0255197 A1 | 10/2008 | Bridger et al. | |
| 2008/0261978 A1 | 10/2008 | Clark et al. | |
| 2008/0262042 A1 | 10/2008 | Kajino et al. | |
| 2008/0287414 A1 | 11/2008 | Bergman et al. | |
| 2009/0192182 A1 | 7/2009 | Kusumi et al. | |
| 2009/0227581 A1 | 9/2009 | Baxter et al. | |
| 2009/0306076 A1 | 12/2009 | Thompson et al. | |
| 2010/0178221 A1 | 7/2010 | Babich et al. | |
| 2011/0183988 A1 | 7/2011 | Ibrahim et al. | |
| 2011/0281837 A1 | 11/2011 | Hutchinson et al. | |
| 2013/0045964 A1 | 2/2013 | Cherney et al. | |

FOREIGN PATENT DOCUMENTS

| | | | | |
|---|---|---|---|---|
| EP | 1724263 A1 | 11/2006 | | |
| EP | 1948666 B1 | 3/2010 | | |
| EP | 2444402 A1 | 4/2012 | | |
| EP | 1961744 B1 | 4/2013 | | |
| WO | 0136395 A1 | 5/2001 | | |
| WO | WO 0249993 A2 * | 6/2002 | ............. | A61K 31/38 |
| WO | WO-2004062609 A2 | 7/2004 | | |
| WO | WO-2010056717 A1 | 5/2010 | | |
| WO | WO-2012150952 A1 | 11/2012 | | |

OTHER PUBLICATIONS

CAS Registry Entry for Registry No. 1244858-19-2, which entered STN on Oct. 3, 2010.*
CAS Registry Entry for Registry No. 853613-91-9, which entered STN on Jul. 1, 2005.*
Chiu et al. Inorg. Chem. 2003, 42, 5107-5116.*
CAS Registry Entry for Registry No. 958592-28-4, which entered STN on Dec. 18, 2007.*
CAS Registry Entry for Registry No. 1170481-87-4, which entered STN on Jul. 30, 2009.*
CAS Registry Entry for Registry No. 1244863-07-7, which entered STN on Oct. 3, 2010.*
Ansel C.H., et al., "Pharmaceutical Dosage Forms and Drug Delivery Systems", 7th Edition, Lippincott Williams & Wilkins, 1999, pp. 367-369.
Greene T.W., et al., "Protective Groups," in: Organic Synthesis, 3rd Edition, John Wiley and Sons, Inc., 1999.

(Continued)

*Primary Examiner* — Matthew P Coughlin

(57) ABSTRACT

This disclosure relates to: (a) compounds and salts thereof that, inter alia, inhibit RSV infection and/or replication; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

37 Claims, No Drawings

(56) References Cited

OTHER PUBLICATIONS

Hoover J.E., Remington's Pharmaceutical Sciences, 15th Edition, 1975, Mack Publishing Co.
International Search Report for Application No. PCT/US2014/035014, dated Sep. 8, 2014, 4 pages.
Kantam; MI, "An Efficient N-Arylation of Heterocycles with Aryl-, Heteroaryl- and Vinylboronic Acids Catalyzed by Copper Fluorapatite", 2010, 93, 974-979.
Written Opinion for PCT/US14/35014 dated Sep. 8, 2014, 15 pages.
Sun, Z. et al., "Respiratory Syncytial Virus Entry Inhibitors Targeting the F Protein", Viruses, 2013, vol. 5(1), pp. 211-225. DOI: 10.3390/v5010211.
Chapman, J. et al., "RSV604, a Novel Inhibitor of Respiratory Syncytial Virus Replication", Antimicrobial Agents and Chemotherapy, 2007, vol. 51(9), pp. 3346-3353.
Markland W. et al., "Broad-spectrum antiviral activity of the IMP dehydrogenase inhibitor VX-497: a comparison with ribavirin and demonstration of antiviral additivity with alpha interferon", Antimicrobial Agents and Chemotherapy, 2000, vol. 44(4), pp. 859-866.
Examination Report dated Jan. 26, 2018 for EP Application No. 14787393.9, 4 pages.
Higa, T. et al., "Synthesis and characterization of imidazolate-bridged polynuclear copper complexes," Inorganica Chimica Acta, 2007, vol. 360(10), pp. 3304-3313.
Scarpellini, M. et al., "Structural, spectroscopic and redox studies of a new ruthenium (III) complex with an imidazole-rich tripodal ligand," Inorganica Chimica Acta, 2004, vol. 357(3), pp. 707-715.

\* cited by examiner

THIAZOLES AND USES THEREOF

TECHNICAL FIELD

This disclosure is directed to: (a) compounds and salts thereof that, inter alia, are useful for inhibiting human respiratory syncytial virus (RSV) infection and/or replication; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

BACKGROUND

Human respiratory syncytial virus (RSV) is a pneumovirus in the Paramyxoviridae family. It is an enveloped, nonsegmented, negative-stranded RNA virus. Its 15.2 kb genome has been completely sequenced and it contains 10 mRNAs encoding 11 distinct proteins. RSV has three transmembrane surface proteins (F, G, SH) essential for attachment and entry, two nonstructural proteins (NS1, NS2), a matrix (M) protein, a nucleocapsid (N) protein that encapsidates the viral RNA genome, a phosphoprotein (P), and an RNA polymerase (L). In addition, the RSV M2 mRNA encodes both the M2-1 and M2-2 proteins.

RSV is the leading cause of serious lower respiratory tract infection in infants and young children. Most infected infants and children suffer only mild symptoms, but 25-40% of them develop lower respiratory signs indicative of a viral bronchiolitis or pneumonia. Severe lower respiratory tract RSV infection can lead to consequences of different severity, ranging from increased risk of developing childhood asthma to death. Following RSV infection, immunity is incomplete and re-infections can occur throughout life. It is estimated that RSV causes approximately 60 million infections and 160,000 deaths worldwide each year. RSV infection results in up to 125,000 hospitalizations of infants annually in the United States, which is equivalent to approximately 0.1-0.2% of hospital admission of infants from this age group. The infants most at risk of severe RSV disease are those born prematurely, and those with bronchopulmonary dysplasia, congenital heart disease, or immunodeficiency. Hospital admission rates with these conditions range between 5% and 30%. The mortality rate among children admitted to hospital is approximately 3% for those with heart and lung diseases and up to 1% for those without these risk factors. RSV infection is also a significant cause of morbidity in the elderly and immunocompromised populations. In the hospitalized elderly, mortality can be as high as 10-20%, and in the severely immunocompromised patients with RSV pneumonia, the rate is approximately 50%.

RSV epidemics occur every winter in temperate climates. There are two groups (also referred to as subgroups) of RSV, A and B. Both groups A and B may co-circulate within an epidemic, but their relative proportion may vary from year to year. The predominant epidemic group may also change in different years, with group A having a somewhat higher incidence of being the predominant group. The sequence homology between the two groups varies in the different viral proteins. For example, the F and N proteins are highly conserved with 91% and 96% amino acid identity between the two groups, respectively. The sequence of the G protein, on the other hand, is significantly different between the two groups, with the amino acid identity being only 53%. There is conflicting data regarding the virulence differences between the two groups of RSV. Some studies found no difference in the clinical severity of the illness caused by the two groups, while others reported that group A appeared to be associated with more severe disease.

At present, there is no clinically approved vaccine or effective antiviral therapy for the treatment of RSV. Attempts to develop a safe and efficacious RSV vaccine have failed thus far due to challenges associated with at-risk subjects (including infants, the elderly and the immunocompromised) who usually have low tolerance to the side effects of a vaccine and who tend to mount reduced immune responses due to their weaker immune systems.

Ribavirin has been used to treat RSV infection but requires a prolonged aerosol administration, and there are doubts as to its safety and its efficacy in the treatment of RSV infection. In addition, ribavirin is associated with undesirable side effects such as anemia, fatigue, irritability, skin rash, nasal stuffiness, sinusitis, cough and even birth defects.

Palivizumab/Synagis® is a humanized murine monoclonal antibody directed against the RSV F protein that has been used as passive immunoprophylaxis to prevent the spread of the virus to the lower respiratory tract. Although palivizumab has been used successfully to reduce the frequency of hospitalizations for RSV infection in high risk populations, the antibody has only been approved for prophylactic use in infants who are at risk of developing serious symptoms from RSV infection, such as those born prematurely, and/or with congenital heart or lung disease.

Therefore, there is a significant need for compounds for the prevention and treatment of RSV and for therapies that extend safe and effective treatment to at-risk adults and children with acute RSV infections.

SUMMARY

Disclosed herein is a compound of formula (A), and methods of making such a compound,

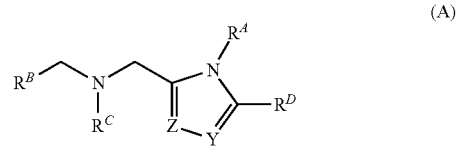

wherein, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl;

$R^B$ is selected from the group consisting of

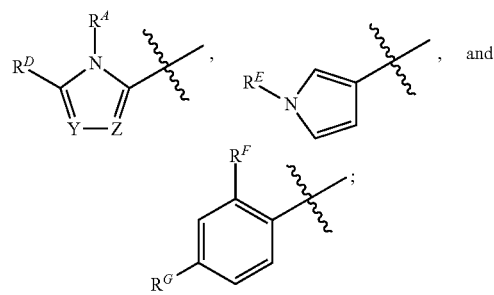

$R^C$ is selected from the group consisting of:

branched-$C_4$-$C_8$alkyl, branched-$C_3$-$C_8$haloalkyl and —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl;

$C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen;

phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl;

monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

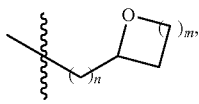

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3;

phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen;

5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and

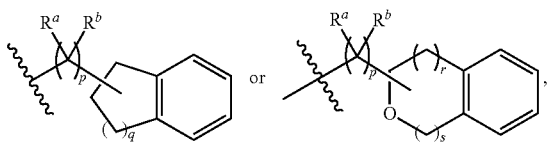

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2;

q is 1 or 2;

r is 1 or 2; and s is 0 or 1;

$R^D$ is hydrogen or phenyl;

$R^E$ is phenyl optionally substituted with 1 or 2 substituents selected from the group consisting of $C_1$-$C_6$alkyl, $C_1$-$C_6$haloalkyl and halogen;

$R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen;

$R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and Y and Z are each independently selected from the group consisting of CH or N;

wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

This disclosure also relates to pharmaceutical compositions comprising therapeutically effective amount of one or more compound(s) described herein or pharmaceutically acceptable salts, solvates, or salts of solvates thereof, in combination with one or more pharmaceutically acceptable carrier(s).

This disclosure also is directed to compositions (including pharmaceutical compositions) that comprise one or more of the disclosed compounds and/or salts, and, optionally, one or more additional therapeutic agents.

This disclosure also is directed to kits that comprise one or more of the disclosed compounds and/or salts, and, optionally, one or more additional therapeutic agents.

This disclosure also is directed to methods of use of the compounds, salts, compositions, and/or kits to, for example, inhibit replication of an RNA virus (including RSV).

This disclosure also is directed to compounds, salts, compositions, and/or kits for use in inhibiting replication of an RNA virus (including RSV).

This disclosure also is directed to compounds, salts, compositions, and/or kits for use in treating RSV infection.

This disclosure also is directed to a use of one or more of the disclosed compounds and/or salts to prepare a medicament. The medicament optionally can comprise one or more additional therapeutic agents. In some embodiments, the medicament is useful for treating RSV infection.

The compounds, compositions comprising the compounds, pharmaceutically acceptable salts, solvates, or salts of the solvates thereof, and methods for treating or preventing conditions and disorders by administering the compounds or compositions thereof, are further described herein. These and other objectives are described further in the following paragraphs. These objectives should not be deemed to narrow the scope of the disclosure.

DETAILED DESCRIPTION

This detailed description is intended only to acquaint others skilled in the art with the disclosed embodiments, their principles, and their practical application so that others skilled in the art may adapt and apply the embodiments in their numerous forms, as they may be best suited to the requirements of particular uses. This description and its specific examples are intended for purposes of illustration only. This disclosure, therefore, is not limited to the embodiments described in this patent application, and may be variously modified.

The present disclosure describes compounds of formula (A) and methods of preparing such compounds,

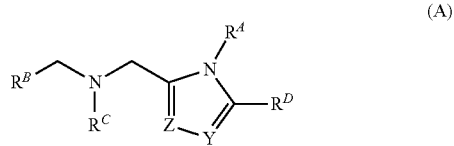

(A)

wherein $R^A$, $R^B$, $R^C$, $R^D$, Y and Z are as defined above in the Summary and below in the Detailed Description. Compositions comprising such compounds and methods for treating conditions and disorders using such compounds and compositions are also disclosed.

In various embodiments, compounds described herein may contain variables that occur more than one time in any substituent or in the compound described or any other formulae herein. Definition of a variable on each occurrence is independent of its definition at another occurrence. Further, combinations of variables are permissible only if such combinations result in stable compounds. Stable compounds are compounds that can be isolated from a reaction mixture.

Definitions

The term "alkenylene" denotes a divalent group derived from a straight or branched chain hydrocarbon of 2 to 4 carbon atoms and contains at least one carbon-carbon double. Representative examples of alkylene include, but are not limited to, —CH=CH— and —CH$_2$CH=CH—.

The term "alkoxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkoxyalkyl" means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkyl" means a straight or branched, saturated hydrocarbon chain. For example "C$_1$-C$_{10}$-alkyl" means a straight or branched chain, saturated hydrocarbon containing 1 to 10 carbon atoms. For example "C$_1$-C$_3$-alkyl" means a straight or branched chain, saturated hydrocarbon containing 1 to 3 carbon atoms. Examples of alkyl include, but are not limited to, methyl, ethyl, n-propyl, isopropyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched saturated hydrocarbon chain. Examples of alkylene include, but are not limited to, —CH$_2$—, —CH$_2$CH$_2$—, —CH$_2$CH$_2$CH$_2$—, —CH$_2$CH$_2$CH$_2$CH$_2$—, —CH(CH$_3$)—, and —CH$_2$CH(CH$_3$)CH$_2$—.

The term "aryl", means phenyl or a bicyclic aryl. For example, "C$_6$-C$_{10}$-aryl" refers to an aryl group that may have from six to ten carbon atoms. The bicyclic aryl is naphthyl, or a phenyl fused to a monocyclic cycloalkyl, or a phenyl fused to a monocyclic cycloalkenyl. Non-limiting examples of the aryl groups include dihydroindenyl, indenyl, naphthyl, dihydronaphthalenyl, and tetrahydronaphthalenyl. The aryl groups can be unsubstituted or substituted, and the bicyclic aryl is attached to the parent molecular moiety through any substitutable carbon atom contained within the bicyclic ring system.

The term "arylalkyl," refers to an aryl group attached to the parent molecular moiety through an alkyl group.

"Cyano" means a —CN group.

The term "cyanoalkyl" means a cyano group appended to the parent molecular moiety through an alkylene group. Representative examples of cyanoalkyl include, but are not limited to, cyanomethyl, 2-cyanoethyl, and 3-cyanopropyl.

The term "cycloalkyl" or "cycloalkane" means a monocyclic, a bicyclic, a tricyclic, or a spirocyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system. Spirocyclic cycloalkyl is exemplified by a monocyclic or a bicyclic cycloalkyl, wherein two of the substituents on the same carbon atom of the ring, together with said carbon atom, form a 3-, 4-, 5-, or 6-membered monocyclic cycloalkyl. An example of a spirocyclic cycloalkyl is spiro[2.5]octane. The spirocyclic cycloalkyl groups of the present invention can be appended to the parent molecular moiety through any substitutable carbon atom of the groups.

"Cycloalkylalkyl" refers to an alkyl moiety substituted with a cycloalkyl group, wherein cycloalkyl is as defined herein. Examples of cycloalkylalkyl groups include, but are not limited to, cyclopropylmethyl, cyclobutylmethyl, cyclopentylethyl and cyclohexylmethyl.

The term "cycloalkenyl" or "cycloalkene" means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group, or a bridged monocyclic ring system in which two non-adjacent carbon atoms of the monocyclic ring are linked by an alkylene bridge containing one, two, three, or four carbon atoms. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" means Cl, Br, I, or F.

The term "haloalkoxy" means a haloalkyl group appended to the parent molecule through an oxygen atom. Representative examples of haloalkoxy include, but are not limited to, trifluoromethoxy, difluoromethoxy, and 2,2,2-trifluoroethoxy.

The term "haloalkyl" means an alkyl group, as defined herein, in which one, two, three, four, five or six hydrogen atoms are replaced by halogen. The term "$C_1$-$C_{10}$-haloalkyl" means a $C_1$-$C_{10}$ alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, trifluorobutyl (such as, but not limited to, 4,4,4-trifluorobutyl), and trifluoropropyl (such as, but not limited thereto, 3,3,3-trifluoropropyl).

The term "heteroaryl" means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl (including, but not limited thereto, furan-2-yl), imidazolyl (including, but not limited thereto, 1H-imidazol-1-yl), isoxazolyl, isothiazolyl, oxadiazolyl, 1,3-oxazolyl, pyridinyl (e.g. pyridin-4-yl, pyridin-2-yl, pyridin-3-yl), pyridazinyl, pyrimidinyl, pyrazinyl, pyrazolyl, pyrrolyl, tetrazolyl, thiadiazolyl, 1,3-thiazolyl, thienyl (including, but not limited thereto, thien-2-yl, thien-3-yl), triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Non-limiting examples of bicyclic heteroaryl groups include benzofuranyl, benzothienyl, benzoxazolyl, benzimidazolyl, benzoxadiazolyl, 6,7-dihydro-1,3-benzothiazolyl, furo[3,2-c]pyridazinyl, furo[3,2-d]pyrimidinyl, furo[2,3-b]pyrazinyl, furo[2,3-c]pyridazinyl, furo[2,3-d]pyrimidinyl, furo[3,2-b]pyridinyl, furo[3,2-c]pyridinyl, furo[2,3-c]pyridinyl, furo[2,3-b]pyridine, imidazo[2,1-b]oxazolyl, imidazo[1,2-a]pyridinyl, imidazo[2,1-b][1,3,4]thiadiazolyl, imidazo[2,1-b][1,3,4]thiadiazolyl, imidazo[1,2-d][1,2,4]thiadiazolyl, imidazo[2,1-b]thiazolyl, indazolyl, indolizinyl, indolyl, isoindolyl, isoquinolinyl, naphthyridinyl, pyrazolo[1,5-a]pyridinyl, pyrazolo[1,5-c]pyrimidinyl, pyrazolo[1,5-a]pyrimidinyl, pyrazolo[5,1-c][1,2,4]triazinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any substitutable carbon atom or any substitutable nitrogen atom contained within the ring systems.

The term "heteroarylalkyl" means a heteroaryl, as defined herein, appended to the parent molecular moiety through an alkyl group, as defined herein.

The term "heterocycle", "heterocyclyl", or "heterocyclic" means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contain zero, one, two, or three double bonds and one, two, or three heteroatoms selected from the group consisting of O, N, and S. Non-limiting examples of monocyclic heterocycles include azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl (including, but not limited thereto, pyrrolidin-1-yl, pyrrolidin-2-yl, pyrrolidin-3-yl), tetrahydrofuranyl (including, but not limited thereto, tetrahydrofuran-3-yl), tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Non-limiting examples of bicyclic heterocycles include benzopyranyl, benzothiopyranyl, 2,3-dihydrobenzofuranyl, 2,3-dihydrobenzothienyl, benzo[d][1,3]dioxolyl, chromanyl and 2,3-dihydro-1H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle. The monocyclic and the bicyclic heterocycles may contain an alkenylene bridge of two, three, or four carbon atoms, or one or two alkylene bridges of 1, 2, 3, or 4 carbon atoms, or combinations thereof, wherein each bridge links two non-adjacent atoms of the ring system. Non-limiting examples of such bridged heterocycles include octahydro-2,5-epoxypentalene, azabicyclo[2.2.1]heptyl (including 2-azabicyclo[2.2.1]hept-2-yl), hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles can be unsubstituted or substituted, and are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quaternized. The term "N-heterocyclyl" refers to a nitrogen-containing heterocyclic group attached to the parent molecular moiety through a nitrogen atom.

"Phenylalkyl" refers to an alkyl moiety substituted with a phenyl group. Examples of phenylalkyl groups include, but are not limited to, phenylmethyl (i.e., benzyl), 1-phenylethyl, 2-phenylethyl, and phenylpropyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of a hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkoxyalkyl indicates that only the alkoxy component of the alkoxyalkyl substituent is substituted with one or more halogen radicals. If halogen substitution may alternatively or additionally occur on the alkyl component, the substituent would instead be described as "halogen-substituted alkoxyalkyl" rather than "haloalkoxyalkyl." And finally, if the halogen substitution may only occur on the alkyl component, the substituent would instead be described as "alkoxyhaloalkyl."

If substituents are described as being "independently selected" from a group, each substituent is selected independent of the other. Each substituent, therefore, may be identical to or different from the other substituent(s).

When words are used to describe a substituent, the rightmost-described component of the substituent is the component that has the free valence.

When a chemical formula is used to describe a substituent, the dash on the left side of the formula indicates the portion of the substituent that has the free valence.

When a chemical formula is used to describe a linking element between two other elements of a depicted chemical structure, the leftmost dash of the substituent indicates the portion of the substituent that is bound to the left element in the depicted structure. The rightmost dash, on the other hand, indicates the portion of the substituent that is bound to the right element in the depicted structure. To illustrate, if the depicted chemical structure is X-L-Y and L is described as —C(O)—N(H)—, then the chemical would be X—C(O)—N(H)—Y.

Compounds of formula (A) are as described herein.

Particular values of variable groups in compounds of formula (A) are as follows. Such values may be used where appropriate with any of the other values, definitions, claims or embodiments defined herein.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl.

In certain embodiments, $R^A$ is $C_1$-$C_6$alkyl.
In certain embodiments, $R^A$ is $C_1$-$C_6$alkoxyalkyl.
In certain embodiments, $R^A$ is cyano$C_1$-$C_6$alkyl.
In certain embodiments, $R^A$ is $C_1$-$C_6$haloalkyl.
In certain embodiments, $R^A$ is 1,3-thiazol-2-yl.
In certain embodiments, $R^A$ is 1,3,4-thiadiazol-2-yl.
In certain embodiments, $R^B$ is selected from the group consisting of

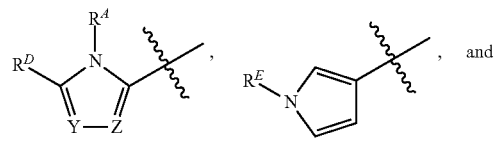

-continued

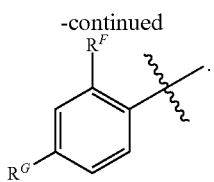

In certain embodiments, $R^B$ is

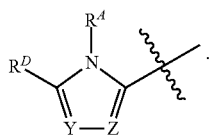

In certain embodiments, $R^B$ is

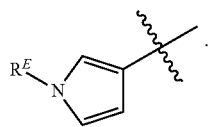

In certain embodiments, $R^B$ is

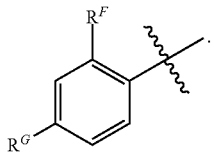

In certain embodiments, $R^C$ is selected from the group consisting of: branched-$C_4$-$C_8$alkyl, branched-$C_3$-$C_8$haloalkyl or —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl; $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen; phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl; monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

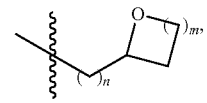

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3; phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and

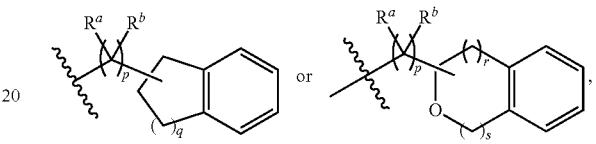

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; q is 1 or 2; r is 1 or 2; and s is 0 or 1.

In certain embodiments, $R^C$ is branched-$C_4$-$C_8$alkyl, branched-$C_3$-$C_8$haloalkyl or —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl.

In certain embodiments, $R^C$ is branched-$C_4$-$C_8$alkyl.

In certain embodiments, $R^C$ is branched-$C_3$-$C_8$haloalkyl.

In certain embodiments, $R^C$ is —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl.

In certain embodiments, $R^C$ is —C($R^{1a}R^{1b}$)—O—$C_1$-$C_6$alkyl, wherein $R^{1a}$ is hydrogen and $R^{1b}$ is $C_1$-$C_6$alkyl.

In certain embodiments, $R^C$ is —C($R^{1a}R^{1b}$)—O—$C_1$-$C_6$alkyl, wherein $R^{1a}$ is $C_1$-$C_6$alkyl and $R^{1b}$ is $C_1$-$C_6$alkyl.

In certain embodiments, $R^C$ is $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen.

In certain embodiments, $R^C$ is phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl.

In certain embodiments, $R^C$ is phenyl, wherein the phenyl is optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl.

In certain embodiments, $R^C$ is 5- or 6-membered heteroaryl, wherein the 5- or 6-membered heteroaryl is optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl.

In certain embodiments, $R^C$ is monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen.

In certain embodiments, $R^C$ is monocyclic $C_5$-$C_7$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl is optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen.

In certain embodiments, $R^C$ is bicyclic $C_6$-$C_{10}$cycloalkyl$C_1$-$C_3$alkyl, wherein the bicyclic $C_6$-$C_{10}$cycloalkyl of bicyclic $C_6$-$C_{10}$cycloalkyl$C_1$-$C_3$alkyl is optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen.

In certain embodiments, $R^C$ is

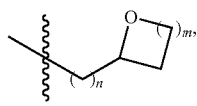

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3.

In certain embodiments, $R^C$ is phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen.

In certain embodiments, $R^C$ is 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen.

In certain embodiments, $R^C$ is

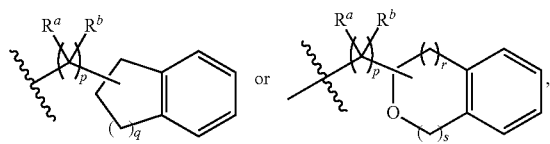

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; q is 1 or 2; r is 1 or 2; and s is 0 or 1.

In certain embodiments, $R^C$ is

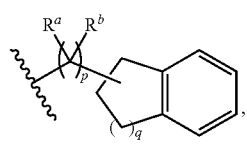

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; and q is 1 or 2.

In certain embodiments, $R^C$ is

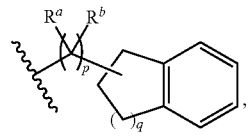

wherein $R^a$ and $R^b$ are at each occurrence independently selected from the group consisting of hydrogen and $C_1$-$C_6$alkyl, and wherein p is 0, 1 or 2; and q is 1 or 2.

In certain embodiments, $R^C$ is

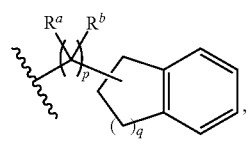

wherein $R^a$ and $R^b$ are taken together with the carbon atom to which they are attached to form a cyclopropyl, and wherein p is 0, 1 or 2; and q is 1 or 2.

In certain embodiments, $R^C$ is

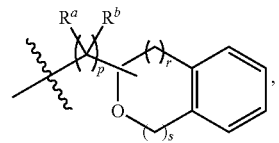

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; r is 1 or 2; and s is 0 or 1.

In certain embodiments, $R^C$ is

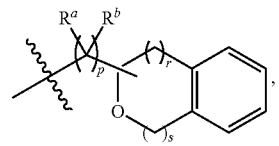

wherein $R^a$ and $R^b$ are at each occurrence independently selected from the group consisting of hydrogen and $C_1$-$C_6$alkyl, wherein p is 0, 1 or 2; r is 1 or 2; and s is 0 or 1.

In certain embodiments, $R^C$ is

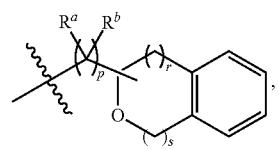

wherein $R^a$ and $R^b$ are taken together with the carbon atom to which they are attached to form a cyclopropyl, and wherein p is 0, 1 or 2; r is 1 or 2; and s is 0 or 1.

In certain embodiments, $R^D$ is hydrogen or phenyl.

In certain embodiments, $R^D$ is hydrogen.

In certain embodiments, $R^D$ is phenyl.

In certain embodiments, $R^E$ is phenyl optionally substituted with 1 or 2 substituents selected from the group consisting of $C_1$-$C_6$alkyl, $C_1$-$C_6$haloalkyl and halogen.

In certain embodiments, $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen.

In certain embodiments, $R^F$ is $C_1$-$C_6$alkyl.

In certain embodiments, $R^F$ is $C_1$-$C_6$alkoxy.

In certain embodiments, $R^F$ is halo$C_1$-$C_6$alkyl.

In certain embodiments, $R^F$ is halo$C_1$-$C_6$alkoxy.

In certain embodiments, $R^F$ is 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen.

In certain embodiments, $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen.

In certain embodiments, $R^G$ is hydrogen.

In certain embodiments, $R^G$ is $C_1$-$C_6$alkyl.

In certain embodiments, $R^G$ is $C_1$-$C_6$alkoxy.

In certain embodiments, $R^G$ is $C_1$-$C_6$haloalkyl.

In certain embodiments, $R^G$ is $C_1$-$C_6$haloalkoxy.

In certain embodiments, $R^G$ is halogen.

In certain embodiments, Y and Z are each independently selected from the group consisting of CH or N.

In certain embodiments, each Y and each Z is CH.

In certain embodiments, each Y and each Z is N.

In certain embodiments, at least one Y is N and at least one Z is CH.

In certain embodiments, at least one Y is CH and at least one Z is N.

In certain embodiments, each Y is N and each Z is CH.

In certain embodiments, each Y is CH and each Z is N.

In certain embodiments, the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl of $R^C$ is optionally substituted with a methyl or a cyclopropyl, wherein one atom of the cyclopropyl is an atom on the $C_1$-$C_3$alkyl chain.

In certain embodiments, the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl of $R^C$ is —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, —CH(CH$_3$)CH$_2$CH$_2$—, —CH$_2$CH(CH$_3$)CH$_2$—, or —CH$_2$CH$_2$CH(CH$_3$)—.

In certain embodiments, the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl of $R^C$ is

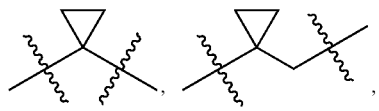

-continued

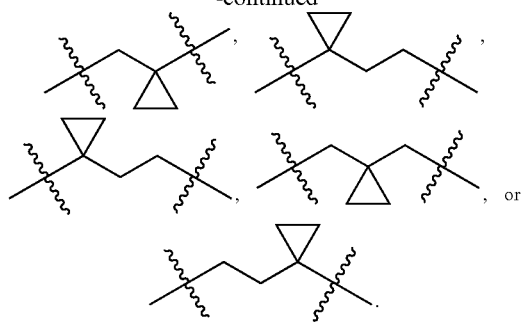

, or

In certain embodiments, $R^A$ is selected from the group consisting of 1,3-thiazol-2-yl and 1,3,4-thiadiazol-2-yl; $R^B$ is selected from the group consisting of

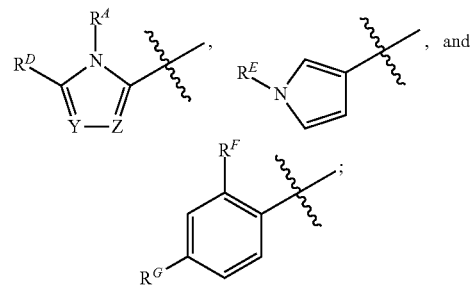

, and $R^C$ is selected from the group consisting of: branched-$C_4$-$C_8$alkyl, branched-$C_3$-$C_8$haloalkyl or —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl; $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen; phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl; monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

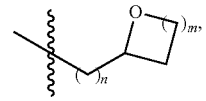

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3; phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and

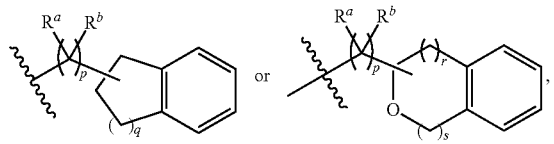

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; q is 1 or 2; r is 1 or 2; and s is 0 or 1; $R^D$ is hydrogen; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and each of Y and Z are CH; wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of 1,3-thiazol-2-yl and 1,3,4-thiadiazol-2-yl; $R^B$ is

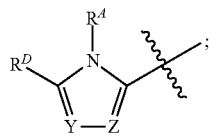

$R^C$ is selected from the group consisting of: branched-$C_4$-$C_8$alkyl, branched-$C_3$-$C_8$haloalkyl or —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl; $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen; phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl; monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

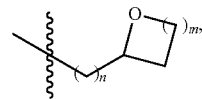

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3; phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and

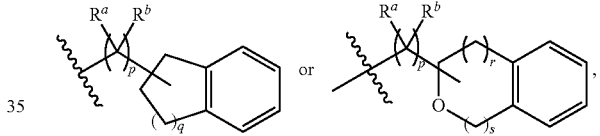

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; q is 1 or 2; r is 1 or 2; and s is 0 or 1; $R^D$ is hydrogen; and each of Y and Z are CH; wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of $C_1$-$C_6$alkyl, $C_1$-$C_6$alkoxyalkyl, cyano$C_1$-$C_6$alkyl and $C_1$-$C_6$haloalkyl; $R^B$ is selected from the group consisting of

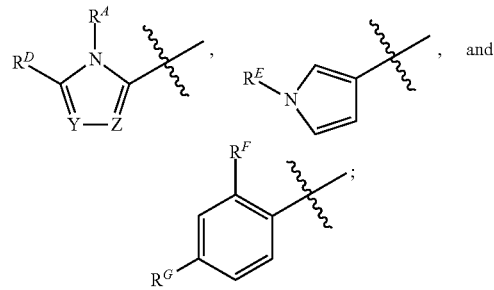

$R^C$ is selected from the group consisting of: branched-$C_4$-$C_8$alkyl, branched-$C_3$-$C_8$haloalkyl or —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl; $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen; phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl; monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

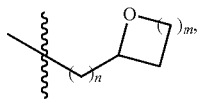

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3; phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and

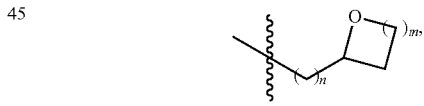

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; q is 1 or 2; r is 1 or 2; and s is 0 or 1; $R^D$ is phenyl; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; each Y is CH; and each Z is N; wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of $C_1$-$C_6$alkyl, $C_1$-$C_6$alkoxyalkyl, cyano$C_1$-$C_6$alkyl and $C_1$-$C_6$haloalkyl; $R^B$ is

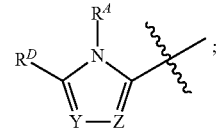

$R^C$ is selected from the group consisting of: branched-$C_4$-$C_8$alkyl, branched-$C_3$-$C_8$haloalkyl or —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl; $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen; phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl; monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

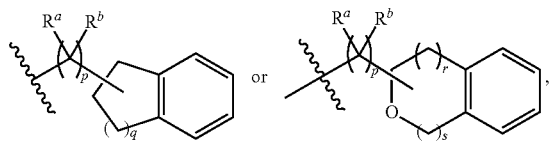

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3; phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and

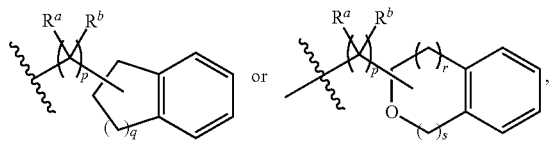

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; q is 1 or 2; r is 1 or 2; and s is 0 or 1; $R^D$ is phenyl; each Y is CH; and each Z is N; wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of 1,3-thiazol-2-yl and 1,3,4-thiadiazol-2-yl; $R^B$ is selected from the group consisting of

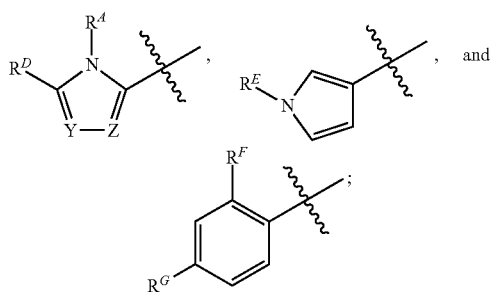

$R^C$ is selected from the group consisting of: branched-$C_4$-$C_8$alkyl, branched-$C_3$-$C_8$haloalkyl or —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl; $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen; phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl; monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

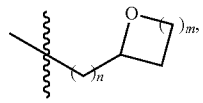

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3; phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and

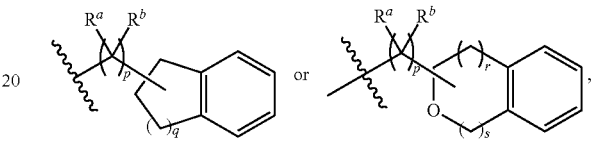

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; q is 1 or 2; r is 1 or 2; and s is 0 or 1; $R^D$ is hydrogen; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and each Y and each Z is CH; wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of $C_1$-$C_6$alkyl, $C_1$-$C_6$alkoxyalkyl, cyano$C_1$-$C_6$alkyl and $C_1$-$C_6$haloalkyl; $R^B$ is selected from the group consisting of

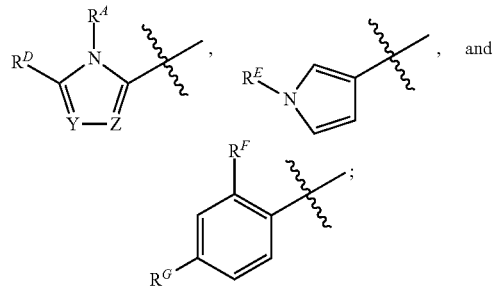

$R^C$ is selected from the group consisting of: branched-$C_4$-$C_8$alkyl, branched-$C_3$-$C_8$haloalkyl or —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl; $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen; phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl; monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

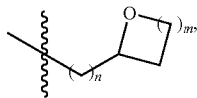

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3; phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and

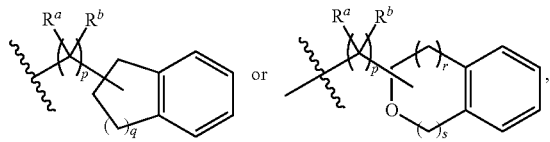

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; q is 1 or 2; r is 1 or 2; and s is 0 or 1; $R^D$ is phenyl; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; each Y is CH; and each Z is N; wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of $C_1$-$C_6$alkyl, $C_1$-$C_6$alkoxyalkyl, cyano$C_1$-$C_6$alkyl and $C_1$-$C_6$haloalkyl; $R^B$ is

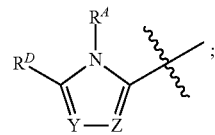

$R^C$ is selected from the group consisting of: branched-$C_4$-$C_8$alkyl, branched-$C_3$-$C_8$haloalkyl or —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl; $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen; phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl; monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

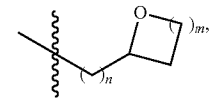

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3; phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and

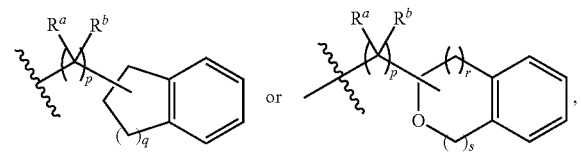

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; q is 1 or 2; r is 1 or 2; and s is 0 or 1; $R^D$ is phenyl; each Y is CH; and each Z is N; wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl; $R^B$ is selected from the group consisting of

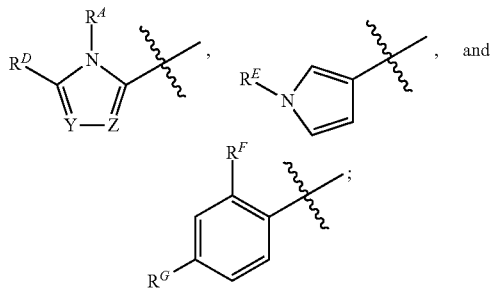

$R^C$ is selected from the group consisting of: branched-$C_4$-$C_8$alkyl, branched-$C_3$-$C_8$haloalkyl or —$C(R^{1a}R^{1b})$—O—$C_1$-$C_6$alkyl, wherein $R^{1a}$ is hydrogen or $C_1$-$C_6$alkyl, and $R^{1b}$ is $C_1$-$C_6$alkyl; $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen; phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl; monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

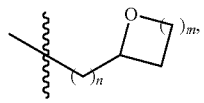

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3; phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; 5- or 6-membered heteroaryl$C_1$-$C_3$alkyl, wherein the 5- or 6-membered heteroaryl of 5- or 6-membered heteroaryl$C_1$-$C_3$alkyl is option-ally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and

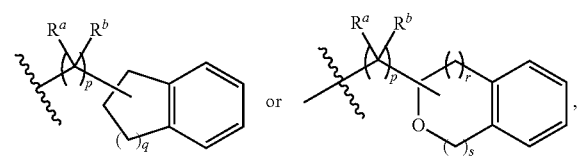

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; q is 1 or 2; r is 1 or 2; and s is 0 or 1; $R^D$ is hydrogen or phenyl; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; and halo$C_1$-$C_6$alkoxy; $R^G$ is hydrogen; and Y and Z are each independently selected from the group consisting of CH or N; wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl; $R^B$ is

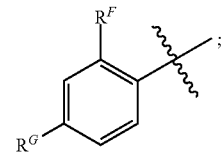

$R^C$ is selected from the group consisting of: branched-$C_4$-$C_8$alkyl, branched-$C_3$-$C_8$haloalkyl or —$C(R^{1a}R^{1b})$—O—$C_1$-$C_6$alkyl, wherein $R^{1a}$ is hydrogen or $C_1$-$C_6$alkyl, and $R^{1b}$ is $C_1$-$C_6$alkyl; $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen; phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl; monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

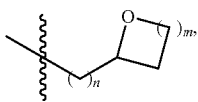

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3; phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and

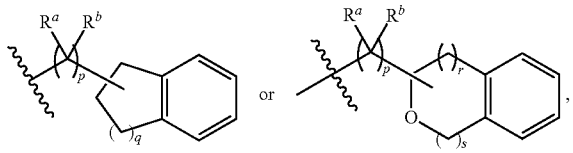

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; q is 1 or 2; r is 1 or 2; and s is 0 or 1; $R^D$ is hydrogen or phenyl; $R^F$ is selected from the group consisting of $C_1$-$C_6$alkyl; $C_1$-$C_6$alkoxy; halo$C_1$-$C_6$alkyl; and halo$C_1$-$C_6$alkoxy; $R^G$ is hydrogen; and Y and Z are each independently selected from the group consisting of CH or N; wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl; $R^B$ is selected from the group consisting of

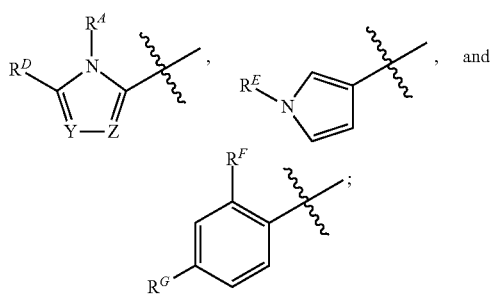

$R^C$ is selected from the group consisting of: branched-$C_4$-$C_8$alkyl, branched-$C_3$-$C_8$haloalkyl or —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl; $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen; phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl; monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3; phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and

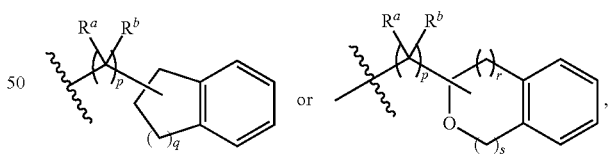

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; q is 1 or 2; r is 1 or 2; and s is 0 or 1; $R^D$ is hydrogen or phenyl; $R^E$ is phenyl optionally substituted with 1 or 2 substituents selected from the group consisting of $C_1$-$C_6$alkyl, $C_1$-$C_6$haloalkyl and halogen; $R^F$ is 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of $C_1$-$C_6$alkyl, $C_1$-$C_6$alkoxy, $C_1$-$C_6$haloalkyl, $C_1$-$C_6$haloalkoxy and halogen; and Y and Z are each independently selected from the group consisting of CH or N; wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl; $R^B$ is

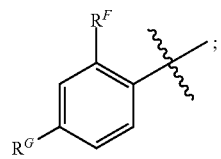

$R^C$ is selected from the group consisting of: branched-$C_4$-$C_8$alkyl, branched-$C_3$-$C_8$haloalkyl or —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl; $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen; phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl; monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

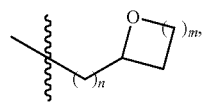

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3; phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and

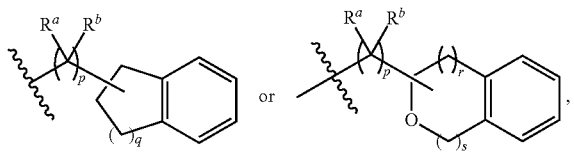

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; q is 1 or 2; r is 1 or 2; and s is 0 or 1; $R^D$ is hydrogen or phenyl; $R^F$ is 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of $C_1$-$C_6$alkyl, $C_1$-$C_6$alkoxy, $C_1$-$C_6$haloalkyl, $C_1$-$C_6$haloalkoxy and halogen; and Y and Z are each independently selected from the group consisting of CH or N; wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl; $R^B$ is selected from the group consisting of

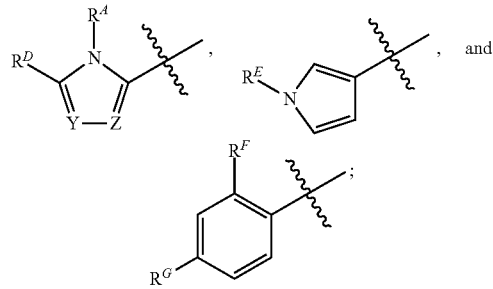

$R^C$ is selected from the group consisting of branched-$C_4$-$C_8$alkyl, branched-$C_3$-$C_8$haloalkyl, and —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl; $R^D$ is hydrogen or phenyl; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and Y and Z are each independently selected from the group consisting of CH or N.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl; $R^B$ is selected from the group consisting of

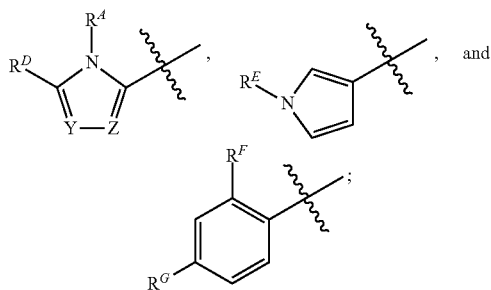

$R^C$ is $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen; $R^D$ is hydrogen or phenyl; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and Y and Z are each independently selected from the group consisting of CH or N.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl; $R^B$ is selected from the group consisting of

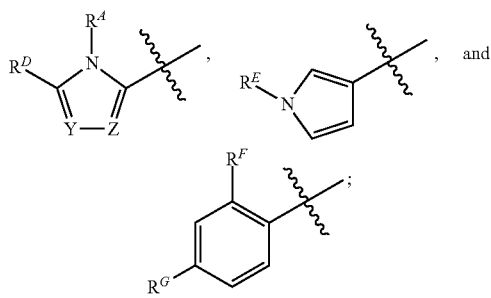

$R^C$ is selected from the group consisting of phenyl, 5- or 6-membered heteroaryl, wherein the phenyl or 5- or 6-membered heteroaryl is optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy and phenyl; $R^D$ is hydrogen or phenyl; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and Y and Z are each independently selected from the group consisting of CH or N.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl; $R^B$ is selected from the group consisting of

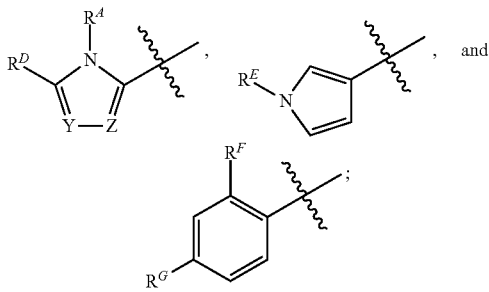

$R^C$ is selected from the group consisting of monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl is optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen; $R^D$ is hydrogen or phenyl; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and Y and Z are each independently selected from the group consisting of CH or N.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl; $R^B$ is selected from the group consisting of

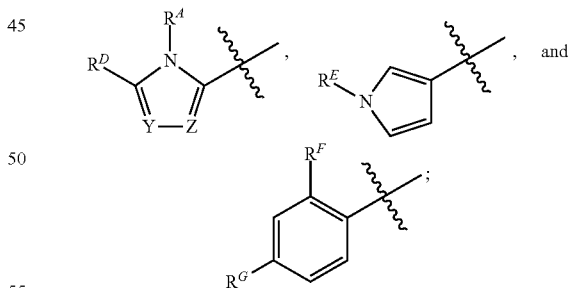

$R^C$ is selected from the group consisting of monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl is optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen; $R^D$ is hydrogen or phenyl; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and Y and Z are each independently selected from the group consisting of CH or N; wherein the $C_1$-$C_3$alkyl of monocyclic $C_5$-$C_7$cycloalkyl$C_1$-$C_3$alkyl or bicyclic $C_6$-$C_{10}$cycloalkyl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl; $R^B$ is selected from the group consisting of

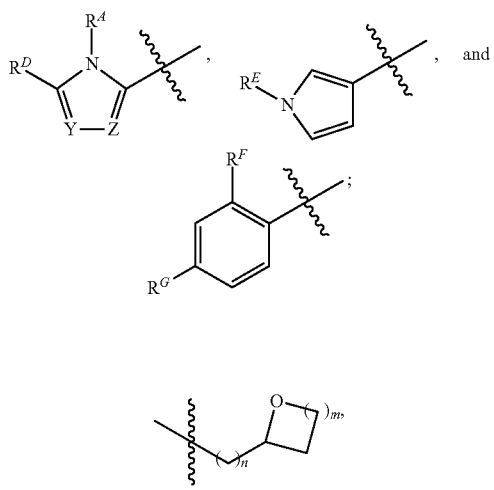

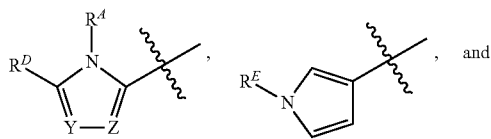

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy and halogen; wherein m is 1, 2 or 3; and n is 1, 2 or 3; $R^D$ is hydrogen or phenyl; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and Y and Z are each independently selected from the group consisting of CH or N.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl; $R^B$ is selected from the group consisting of

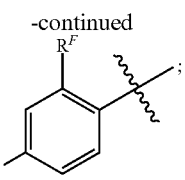

$R^C$ is phenyl$C_1$-$C_3$alkyl wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; $R^D$ is hydrogen or phenyl; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and Y and Z are each independently selected from the group consisting of CH or N.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl; $R^B$ is selected from the group consisting of

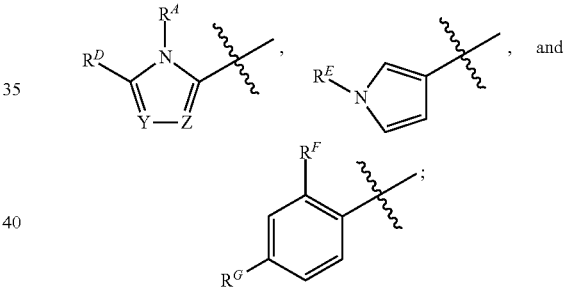

$R^C$ is phenyl$C_1$-$C_3$alkyl wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; $R^D$ is hydrogen or phenyl; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and Y and Z are each independently selected from the group consisting of CH or N; wherein the $C_1$-$C_3$alkyl of phenyl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl; $R^B$ is selected from the group consisting of

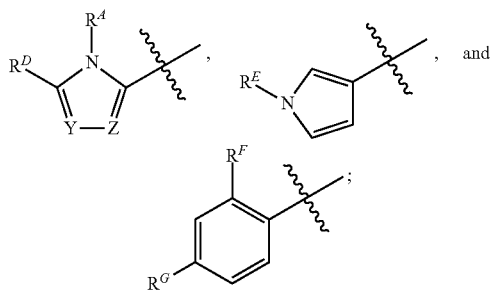

$R^C$ is selected from the group consisting of 5- or 6-membered heteroaryl$C_1$-$C_3$alkyl wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; $R^D$ is hydrogen or phenyl; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and Y and Z are each independently selected from the group consisting of CH or N.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl; $R^B$ is selected from the group consisting of

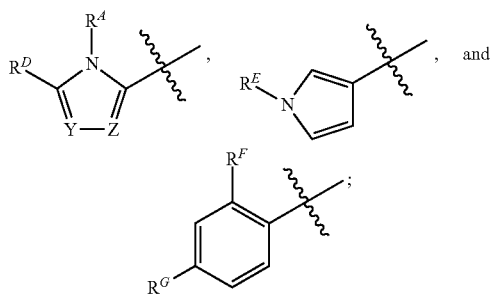

$R^C$ is selected from the group consisting of 5- or 6-membered heteroaryl$C_1$-$C_3$alkyl wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; $R^D$ is hydrogen or phenyl; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and Y and Z are each independently selected from the group consisting of CH or N; wherein the $C_1$-$C_3$alkyl of 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of $C_1$-$C_6$alkyl, $C_1$-$C_6$alkoxyalkyl, cyano$C_1$-$C_6$alkyl, $C_1$-$C_6$haloalkyl, 1,3-thiazol-2-yl and 1,3,4-thiadiazol-2-yl; $R^B$ is selected from the group consisting of

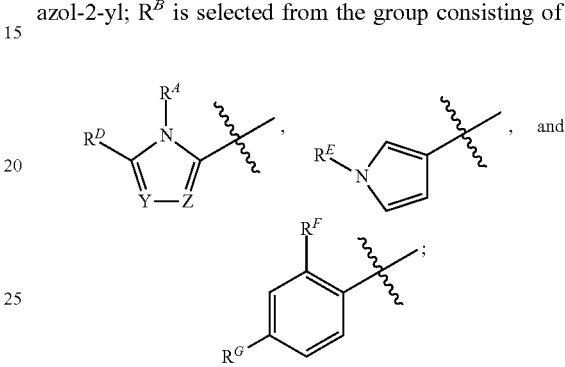

$R^C$ is

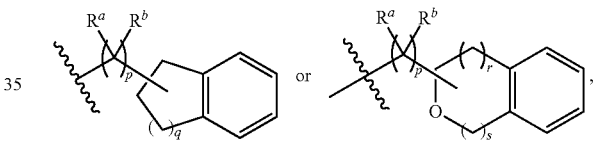

wherein $R^a$ and $R^b$ are at each occurrence independently selected from the group consisting of hydrogen and $C_1$-$C_6$alkyl, or $R^a$ and $R^b$ are taken together with the carbon atom to which they are attached to form a cyclopropyl, and wherein p is 0, 1 or 2; q is 1 or 2; r is 1 or 2; and s is 0 or 1; $R^D$ is hydrogen or phenyl; $R^E$ is phenyl optionally substituted with 1 or 2 substituents selected from the group consisting of $C_1$-$C_6$alkyl, $C_1$-$C_6$haloalkyl and halogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and Y and Z are each independently selected from the group consisting of CH or N.

In certain embodiments, $R^A$ is selected from the group consisting of 1,3-thiazol-2-yl and 1,3,4-thiadiazol-2-yl; $R^B$ is

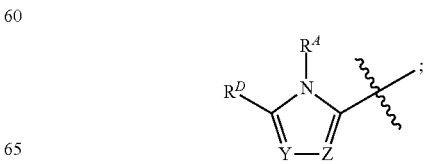

$R^C$ is selected from the group consisting of: branched-$C_4$-$C_8$alkyl, branched-$C_3$-$C_8$haloalkyl or —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl; $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen; phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl; monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

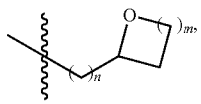

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3; phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; $R^D$ is hydrogen; and Y and Z are each CH; wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of 1,3-thiazol-2-yl and 1,3,4-thiadiazol-2-yl; $R^B$ is

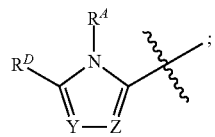

$R^C$ is phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; $R^D$ is hydrogen; and Y and Z are each CH; wherein the $C_1$-$C_3$alkyl of phenyl$C_1$-$C_3$alkyl is optionally substituted with a methyl or a cyclopropyl, wherein one atom of the cyclopropyl is an atom on the $C_1$-$C_3$alkyl chain.

In one particular subgroup, the present disclosure features compounds of formula (II) or a pharmaceutically acceptable salt thereof,

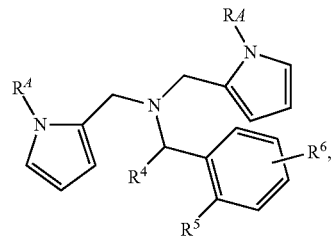

(II)

wherein
$R^A$ is selected from the group consisting of 1,3-thiazol-2-yl and 1,3,4-thiadiazol-2-yl; $R^4$ is hydrogen or methyl; $R^5$ is selected from the group consisting of $C_1$-$C_6$alkyl, $C_1$-$C_6$haloalkyl, $C_1$-$C_6$alkoxy, halo$C_1$-$C_6$alkoxy, cyano and halogen; and $R^6$ is selected from the group consisting of hydrogen, $C_1$-$C_6$alkyl, $C_1$-$C_6$haloalkyl, $C_1$-$C_6$alkoxy, halo$C_1$-$C_6$alkoxy, and halogen.

In certain embodiments, $R^4$ is hydrogen.
In certain embodiments $R^4$ is methyl.
In certain embodiments, $R^5$ is selected from the group consisting of $C_1$-$C_6$alkyl, $C_1$-$C_6$alkoxy, and halogen.
In certain embodiments, $R^6$ is selected from the group consisting of hydrogen, $C_1$-$C_6$alkoxy, and halogen.
In certain embodiment, $R^5$ is selected from the group consisting of methyl and halogen; and R6 is hydrogen.
In certain embodiments, $R^5$ is $C_1$-$C_6$alkoxy and $R^6$ is para $C_1$-$C_6$alkoxy.
In certain embodiments, $R^5$ is halogen and $R^6$ is ortho halogen.

In certain embodiments, $R^A$ is selected from the group consisting of 1,3-thiazol-2-yl and 1,3,4-thiadiazol-2-yl; $R^B$ is

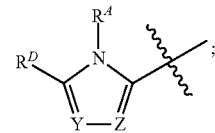

$R^C$ is 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; $R^D$ is hydrogen; and Y and Z are each CH; wherein the $C_1$-$C_3$alkyl of 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In one particular subgroup, the present disclosure features compounds of formula (I) or a pharmaceutically acceptable salt thereof,

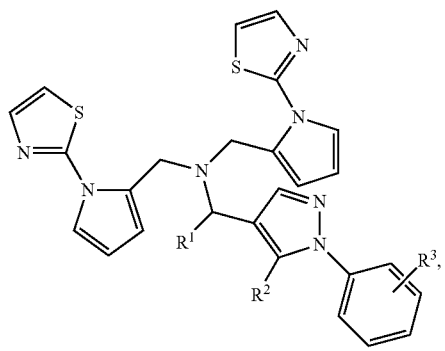

wherein
$R^1$ and $R^2$ are each independently hydrogen or $C_1$-$C_6$-alkyl; and $R^3$ is hydrogen or halogen.

In certain embodiments, $R^1$ and $R^2$ are each independently hydrogen or $C_1$-$C_6$-alkyl.

In certain embodiments, $R^1$ and $R^2$ are each hydrogen.

In certain embodiments, $R^1$ is hydrogen and $R^2$ is $C_1$-$C_6$-alkyl.

In certain embodiments, $R^1$ is $C_1$-$C_6$-alkyl and $R^2$ is hydrogen.

In certain embodiments, $R^1$ and $R^2$ are each $C_1$-$C_6$-alkyl.

In certain embodiments, $R^1$ and $R^2$ are each methyl.

In certain embodiments, $R^3$ is hydrogen or halogen.

In certain embodiments, $R^3$ is hydrogen.

In certain embodiments, $R^3$ is halogen.

In certain embodiments, $R^3$ is chloro.

In certain embodiments, $R^3$ is bromo.

In certain embodiments, $R^3$ is iodo.

In certain embodiments, $R^3$ is fluoro.

In certain embodiments, $R^3$ is an ortho substituent.

In certain embodiments, $R^3$ is a meta substituent.

In certain embodiments, $R^3$ is a para substituent.

In certain embodiments, $R^3$ is a meta fluoro substituent.

In one aspect of the disclosure are compounds of formula (I) wherein:
$R^1$ and $R^2$ are independently $C_1$-$C_6$-alkyl; and
$R^3$ is halogen.

In one particular subgroup, the present disclosure features compounds of formula (I), wherein:
$R^1$ and $R^2$ are each methyl; and
$R^3$ is a meta fluoro substituent.

In one particular subgroup, the present disclosure features compounds of formula (III) or a pharmaceutically acceptable salt thereof,

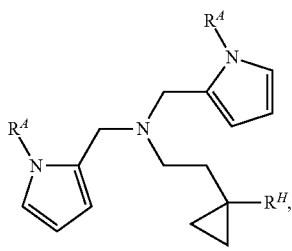

wherein,
$R^A$ is selected from the group consisting of 1,3-thiazol-2-yl and 1,3,4-thiadiazol-2-yl; and $R^H$ is 6-membered heteroaryl.

In one particular subgroup, the present disclosure features compounds of formula (III), wherein:
$R^A$ is selected from the group consisting of 1,3-thiazol-2-yl and 1,3,4-thiadiazol-2-yl; and
$R^H$ is 2-pyridinyl.

In certain embodiments, the present disclosure features compounds of formula (A), wherein, $R^A$ is selected from the group consisting of 1,3-thiazol-2-yl and 1,3,4-thiadiazol-2-yl; $R^B$ is

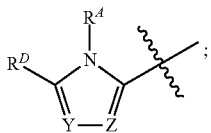

$R^C$ is phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl; $R^D$ is hydrogen; and Y and Z are each CH.

In one particular subgroup, the present disclosure features compounds of formula (IV) or a pharmaceutically acceptable salt thereof,

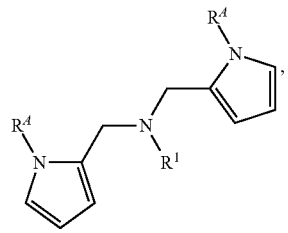

wherein,
$R^A$ is selected from the group consisting of 1,3-thiazol-2-yl and 1,3,4-thiadiazol-2-yl; and $R^I$ is 5-membered heteroaryl, wherein the or 5-membered heteroaryl is optionally substituted with 1 or 2 substituents independently selected from the group consisting of $C_1$-$C_4$alkyl, $C_1$-$C_4$alkoxy, halo$C_1$-$C_4$alkyl, halo$C_1$-$C_4$alkoxy, halogen and phenyl.

In one particular subgroup, the present disclosure features compounds of formula (IV), wherein:
$R^A$ is selected from the group consisting of 1,3-thiazol-2-yl and 1,3,4-thiadiazol-2-yl; and
$R^I$ is pyrazole optionally substituted with 1 or 2 substituents independently selected from the group consisting of $C_1$-$C_4$alkyl, and phenyl.

In certain embodiments, $R^A$ is selected from the group consisting of 1,3-thiazol-2-yl and 1,3,4-thiadiazol-2-yl; $R^B$ is

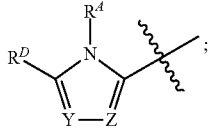

$R^C$ is selected from the group consisting of: branched-$C_4$-$C_8$alkyl, branched-$C_3$-$C_8$haloalkyl or —C($R^{1a}R^{1b}$)—O—

$C_1$-$C_6$alkyl, wherein $R^{1a}$ is hydrogen or $C_1$-$C_6$alkyl, and $R^{1b}$ is $C_1$-$C_6$alkyl; $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen; monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen; and

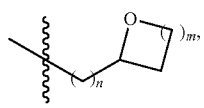

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3; $R^D$ is hydrogen; and Y and Z are each CH; wherein the $C_1$-$C_3$alkyl of monocyclic $C_5$-$C_7$cycloalkyl$C_1$-$C_3$alkyl or bicyclic $C_6$-$C_{10}$cycloalkyl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of 1,3-thiazol-2-yl and 1,3,4-thiadiazol-2-yl; $R^B$ is

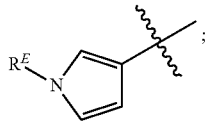

$R^C$ is 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; $R^D$ is hydrogen; $R^E$ is phenyl optionally substituted with 1 or 2 substituents selected from the group consisting of $C_1$-$C_6$alkyl, $C_1$-$C_6$haloalkyl and halogen; and Y and Z are each CH; wherein the $C_1$-$C_3$alkyl of 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In certain embodiments, $R^A$ is selected from the group consisting of 1,3-thiazol-2-yl and 1,3,4-thiadiazol-2-yl; $R^B$ is

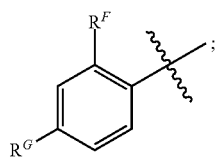

$R^C$ is 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; $R^D$ is hydrogen; $R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; $R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and Y and Z are each CH; wherein the $C_1$-$C_3$alkyl of 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In one particular subgroup, the present disclosure features compounds of formula (V), or a pharmaceutically acceptable salt thereof,

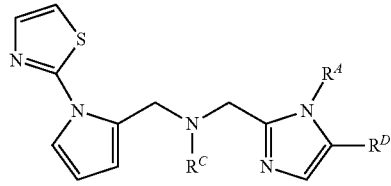

wherein, $R^A$ is selected from the group consisting of $C_1$-$C_6$alkyl, $C_1$-$C_6$alkoxyalkyl, cyano$C_1$-$C_6$alkyl, and $C_1$-$C_6$haloalkyl; $R^C$ is 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and $R^D$ is hydrogen or phenyl; wherein the $C_1$-$C_3$alkyl of the 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

In certain embodiments, the present disclosure features compounds of formula (A), wherein, $R^A$ is selected from the group consisting of $C_1$-$C_6$alkyl, $C_1$-$C_6$alkoxyalkyl, cyano$C_1$-$C_6$alkyl, and $C_1$-$C_6$haloalkyl; $R^B$ is

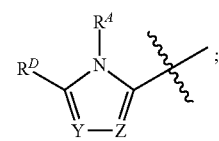

$R^C$ is 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; $R^D$ is hydrogen or phenyl; each Y is CH; and each Z is N; wherein the $C_1$-$C_3$alkyl of the 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

Exemplary compounds include, but are not limited to:
1-[1-(3-fluorophenyl)-5-methyl-1H-pyrazol-4-yl]-N,N-bis{[1-(1,3-thiazol-2-yl)-1H-pyrrol-2-yl]methyl}ethanamine;
(1S)-1-[1-(3-fluorophenyl)-5-methyl-1H-pyrazol-4-yl]-N,N-bis{[1-(1,3-thiazol-2-yl)-1H-pyrrol-2-yl]methyl}ethanamine;
(1R)-1-[1-(3-fluorophenyl)-5-methyl-1H-pyrazol-4-yl]-N,N-bis{[1-(1,3-thiazol-2-yl)-1H-pyrrol-2-yl]methyl}ethanamine;
1-[1-(3-fluorophenyl)-5-methyl-1H-pyrazol-4-yl]-N-(2-methoxybenzyl)-N-{[1-(1,3-thiazol-2-yl)-1H-pyrrol-2-yl]methyl}ethanamine;
N-{4-chloro-2-[2-(trifluoromethyl)pyrimidin-4-yl]benzyl}-1-[1-(3-fluorophenyl)-5-methyl-1H-pyrazol-4-yl]-N-{[1-(1,3-thiazol-2-yl)-1H-pyrrol-2-yl]methyl}ethanamine;
N-{[1-(2,6-dimethylphenyl)-1H-pyrrol-3-yl]methyl}-1-[1-(3-fluorophenyl)-5-methyl-1H-pyrazol-4-yl]-N-{[1-(1,3-thiazol-2-yl)-1H-pyrrol-2-yl]methyl}ethanamine;
1-[1-(3-fluorophenyl)-5-methyl-1H-pyrazol-4-yl]-N,N-bis[(1-methyl-5-phenyl-1H-imidazol-2-yl)methyl]ethanamine;
1-(2,4-dimethoxyphenyl)-N,N-bis{[1-(1,3,4-thiadiazol-2-yl)-1H-pyrrol-2-yl]methyl}methanamine;
1-methyl-N,N-bis{[1-(1,3,4-thiadiazol-2-yl)-1H-pyrrol-2-yl]methyl}-1H-pyrazol-5-amine;
1-phenyl-N,N-bis{[1-(1,3,4-thiadiazol-2-yl)-1H-pyrrol-2-yl]methyl}methanamine;
1-[(1R,4S)-bicyclo[2.2.1]hept-2-yl]-N,N-bis{[1-(1,3,4-thiadiazol-2-yl)-1H-pyrrol-2-yl]methyl}methanamine;
1-(2-methylphenyl)-N,N-bis{[1-(1,3,4-thiadiazol-2-yl)-1H-pyrrol-2-yl]methyl}methanamine;
(1R)-1-(4-fluorophenyl)-N,N-bis{[1-(1,3,4-thiadiazol-2-yl)-1H-pyrrol-2-yl]methyl}ethanamine;
1-(3,5-dichloropyridin-2-yl)-N,N-bis{[1-(1,3,4-thiadiazol-2-yl)-1H-pyrrol-2-yl]methyl}methanamine;
1-(2-fluorophenyl)-N,N-bis{[1-(1,3,4-thiadiazol-2-yl)-1H-pyrrol-2-yl]methyl}methanamine;
1-[1-(1,3,4-thiadiazol-2-yl)-1H-pyrrol-2-yl]-N-{[1-(1,3,4-thiadiazol-2-yl)-1H-pyrrol-2-yl]methyl}-N-[3-(trifluoromethyl)benzyl]methanamine;
1-(3,4-dichlorophenyl)-N,N-bis{[1-(1,3,4-thiadiazol-2-yl)-1H-pyrrol-2-yl]methyl}ethanamine;
1-(2-chlorophenyl)-N,N-bis{[1-(1,3,4-thiadiazol-2-yl)-1H-pyrrol-2-yl]methyl}methanamine;
(1R)-1-(2-chlorophenyl)-N,N-bis{[1-(1,3,4-thiadiazol-2-yl)-1H-pyrrol-2-yl]methyl}ethanamine;
(1S)-1-(2-chlorophenyl)-N,N-bis{[1-(1,3,4-thiadiazol-2-yl)-1H-pyrrol-2-yl]methyl}ethanamine;
2-[1-(pyridin-2-yl)cyclopropyl]-N,N-bis{[1-(1,3,4-thiadiazol-2-yl)-1H-pyrrol-2-yl]methyl}ethanamine;
N,N-bis{[1-(1,3,4-thiadiazol-2-yl)-1H-pyrrol-2-yl]methyl}aniline;
1-(4,4-difluorocyclohexyl)-N,N-bis{[1-(1,3,4-thiadiazol-2-yl)-1H-pyrrol-2-yl]methyl}methanamine;
2-[1-(pyridin-3-yl)cyclopropyl]-N,N-bis{[1-(1,3,4-thiadiazol-2-yl)-1H-pyrrol-2-yl]methyl}ethanamine;
N,N-bis{[1-(1,3,4-thiadiazol-2-yl)-1H-pyrrol-2-yl]methyl}-1-(thiophen-2-yl)propan-2-amine;
1-[1-(pyridin-3-yl)cyclopropyl]-N,N-bis{[1-(1,3,4-thiadiazol-2-yl)-1H-pyrrol-2-yl]methyl}methanamine;
2-[1-(pyridin-4-yl)cyclopropyl]-N,N-bis{[1-(1,3,4-thiadiazol-2-yl)-1H-pyrrol-2-yl]methyl}ethanamine;
4-[(bis{[1-(1,3,4-thiadiazol-2-yl)-1H-pyrrol-2-yl]methyl}amino)methyl]thiophene-2-carbonitrile;
1-(2,4-dichlorophenyl)-N,N-bis{[1-(1,3-thiazol-2-yl)-1H-pyrrol-2-yl]methyl}methanamine;
1-(2,4-dimethoxyphenyl)-N,N-bis{[1-(1,3-thiazol-2-yl)-1H-pyrrol-2-yl]methyl}methanamine;
1-phenyl-N,N-bis{[1-(1,3-thiazol-2-yl)-1H-pyrrol-2-yl]methyl}methanamine;
1-[(1R,4S)-bicyclo[2.2.1]hept-2-yl]-N,N-bis{[1-(1,3-thiazol-2-yl)-1H-pyrrol-2-yl]methyl}methanamine;
1-(tetrahydrofuran-2-yl)-N,N-bis{[1-(1,3-thiazol-2-yl)-1H-pyrrol-2-yl]methyl}methanamine;
1-[1-(1,3-thiazol-2-yl)-1H-pyrrol-2-yl]-N-{[1-(1,3-thiazol-2-yl)-1H-pyrrol-2-yl]methyl}-N-[4-(trifluoromethyl)benzyl]methanamine;
3-methyl-1-phenyl-N,N-bis{[1-(1,3-thiazol-2-yl)-1H-pyrrol-2-yl]methyl}-1H-pyrazol-5-amine;
1-(2,6-dichlorophenyl)-N,N-bis{[1-(1,3-thiazol-2-yl)-1H-pyrrol-2-yl]methyl}methanamine;
1-(2-methylphenyl)-N,N-bis{[1-(1,3-thiazol-2-yl)-1H-pyrrol-2-yl]methyl}methanamine;
1-(3,5-dichloropyridin-2-yl)-N,N-bis{[1-(1,3-thiazol-2-yl)-1H-pyrrol-2-yl]methyl}methanamine;
2-methyl-N,N-bis{[1-(1,3-thiazol-2-yl)-1H-pyrrol-2-yl]methyl}propan-1-amine;
1-(2-fluorophenyl)-N,N-bis{[1-(1,3-thiazol-2-yl)-1H-pyrrol-2-yl]methyl}methanamine;
1-[1-(3-fluorophenyl)-5-methyl-1H-pyrazol-4-yl]-N-[(1-methyl-5-phenyl-1H-imidazol-2-yl)methyl]-N-{[1-(1,3-thiazol-2-yl)-1H-pyrrol-2-yl]methyl}ethanamine;
1-(2,4-dichlorophenyl)-N,N-bis{[1-(1,3,4-thiadiazol-2-yl)-1H-pyrrol-2-yl]methyl}methanamine;
1-(4-fluorophenyl)-3-methyl-N,N-bis{[1-(1,3,4-thiadiazol-2-yl)-1H-pyrrol-2-yl]methyl}-1H-pyrazol-5-amine;
1-[1-(1,3-thiazol-2-yl)-1H-pyrrol-2-yl]-N-{[1-(1,3-thiazol-2-yl)-1H-pyrrol-2-yl]methyl}-N-[3-(trifluoromethyl)benzyl]methanamine;
4-[(bis{[1-(1,3-thiazol-2-yl)-1H-pyrrol-2-yl]methyl}amino)methyl]benzonitrile;
1-(3,4-dichlorophenyl)-N,N-bis{[1-(1,3-thiazol-2-yl)-1H-pyrrol-2-yl]methyl}ethanamine;
1-(2-chlorophenyl)-N,N-bis{[1-(1,3-thiazol-2-yl)-1H-pyrrol-2-yl]methyl}methanamine;
(1R)-1-(2-chlorophenyl)-N,N-bis{[1-(1,3-thiazol-2-yl)-1H-pyrrol-2-yl]methyl}ethanamine;
(1S)-1-(2-chlorophenyl)-N,N-bis{[1-(1,3-thiazol-2-yl)-1H-pyrrol-2-yl]methyl}ethanamine;
N,N-bis{[1-(1,3-thiazol-2-yl)-1H-pyrrol-2-yl]methyl}pyridazin-3-amine;
2-[1-(pyridin-2-yl)cyclopropyl]-N,N-bis{[1-(1,3-thiazol-2-yl)-1H-pyrrol-2-yl]methyl}ethanamine;
N,N-bis{[1-(1,3-thiazol-2-yl)-1H-pyrrol-2-yl]methyl}cyclohexanamine;
N,N-bis{[1-(1,3-thiazol-2-yl)-1H-pyrrol-2-yl]methyl}aniline;
1-[1-(1,3,4-thiadiazol-2-yl)-1H-pyrrol-2-yl]-N-{[1-(1,3,4-thiadiazol-2-yl)-1H-pyrrol-2-yl]methyl}-N-[4-(trifluoromethyl)benzyl]methanamine;
1-(2,6-dichlorophenyl)-N,N-bis{[1-(1,3,4-thiadiazol-2-yl)-1H-pyrrol-2-yl]methyl}methanamine;

4-[(bis{[1-(1,3,4-thiadiazol-2-yl)-1H-pyrrol-2-yl]methyl}amino)methyl]benzonitrile;

1-(4,4-difluorocyclohexyl)-N,N-bis{[1-(1,3-thiazol-2-yl)-1H-pyrrol-2-yl]methyl}methanamine;

1-[1-(1,3-thiazol-2-yl)-1H-pyrrol-2-yl]-N-{[1-(1,3-thiazol-2-yl)-1H-pyrrol-2-yl]methyl}-N-{[1-(2,2,2-trifluoroethyl)-1H-pyrazol-4-yl]methyl}methanamine;

1-[1-(difluoromethyl)-1H-imidazol-2-yl]-N,N-bis{[1-(1,3-thiazol-2-yl)-1H-pyrrol-2-yl]methyl}methanamine;

2-[1-(pyridin-3-yl)cyclopropyl]-N,N-bis{[1-(1,3-thiazol-2-yl)-1H-pyrrol-2-yl]methyl}ethanamine;

1-[(3R)-tetrahydrofuran-3-yl]-N,N-bis{[1-(1,3,4-thiadiazol-2-yl)-1H-pyrrol-2-yl]methyl}methanamine;

(1R)-1-(4-fluorophenyl)-N,N-bis{[1-(1,3-thiazol-2-yl)-1H-pyrrol-2-yl]methyl}ethanamine;

1-(furan-2-yl)-N,N-bis{[1-(1,3-thiazol-2-yl)-1H-pyrrol-2-yl]methyl}methanamine;

N,N-bis{[1-(1,3-thiazol-2-yl)-1H-pyrrol-2-yl]methyl}-1-(thiophen-2-yl)propan-2-amine;

1-[1-(pyridin-3-yl)cyclopropyl]-N,N-bis{[1-(1,3-thiazol-2-yl)-1H-pyrrol-2-yl]methyl}methanamine;

2-[1-(pyridin-4-yl)cyclopropyl]-N,N-bis{[1-(1,3-thiazol-2-yl)-1H-pyrrol-2-yl]methyl}ethanamine; or 4-[(bis{[1-(1,3-thiazol-2-yl)-1H-pyrrol-2-yl]methyl}amino)methyl]thiophene-2-carbonitrile.

Isomers

The present disclosure contemplates various stereoisomers and mixtures thereof, and these are specifically included within the scope of this disclosure. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by precipitation or chromatography and liberation of the optically pure product from the auxiliary, or (2) direct separation of the mixture of optical enantiomers on chiral chromatographic columns.

Geometric isomers may exist in the disclosed compounds. The present disclosure contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

It is to be understood that compounds disclosed herein may exhibit the phenomenon of tautomerism.

Thus, the formulae drawings within this specification can represent only one of the possible tautomeric or stereoisomeric forms. It is to be understood that the disclosed compounds encompass any tautomeric or stereoisomeric forms, and mixtures thereof, and are not to be limited merely to any one tautomeric or stereoisomeric form utilized within the naming of the compounds or formulae drawings.

Isotopes

The disclosure also include isotopically-labeled compounds, which are identical to disclosed compounds, but for the fact that one or more atoms are replaced by an atom having an atomic mass or mass number different from the atomic mass or mass number usually found in nature. Examples of isotopes suitable for inclusion in the disclosed compounds are hydrogen, carbon, nitrogen, oxygen, phosphorus, fluorine, and chlorine, such as, but not limited to, $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^{2}$H, can afford certain therapeutic advantages resulting from greater metabolic stability, for example increased in vivo half-life or reduced dosage requirements and, hence, may be employed in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (A) are $^{11}$C, $^{13}$N, $^{15}$O, and $^{18}$F. Isotopically-labeled compounds of the present disclosure can generally be prepared by conventional techniques known to those skilled in the art or by processes analogous to those described in the accompanying Examples using appropriate isotopically-labeled reagent in place of non-isotopically-labeled reagent.

Salts

This disclosure is also directed, in part, to all salts of the disclosed compounds. A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt may be pharmaceutically acceptable and/or physiologically compatible. The term "pharmaceutically acceptable" is used adjectivally in this disclosure to mean that the modified noun is appropriate for use as a pharmaceutical product or as a part of a pharmaceutical product. Pharmaceutically acceptable salts include, for example, salts commonly used to form alkali metal salts and to form addition salts of free acids or free bases. In general, these salts typically may be prepared by conventional means by reacting, for example, the appropriate acid or base with a disclosed compound.

Pharmaceutically acceptable acid addition salts of the disclosed compounds can be prepared from an inorganic or organic acid. Examples of suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the disclosed compounds include, for example, metallic salts and organic salts. Metallic salts may include alkali metal (group Ia) salts, alkaline earth metal (group IIa) salts, and other physiologically acceptable metal salts. Such salts may be made from aluminum, calcium, lithium, magnesium, potassium, sodium, and zinc. Organic salts can be made from amines, such as tromethamine, diethylamine, N,N-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Purity

The disclosed compounds (and salts thereof) with any level of purity (including pure and substantially pure) are within the scope of the present disclosure. The term "substantially pure" in reference to a compound/salt/isomer, means that the preparation/composition containing the compound/salt/isomer contains more than about 85% by weight of the compound/salt/isomer, more than about 90% by weight of the compound/salt/isomer, more than about 95% by weight of the compound/salt/isomer, more than about 97% by weight of the compound/salt/isomer, and more than about 99% by weight of the compound/salt/isomer.

Compositions

The disclosure is also directed, in part, to compositions comprising one or more of the disclosed compounds and/or salts thereof. In some embodiments, the compositions comprise one or more substantially phase pure crystalline forms. The compositions may be pharmaceutical compositions.

In some embodiments, the compositions further comprise one or more additional therapeutic agents. Such therapeutic agents may include, for example, one or more therapeutic agents used to treat respiratory syncytial virus (e.g., ribavirin).

The components of the compositions may depend on the method of administration, and may comprise one or more conventional pharmaceutically acceptable carriers, adjuvants, and/or vehicles (together referred to as "excipients"). Formulation of drugs is generally discussed in, for example, Hoover, J., *Remington's Pharmaceutical Sciences* (Mack Publishing Co., 1975) and Ansel's *Pharmaceutical Dosage Forms and Drug Delivery Systems* (Lippincott Williams & Wilkins, 2005).

The disclosed pharmaceutical compositions may be administered to a patient in need thereof via a variety of routes, such as orally, parenterally, sublingually, rectally, topically or by inhalation. Topical administration may involve the use of transdermal administration such as transdermal patches or iontophoresis devices. Parenteral administration includes, but is not limited to, subcutaneous, intravenous, intramuscular or intrasternal injections, and infusion techniques.

Solid dosage forms for oral administration include, for example, capsules, tablets, pills, powders, and granules. In such solid dosage forms, the disclosed compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs containing inert diluents commonly used in the art (e.g., water). Such compositions may also comprise, for example, wetting, emulsifying, suspending, flavoring (e.g., sweetening), and/or perfuming agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the excipients mentioned for use in the formulations for oral administration. A compound or salt of the invention can be dissolved in water, polyethylene glycol, propylene glycol, ethanol, corn oil, cottonseed oil, peanut oil, sesame oil, benzyl alcohol, sodium chloride, and/or various buffers. The pH may be adjusted, if necessary, with a suitable acid, base, or buffer.

Suppositories for rectal administration may be prepared by, for example, mixing a compound or salt of the invention with a suitable nonirritating excipient that is solid at ordinary temperatures, but liquid at the rectal temperature, and will, therefore, melt in the rectum to release the drug. Suitable excipients include, for example, cocoa butter; synthetic mono-, di-, or triglycerides, fatty acids, and/or polyethylene glycols.

Topical administration includes the use of transdermal administration, such as transdermal patches or iontophoresis devices.

The disclosed compounds or pharmaceutical compositions may be formulated to be suitable for inhalation. The pharmaceutical composition may be in the form of a solution, suspension, powder or other suitable form for pulmonary administration. These compositions may be administered to the lungs by any suitable delivery method such as, for example, in an aerosol, atomized, nebulized, or vaporized form through devices known in the art to affect such delivery. The amount of the disclosed pharmaceutical composition may be controlled by providing a valve to deliver a metered amount such as in a metered dose inhalers (MDI) that delivers a fixed dose in a spray with each actuation of the device. The pharmaceutical compositions may be formulated with one or more suitable propellants, such as, for example, dichlorodifluoromethane, trichlorofluoromethane, dichlorotetrafluoroethane, carbon dioxide or other suitable gas. Capsules and cartridges for use in an inhaler or insufflator may be formulated containing a powder mix of the disclosed compounds or pharmaceutical compositions and a suitable powder base such as lactose or starch.

The pharmaceutical compositions may be formulated with one or more binding agent as a dry powder for inhalation.

The disclosed compounds or pharmaceutical compositions may be in the form of sustained- or controlled-delivery formulations. Techniques for making such sustained- and controlled-delivery formulations are well-known to those skilled in the art. Among these are delivery methods that use liposome carriers, bio-erodible microparticles, porous beads, and semi-permeable polymer matrices.

Other excipients and modes of administration known in the pharmaceutical art also may be used.

The total daily dose of the disclosed compounds or salts thereof (administered in single or divided doses) may be from about 0.001 to about 100 mg/kg, from about 0.001 to about 30 mg/kg, or from about 0.01 to about 10 mg/kg (i.e., mg of the compound or salt per kg body weight). Dosage unit compositions may contain such amounts or submultiples thereof to make up the daily dose. In many instances, the administration of the disclosed compounds or salts thereof will be repeated a plurality of times. Multiple doses per day typically may be used to increase the total daily dose, if desired.

Factors affecting the dosage regimen include the type, age, weight, sex, diet, and condition of the patient; the severity of the pathological condition; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the dosage regimen set forth above.

Kits

This disclosure is also directed, in part, to kits comprising one or more of the disclosed compounds and/or salts thereof. The kits may optionally contain one or more additional therapeutic agents and/or instructions for, for example, using the kit.

Methods of Use.

This disclosure is directed, in part, to a method for inhibiting infection and/or replication of an RNA virus. The method comprises exposing the virus to one or more of the disclosed compounds and/or salts thereof. In embodiments, infection and/or replication of the RNA virus is inhibited in vitro. In embodiments, infection and/or replication of the RNA virus is inhibited in vivo. In embodiments, the RNA virus whose infection and/or replication is being inhibited is a single-stranded, negative sense RNA virus. In embodiments, the RNA virus whose infection and/or replication is being inhibited is a virus from the Paramyxoviridae family. In embodiments, the RNA virus whose infection and/or replication is being inhibited is RSV.

The term "inhibiting" means reducing the level of infection and/or RNA virus replication either in vitro or in vivo. The inhibition may act on any stage of viral infection and/or replication, such as (but not exclusively) attachment, penetration, uncoating, genome replication, assembly, maturation or egress from infected cells. The target of the compound may be either a viral or host component (or rarely both) involved in viral infection and/or replication. For example, if a disclosed compound/salt reduces the level of infection and/or RNA virus replication by at least about 10% compared to the level of RNA virus replication before the virus is exposed to the compound/salt, then the compound/salt inhibits RNA virus replication. In some embodiments, the compound/salt can inhibit infection and/or RNA virus replication by at least about 20%, at least about 30%, at least about 40%, at least about 50%, at least about 60%, at least about 70%, at least about 80%, at least about 90%, or at least about 95%.

This disclosure also is directed, in part, to a method for treating RSV infection in a subject in need of such treatment. These methods comprise administering to the subject one or more of the disclosed compounds and/or salts thereof, and, optionally, one or more additional therapeutic agents. In some embodiments, a therapeutically effective amount of the compound(s) and/or salt(s) thereof is administered to the subject. "Treating" means ameliorating, suppressing, eradicating, preventing, reducing the risk of, and/or delaying the onset of the infection or disease being treated. For example, the disclosed compounds and/or salts thereof may be used for prophylaxis to prevent infection of uninfected subjects, and/or the spread of the virus to the lower respiratory tract in patients already infected with the virus. The term "treating" encompasses administration of the disclosed compounds and/or salts thereof to a patient at risk for RSV infection. Patients at risk for RSV infection may include premature infants, children with bronchopulmonary dysplasia, children with congenital heart or lung disease, the elderly and immunocompromised and other patients who are unable to mount a sufficient immune responses due to their immature or weaker immune systems. The disclosed compounds and/or salts thereof may be administered to patients with a low tolerance to the side effects of current therapies.

The methods of treatment are particularly suitable for use with humans, but may be used with other animals. A "therapeutically effective amount" or "effective amount" is an amount that will substantially achieve the goal of treating the targeted condition.

In embodiments, the disclosed methods comprise combination therapy, wherein the disclosed compound(s) and/or salt(s) is/are co-administered with a second compound, such as, for example, another therapeutic agent used to treat RSV such as, for example, the current standard of therapy, and other antivirals. In these co-administration embodiments, the disclosed compound(s) and/or salt(s) and the second, etc. therapeutic agent(s) may be administered in a substantially simultaneous manner (e.g., within at least about 5 minutes of each other), in a sequential manner, or both. For example, the disclosed compound(s) and/or salt(s) may be administered to a patient before, during or after treatment with the current standard of therapy, if such an administration is deemed medically necessary and/or appropriate.

This disclosure also is directed, in part, to uses of one or more of the disclosed compounds and/or salts, and, optionally, in combination with one or more additional therapeutic agents to prepare a medicament. In some embodiments, the medicament is for co-administration with one or more additional therapeutic agents.

In some embodiments, the medicament is for inhibiting infection and/or replication of an RNA virus.

In some embodiments, the medicament is for preventing and/or treating RSV.

In embodiments, one or more of the disclosed compounds and/or salts may be used to prevent and/or treat RSV infections caused by one or both groups A or B RSV virus.

In embodiments, one or more of the disclosed compounds and/or salts may be used to inhibiting infection and/or replication of one or both of group A or group B RSV virus.

This disclosure also is directed, in part, to one or more of the disclosed compounds and/or salts of the present disclosure, and, optionally, in combination with one or more additional therapeutic agents, for use in inhibiting infection and/or replication of an RNA virus and/or for use in inhibiting infection and/or replication of RSV.

BIOLOGICAL ASSAYS

Cells and Virus

HEp-2 cells and RSV (Group A, Long Strain) were obtained from the American Type Culture Collection (Manassas, Va.).

Antiviral Assay

A cytopathic effect (CPE) protection assay was performed to determine the ability of a compound to protect the cells from viral infection and thus the CPE induced by viral infection. 96-Well plates were first seeded with $3 \times 10^3$ HEp-2 cells per well in Dulbecco's modified Eagle's medium (DMEM) containing 10% fetal bovine serum (FBS). One day after the cells were seeded, they were preincubated with serial dilutions of compounds prepared in 100 μL assay medium (DMEM mixed with F12 medium at a 1:1 ratio, supplemented with 2% FBS and 1 mM sodium pyruvate) for 1 hour at 37° C. 100 μL of assay medium containing 0.2 multiplicity of infection (MOI) of RSV was then added to each well of cells. In addition to wells containing infected cells incubated with compounds, each plate also contained replicates of two kinds of controls: (1) Virus control contained cells infected with 0.2 MOI of RSV in assay medium, (2) Uninfected cell control contained cells incubated with assay medium only. After 4 days of incubation at 37° C., the viability of cells was assessed using MTT (Thiazolyl blue tetrazolium bromide, Sigma). A stock solution of MTT, at a concentration of 4 mg/mL in phosphate-buffered saline, was added to all wells at 25 μL per well. Plates were further incubated for 4 hours, and each well was then treated with 50 μL of a solution containing 20% sodium dodecyl sulfate (SDS) and 0.02 N HCl. After an overnight incubation, the plates were measured on a BioTek® microtiter plate reader at wavelengths of 570 nm and 650 nm. The MTT detection is based on the fact that viable (uninfected) cells can reduce the tetrazolium salts into colored formazan products, which can then be quantitated by spectrometry. Based on the spectrometric absorbance of each sample, the percent of protection from CPE, which is an indicator of protection from viral infection, can be calculated for each compound and the 50% effective concentrations ($EC_{50}$) can be calculated using a nonlinear regression curve fitting equation provided by the GraphPad Prism® 4 software. Using the above-described assay, compounds of the present disclosure showed obvious inhibitory activities against RSV replication. Results are shown in Table 1.

Cytotoxicity Assay

Cytotoxicity of the compounds was determined in experiments done in parallel with the antiviral assays. To do this, 100 μL of assay medium was added to the wells of HEp-2 cells pretreated with 100 μL serially diluted compounds as described above. After 4 days of incubation, the viability of the cells was determined by the MTT assay in the same way as detailed in the "Antiviral Assay" method. Results were expressed as 50% toxicity dose ($TD_{50}$) values. Results are shown in Table 1.

Compound Testing Strategy

Compounds were tested to determine both their antiviral and toxicity to determine their therapeutic window. Determination of the $EC_{50}$ and $TD_{50}$ of these active compounds were repeated one additional time to confirm the window. Results are shown in Table 1.

TABLE 1

| Example | RSV EC50 (μM) | MTT TD50 (μM) | Window (TD50/EC50) |
|---|---|---|---|
| 1 | 0.12 | 11 | 99 |
| 2 | 0.071 | >32 | >450 |
| 3 | 0.96 | >32 | >33 |
| 4 | >0.48 | 0.48 | NW |
| 5 | >0.11 | 0.11 | NW |
| 6 | >0.57 | 0.57 | NW |
| 7 | 0.32 | 5.2 | 16 |
| 8 | 0.24 | 22 | 88 |
| 9 | 4.9 | >32 | >6.5 |
| 10 | 0.52 | 97 | 187 |
| 11 | 0.56 | 26 | 46 |
| 12 | 0.064 | >10 | >157 |
| 13 | 14 | 93 | 7 |
| 14 | 4.8 | 90 | 19 |
| 15 | 0.12 | 67 | 547 |
| 16 | 2.1 | 30 | 14 |
| 17 | 15 | >32 | >2 |
| 18 | 0.062 | >32 | >512 |
| 19 | 2.8 | >32 | >11 |
| 20 | 0.36 | >32 | >88 |
| 21 | 0.062 | >32 | >518 |
| 22 | 28 | >32 | >1.1 |
| 23 | 2.4 | >100 | >41 |
| 24 | 2.9 | >100 | >35 |
| 25 | 7.5 | 55 | 7.3 |
| 26 | 1.1 | >100 | >94 |
| 27 | 0.81 | >32 | >40 |
| 28 | 0.76 | >100 | >132 |
| 29 | 0.32 | >32 | >101 |
| 30 | 0.054 | 4.9 | 91 |
| 31 | 0.11 | 5.4 | 48 |
| 32 | 0.41 | 4.1 | 10 |
| 33 | 4.6 | 16 | 3 |
| 34 | 3.4 | 34 | 10 |
| 35 | 0.047 | >32 | >677 |
| 36 | 0.033 | 24 | 719 |
| 37 | 0.033 | 7.1 | 213 |
| 38 | 0.31 | 11 | 35 |
| 39 | 3.4 | 8.3 | 2 |
| 40 | 0.018 | 6.3 | 353 |
| 41 | >5.6 | 5.6 | NW |
| 42 | >32 | 32 | NW |
| 43 | >32 | >32 | NW |
| 44 | 0.12 | 38 | 327 |
| 45 | 0.96 | >32 | >33 |
| 46 | 0.55 | >32 | >58 |
| 47 | 0.015 | 7.0 | 472 |
| 48 | 0.11 | 6.7 | 63 |
| 49 | 0.045 | 4.3 | 97 |
| 50 | >100 | >100 | NW |
| 51 | 0.045 | 6.2 | 137 |
| 52 | 0.10 | 7.2 | 72 |
| 53 | 2.7 | >32 | >12 |
| 54 | >21 | 21 | NW |
| 55 | >32 | >32 | NW |
| 56 | 46 | >100 | >2.2 |
| 57 | 0.31 | 20 | 64 |
| 58 | 0.52 | 49 | 94 |
| 59 | 4.1 | 35 | 9 |
| 60 | 0.85 | >100 | >117 |
| 61 | >100 | >100 | NW |
| 62 | >3.0 | 3.0 | NW |
| 63 | 0.26 | 20 | 77 |
| 64 | 0.33 | 5.6 | 17 |

TABLE 1-continued

| Example | RSV EC50 (μM) | MTT TD50 (μM) | Window (TD50/EC50) |
|---|---|---|---|
| 65 | 0.090 | 25 | 273 |
| 66 | 0.20 | 14 | 73 |
| 67 | 0.082 | >32 | >389 |

NW: No window

General Synthesis

Additional information about the preparation of compounds of formula (A) (and its salts) is provided in the general discussion and/or specific synthesis examples below.

The disclosed compound may be made by methods known in the art or the methods described below and variations thereof.

Abbreviations: Et for ethanol; EtOH for ethanol; iPr for isopropyl; Pr for propyl; and THF for tetrahydrofuran.

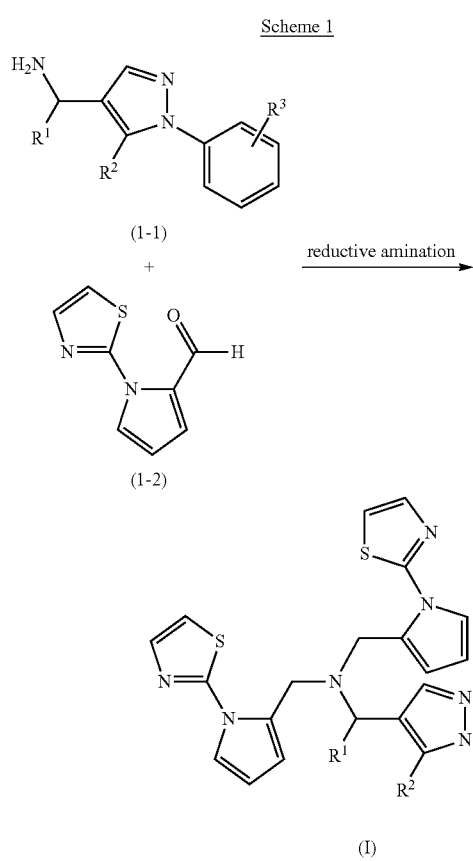

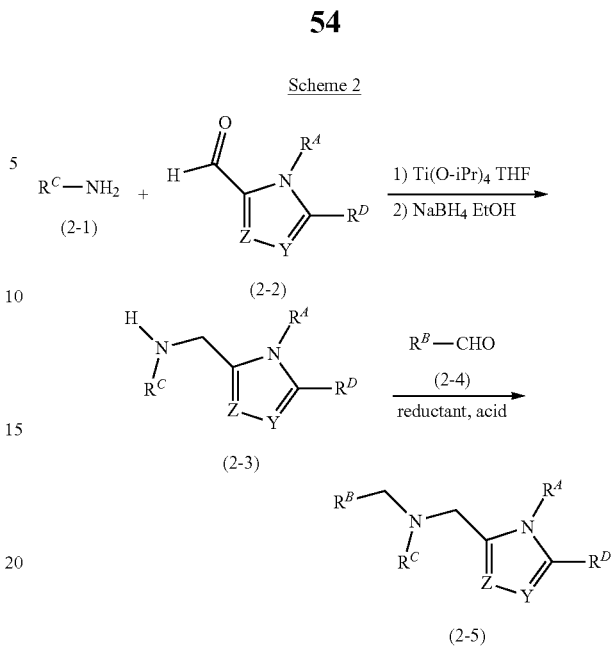

Amines of formula (2-1) can be converted through two sequential reductive amination steps to compounds of formula (2-5). Accordingly, amines of formula (2-1) can be reacted with aldehydes of formula (2-2) initially in the presence of titanium(IV) isopropoxide in a solvent such as tetrahydrofuran and then with a reductant such as sodium borohydride in a solvent such as ethanol to give compounds of formula (2-3). Compounds of formula (2-3) can then be reacted with aldehydes of formula (2-4) in the presence of a reductant such as sodium borohydride, sodium cyanoborohydride, or sodium triacetoxy borohydride in a solvent such as ethanol, methanol, dichloromethane or combinations thereof in the presence of an acid such as acetic acid to give compounds of formula (2-5). The reductant may be added as a solid, a solution, or as the reagent bound to a solid support resin. Compounds of formula (2-5) are representative of compounds of formula (A).

Amines of formula (1-1) can be converted to a compounds of formula (I) by reductive amination with an aldehyde of formula (1-2). Compounds of formula (1-1) can be reacted with an excess of a compound of formula (1-2) in the presence of acetic acid and a reductant such as sodium triacetoxyborohydride or sodium cyanoborohydride in a solvent such as tetrahydrofuran at room temperature over 4-24 hours to give a compounds of formula (I).

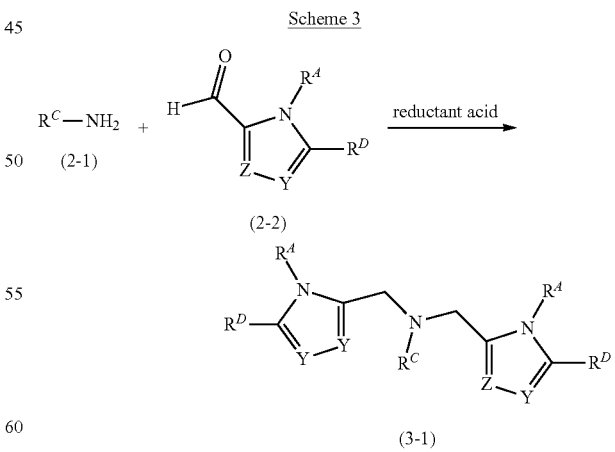

Amines of formula (2-1) can be converted with a reductive amination to compounds of formula (3-1). Amines of formula (2-1) can be reacted with 1.5 to 4 equivalents of aldehydes of formula (2-2) in the presence of a reductant such as sodium borohydride, sodium cyanoborohydride, or sodium triacetoxy borohydride in a solvent such as ethanol, methanol, dichloromethane or combinations thereof in the presence of an acid such as acetic acid to give compounds of formula (3-1). The reductant may be added as a solid, a solution, or as the reagent bound to a solid support resin. The reaction can be conducted at ambient temperature over 2 to 7 days or heated to 60-80° C. for 8-36 hours. The heating can be accomplished conventionally or with microwave irradiation. Compounds of formula (3-1) are representative of compounds of formula (A).

Compounds are shown wherein an aromatic ring (e.g., phenyl) is substituted with groups in a particular regiochemistry (e.g., para). A starting material or intermediate with para-substitution provides a final product with para-substitution in the foregoing Schemes. It is understood by one of skill in the art that substitution in the foregoing Schemes of a starting material or intermediate with a different regiochemistry (e.g., meta) would provide a final product with a different regiochemistry. For example, replacement of a para-substituted starting material or intermediate in the foregoing Schemes with a meta substituted starting material or intermediate would lead to a meta-substituted product.

If a moiety described herein (e.g., —$NH_2$ or —OH) is not compatible with the synthetic methods, the moiety may be protected with a suitable protecting group that is stable to the reaction conditions used in the methods. The protecting group may be removed at any suitable point in the reaction sequence to provide a desired intermediate or target compound. Suitable protecting groups and methods for protecting or deprotecting moieties are well known in the art, examples of which can be found in Greene TW and Wuts PGM, *Protective Groups in Organic Synthesis*, (3$^{rd}$ ed., John Wiley & Sons, NY (1999)). Optimum reaction conditions and reaction times for each individual step may vary depending on the particular reactants employed and substituents present in the reactants used. Solvents, temperatures and other reaction conditions may be readily selected by one of ordinary skill in the art based on the present disclosure.

Other disclosed compounds can be similarly prepared according the procedures described in the following disclosure of intermediates, procedures, and examples as appreciated by those skilled in the art.

It should be understood that the above-described embodiments and schemes and the following intermediates, general procedures, and examples disclosure are given by way of illustration, not limitation. Various changes and modifications within the scope of the present disclosure will become apparent to those skilled in the art from the present description.

EXAMPLES

Abbreviations: DMSO for dimethyl sulfoxide; ESI for electrospray ionization; HPLC for high performance liquid chromatography; and MP for macroporous resin.

Example 1

1-[1-(3-fluorophenyl)-5-methyl-1H-pyrazol-4-yl]-N,N-bis{[1-(1,3-thiazol-2-yl)-1H-pyrrol-2-yl]methyl}ethanamine Step A 3-[(dimethylamino)methylene]pentane-2,4-dione 1,1-Dimethoxy-N,N-dimethylmethanamine (190.44 g, 1.59 mol) was added to a solution of pentane-2,4-dione (100.0 g, 1.0 mol) in toluene (400 mL), and the reaction mixture was heated to reflux for 4 hours. The reaction mixture was cooled to ambient temperature, volatiles were removed under reduced pressure, and the residue was dissolved in ether. The ether solution was placed in a refrigerator, and a solid precipitated. The solid was collected by filtration, washed with cold ether, and air dried to provide the titled compound (120.9 g, 78%). $^1$H NMR (400 MHz, CDCl$_3$) δ ppm 2.31 (s, 6H), 2.98 (br. s, 6H), 7.43 (s, 1H); MS (ESI) m/z 156.2 (M+1)$^+$.

Step B

1-[1-(3-fluorophenyl)-5-methyl-1H-pyrazol-4-yl]ethanone (3-Fluorophenyl)hydrazine hydrochloride (41.91 g, 257.7 mmol) and sodium hydroxide (10.31 g, 257.7 mmol) were added to a solution of 3-[(dimethylamino)methylene]pentane-2,4-dione (40.0 g, 257.7 mmol, Step A) in ethanol (750 mL) and water (150 mL). The reaction mixture was heated at reflux overnight and then concentrated under reduced pressure. The residue was diluted with ethyl acetate (400 mL) and washed with 1 M potassium carbonate solution (2×150 mL) and water (200 mL). The organic layer was dried over anhydrous sodium sulfate, filtered and concentrated under reduced pressure. The residue was dissolved in ethanol, the solution was stored in a refrigerator, and a solid precipitated. The solid was collected by filtration. A second precipitation from ethanol to further purify the solid provided the titled compound (24.39 g, 43%). $^1$H NMR (400 MHz, CDCl$_3$) δ ppm 2.44 (s, 3H), 2.53 (s, 3H), 7.51-7.32 (m, 3H), 7.65-7.57 (m, 1H), 8.25 (s, 1H); MS (ESI) m/z 219.2 (M+1)$^+$.

Step C

1-[1-(3-fluorophenyl)-5-methyl-1H-pyrazol-4-yl]-N-hydroxyethanimine

A solution of hydroxylamine hydrochloride (1.06 g, 15.4 mmol) in water (7 mL) was neutralized with sodium hydrogen carbonate (1.29 g, 15.4 mmol). Then 1-[1-(3-fluorophenyl)-5-methyl-1H-pyrazol-4-yl]ethanone (2.204 g, 10.1 mmol, Step B) in ethanol (30 mL) was added, and the solution was heated at reflux overnight. The reaction mixture was cooled to ambient temperature. The precipitate was collected by filtration, washed with cold ethanol and air dried to provide the titled compound (2.11 g, 89%) as a white solid. $^1$H NMR (400 MHz, CDCl$_3$) δ ppm 2.13 (s, 3H), 2.47 (s, 3H), 7.31 (t, J=8.6 Hz, 1H), 7.40 (d, J=7.8 Hz, 1H), 7.45 (d, J=9.9 Hz, 1H), 7.58 (q, J=7.3 Hz, 1H), 7.87 (s, 1H), 10.86 (s, 1H); MS (ESI) m/z 234.3 (M+1)$^+$.

Step D

1-[1-(3-fluorophenyl)-5-methyl-1H-pyrazol-4-yl]ethanamine

Nickel catalyst (60% weight nickel on silica, 87 mg, 0.892 mmol) was added to a solution of 1-[1-(3-fluorophenyl)-5-methyl-1H-pyrazol-4-yl]-N-hydroxyethanimine (2.080 g, 8.918 mmol, Step C) in toluene (40 mL) in a stainless steel autoclave. The air in the reaction vessel was replaced by argon, and then the reaction mixture was hydrogenated (1175 psi) at 150° C. overnight. The autoclave was cooled to room temperature and flushed with argon. The catalyst was removed by filtration, and the filtrate was concentrated under reduced pressure. The titled compound (1.516 g, 6.914 mmol, oil) was used in the next stage without further purification. MS (ESI) m/z 220.2 (M+1)+.

Step E 2-(1H-pyrrol-1-yl)-1,3-thiazole

To a solution of 2-aminothiazole (20.0 g, 199.7 mmol) in glacial acetic acid (200 mL) was added 2,5-dimethoxytetrahydrofuran (26.3 g, 25.9 mL, 199.7 mmol). The reaction mixture was heated to reflux for 2 hours, the resultant solution was cooled to ambient temperature, and then water (700 mL) was added. The pH was adjusted to 8-9 by addition of solid sodium carbonate. The aqueous solution was extracted with diethyl ether (3×100 mL), and the combined organic extracts were washed with brine and dried over sodium sulfate. The drying agent was removed by filtration, and the filtrate was concentrated under reduced pressure. The residue was subjected to column chromatography on silica gel eluted with hexane/ethyl acetate (1:1) to afford the titled compound (20.46 g, 68%) as a yellow oil. $^1$H NMR (400 MHz, CDCl$_3$) δ ppm 6.36 (t, J=2.1 Hz, 2H), 6.98 (d, J=3.5 Hz, 1H), 7.36 (t, J=2.1 Hz, 2H), 7.49 (d, J=3.5 Hz, 1H); MS (ESI) m/z 151.0 (M+1)+.

Step F 1-(1,3-thiazol-2-yl)-1H-pyrrole-2-carbaldehyde

A solution of phosphorus (V) oxychloride (73.3 mmol, 6.83 mL) in dichloroethane (40 mL) was added to a cooled (0-5° C.) solution of N,N-dimethylformamide (73.3 mmol, 5.67 mL) in 1,2-dichloroethane (40 mL) over a period of 5-10 minutes. After stirring at ambient temperature for 45 minutes, the suspension was cooled (0-5° C.) again and treated with a solution of 2-(1H-pyrrol-1-yl)-1,3-thiazole (66.6 mmol, 10.01 g, Step E) in 1,2-dichloroethane (40 mL). The mixture was stirred at ambient temperature for 3 hours. Then the reaction mixture was poured onto crushed ice (300 g) containing 50% sodium hydroxide (40 mL) and stirred for 10 minutes. The organic layer was separated, and the aqueous phase was extracted with chloroform (3×100 mL). The combined organic layers were washed with water, dried, and concentrated. The residual oil was subjected to column chromatography on silica gel eluted with hexane/ethyl acetate (4:1) to afford the titled compound (9.98 g, 56.0 mmol) as a yellow oil. $^1$H NMR (400 MHz, CDCl$_3$) δ ppm 6.52 (t, J=3.2 Hz, 1H), 7.28 (dd, J=3.8 Hz, J=1.6 Hz, 1H), 7.75-7.70 (m, 3H), 9.87 (s, 1H).

Step G

1-[1-(3-fluorophenyl)-5-methyl-1H-pyrazol-4-yl]-N,N-bis{[1-(1,3-thiazol-2-yl)-1H-pyrrol-2-yl]methyl}ethanamine To a solution of 1-[1-(3-fluorophenyl)-5-methyl-1H-pyrazol-4-yl]ethanamine (572 mg, 2.609 mmol, Step D) in dry tetrahydrofuran (40 mL), 1-(1,3-thiazol-2-yl)-1H-pyrrole-2-carbaldehyde (1860 mg, 10.435 mmol, Step F) and acetic acid (0.783 mmol, 47 mg, 0.045 mL) were added, and the reaction mixture was stirred at room temperature overnight. Sodium triacetoxyborohydride (2765 mg, 13.044 mmol) was added in one portion, and the reaction mixture was stirred at room temperature overnight. Aqueous sodium hydroxide (150 mL, 2 M) was added followed by concentration under reduced pressure. The residue was extracted with chloroform (4×40 mL). The combined organic layers were washed with water (20 mL) and dried over sodium sulfate. Filtration and concentration in vacuo afforded an oil which was subjected to column chromatography on silica gel eluted with a mixture of chloroform/methanol (38:1) to provide the titled compound (718 mg, 50%) as brown oil. $^1$H NMR (400 MHz, CDCl$_3$) δ ppm 1.35 (d, J=6.98 Hz, 3H) 1.78 (s, 3H) 3.82 (d, J=14.78 Hz, 2H) 4.00 (q, J=6.81 Hz, 1H) 4.09 (d, J=14.51 Hz, 2H) 6.23 (m, 4H) 6.92 (d, J=3.49 Hz, 2H) 7.12 (m, 6H) 7.41 (m, 3H) 7.56 (s, 1H); MS (ESI) m/z 544.7 (M+1)+.

Example 2

(1S)-1-[1-(3-fluorophenyl)-5-methyl-1H-pyrazol-4-yl]-N,N-bis{[1-(1,3-thiazol-2-yl)-1H-pyrrol-2-yl]methyl}ethanamine and Example 3

(1R)-1-[1-(3-fluorophenyl)-5-methyl-1H-pyrazol-4-yl]-N,N-bis{[1-(1,3-thiazol-2-yl)-1H-pyrrol-2-yl]methyl}ethanamine Racemic 1-[1-(3-fluorophenyl)-5-methyl-1H-pyrazol-4-yl]-N,N-bis{[1-(1,3-thiazol-2-yl)-1H-pyrrol-2-yl]methyl}ethanamine (Example 1) was resolved on a chiral HPLC (column: Phenomenex® Lux® Cellulose-4, 250×30 mm, 5 µm; isocratic mixture acetonitrile/isopropanol (90:10); 30 minute run; flow rate 25 mL/minute) to afford the titled compounds:

(1S)-1-[1-(3-fluorophenyl)-5-methyl-1H-pyrazol-4-yl]-N,N-bis{[1-(1,3-thiazol-2-yl)-1H-pyrrol-2-yl]methyl}ethanamine (eluted first): $^1$H NMR (400 MHz, CD$_3$OD) δ ppm 1.32 (d, J=6.7 Hz, 3H), 1.69 (s, 3H), 3.76 (d, J=14 Hz, 2H), 3.90-3.99 (m, 1H), 4.11 (d, J=14.2 Hz, 2H), 6.22 (d, J=8.3 Hz, 4H), 7.07-7.25 (m, 7H), 7.32-7.40 (m, 2H), 7.51-7.56 (m, 2H); MS (ESI) m/z 544.7 (M+1)+.

(1R)-1-[1-(3-fluorophenyl)-5-methyl-1H-pyrazol-4-yl]-N,N-bis{[1-(1,3-thiazol-2-yl)-1H-pyrrol-2-yl]methyl}ethanamine (eluted second): $^1$H NMR (400 MHz, CD$_3$OD) δ ppm 1.32 (d, J=6.7 Hz, 3H), 1.69 (s, 3H), 3.76 (d, J=14 Hz, 2H), 3.90-3.99 (m, 1H), 4.11 (d, J=14.2 Hz, 2H), 6.22 (d, J=8.3 Hz, 4H), 7.07-7.25 (m, 7H), 7.32-7.40 (m, 2H), 7.51-7.56 (m, 2H); MS (ESI) m/z 544.7 (M+1)+.

Example 4

1-[1-(3-fluorophenyl)-5-methyl-1H-pyrazol-4-yl]-N-(2-methoxybenzyl)-N-{[1-(1,3-thiazol-2-yl)-1H-pyrrol-2-yl]methyl}ethanamine Step A 1-[1-(3-fluorophenyl)-5-methyl-1H-pyrazol-4-yl]-N-{[1-(1,3-thiazol-2-yl)-1H-pyrrol-2-yl]methyl}ethanamine oxalate The titled compound was prepared by reacting 1-[1-(3-fluorophenyl)-5-methyl-1H-pyrazol-4-yl]ethanamine (Example 1, Step D) with 1-(thiazol-2-yl)-1H-pyrrole-2-carbaldehyde (Aldrich) in a one-pot 2-step procedure in the presence of titanium(IV) isopropoxide in tetrahydrofuran and then with sodium borohydride in ethanol. The free amine was treated with oxalic acid in heated tetrahydrofuran followed by cooling to ambient temperature to obtain the titled compound as an oxalate salt. $^1$H NMR (400 MHz, DMSO-$d_6$) δ ppm 7.73 (s, 1H), 7.68-7.48 (m, 3H), 7.48-7.32 (m, 3H), 7.28 (dd, J=9.8, 7.3 Hz, 1H), 6.37 (s, 1H), 6.29 (t, J=3.3 Hz, 1H), 4.35-3.90 (m, 3H), 2.28 (s, 3H), 1.46 (d, J=6.7 Hz, 3H). MS (ESI+) m/z 382 (M+H)$^+$.

Step B

1-[1-(3-fluorophenyl)-5-methyl-1H-pyrazol-4-yl]-N-(2-methoxybenzyl)-N-{[1-(1,3-thiazol-2-yl)-1H-pyrrol-2-yl]methyl}ethanamine 1-[1-(3-Fluorophenyl)-5-methyl-1H-pyrazol-4-yl]-N-{[1-(1,3-thiazol-2-yl)-1H-pyrrol-2-yl]methyl}) ethanamine oxalate (23 mg, 0.05 mmol) dissolved in dichloromethane (1.0 mL) was treated sequentially with 2-methoxybenzaldehyde (10 mg, 0.07 mmol) dissolved in dichloromethane (0.3 mL) and acetic acid neat (4 μL, 0.06 mmol) in a 20 mL vial. After that, 115 mg of MP-cyanoborohydride resin (Biotage®, 2.17 mmol/g loading) was added, and the resulting mixture was shaken at room temperature for 4 days. The reaction mixture was filtered, and the filtrate was concentrated. The residue was dissolved in 1:1 dimethyl sulfoxide/methanol (1.4 mL) and purified by reverse phase HPLC [column: Phenomenex® Luna® AXIA™ C8(2) 5 μm 100 Å (30 mm×75 mm); eluent: acetonitrile-0.1% trifluoroacetic acid in water—10%-100% gradient] to afford the titled compound as a trifluoroacetate salt. $^1$H NMR (DMSO-$d_6$) δ ppm 1.80-1.91 (m, 3H), 2.04-2.18 (m, 3H), 3.46-3.60 (m, 3H), 4.26 (dd, J=40.4, 13.4 Hz, 1H), 4.42-4.88 (m, 4H), 6.34-6.45 (m, 1H), 6.75-6.99 (m, 3H), 7.03-7.43 (m, 7H), 7.46-7.50 (m, 1H), 7.59-7.67 (m, 1H), 7.88-8.18 (m, 1H); MS (ESI+) m/z 502 (M+H)$^+$.

Example 5

N-{4-chloro-2-[2-(trifluoromethyl)pyrimidin-4-yl]benzyl}-1-[1-(3-fluorophenyl)-5-methyl-1H-pyrazol-4-yl]-N-{[1-(1,3-thiazol-2-yl)-1H-pyrrol-2-yl]methyl}ethanamine 1-[1-(3-Fluorophenyl)-5-methyl-1H-pyrazol-4-yl]-N-{[1-(1,3-thiazol-2-yl)-1H-pyrrol-2-yl]methyl}) ethanamine oxalate (23 mg, 0.05 mmol) dissolved in dichloromethane (1.0 mL) was treated sequentially with 4-chloro-2-(2-(trifluoromethyl)pyrimidin-4-yl)benzaldehyde (20 mg, 0.07 mmol) dissolved in dichloromethane (0.3 mL) and acetic acid neat (4 μL, 0.06 mmol). After that, 115 mg of MP-cyanoborohydride resin (Biotage®, 2.17 mmol/g loading) was added, and the resulting mixture was shaken at room temperature for 4 days. The reaction was filtered, and the filtrate was concentrated. The residue was dissolved in 1:1 dimethyl sulfoxide/methanol (1.4 mL) and purified by reverse phase HPLC [column: Phenomenex® Luna® AXIA™ C8(2) 5 μm 100 Å (30 mm×75 mm); eluent: acetonitrile-0.1% trifluoroacetic acid in water—10%-100% gradient] to afford the titled compound as a trifluoroacetate salt. $^1$H NMR (DMSO-$d_6$) δ ppm 1.31-1.45 (m, 3H), 1.96 (s, 3H), 3.93-4.34 (m, 4H), 4.29-4.59 (m, 1H), 6.10-6.27 (m, 2H), 7.05-7.28 (m, 4H), 7.39-7.50 (m, 4H), 7.49-7.58 (m, 3H), 7.87 (d, J=5.3 Hz, 1H), 9.02 (d, J=5.2 Hz, 1H); MS (ESI+) m/z 652 (M+H)$^+$.

Example 6

N-{[1-(2,6-dimethylphenyl)-1H-pyrrol-3-yl]methyl}-1-[1-(3-fluorophenyl)-5-methyl-1H-pyrazol-4-yl]-N-{[1-(1,3-thiazol-2-yl)-1H-pyrrol-2-yl]methyl}ethanamine 1-[1-(3-Fluorophenyl)-5-methyl-1H-pyrazol-4-yl]-N-{[1-(1,3-thiazol-2-yl)-1H-pyrrol-2-yl]methyl}ethanamine oxalate (23 mg, 0.05 mmol) dissolved in dichloromethane (1.0 mL) was treated sequentially with 1-(2,6-dimethylphenyl)-1H-pyrrole-3-carbaldehyde (14 mg, 0.07 mmol) dissolved in dichloromethane (0.3 mL) and acetic acid neat (4 μL, 0.06 mmol). After that, 115 mg of MP-cyanoborohydride resin (Biotage®, 2.17 mmol/g loading) was added, and the resulting mixture was shaken at room temperature for 4 days. The reaction was filtered, and the filtrate was concentrated. The residue was dissolved in 1:1 dimethyl sulfoxide/methanol (1.4 mL) and purified by reverse phase HPLC [column: Phenomenex® Luna® AXIA™ C8(2) 5 μm 100 Å (30 mm×75 mm); eluent: acetonitrile-0.1% trifluoroacetic acid in water—10%-100% gradient] to give the titled compound as a trifluoroacetate salt. $^1$H NMR (DMSO-$d_6$) δ ppm 1.77 (d, J=19.1 Hz, 3H), 1.82-1.90 (m, 6H), 2.11-2.20 (m, 3H), 4.24-4.34 (m, 1H), 4.49-4.99 (m, 4H), 5.90-6.22 (m, 1H), 6.39-6.91 (m, 4H), 7.12-7.65 (m, 10H), 7.68-8.23 (m, 1H); MS (ESI+) m/z 565 (M+H)$^+$.

Example 7

1-[1-(3-fluorophenyl)-5-methyl-1H-pyrazol-4-yl]-N,N-bis[(1-methyl-5-phenyl-1H-imidazol-2-yl)methyl]ethanamine 1-[1-(3-Fluorophenyl)-5-methyl-1H-pyrazol-4-yl]ethanamine oxalate (Prepared from the compound described in Example 1, Step D using the salt preparation procedure described in Example 4, Step A; 20 mg, 0.06 mmol) dissolved in dichloromethane (1.0 mL) was combined sequentially with 1-methyl-5-phenyl-1H-imidazole-2-carbaldehyde (17 mg, 0.09 mmol) dissolved in dichloromethane (0.3 mL) and acetic acid neat (4 μL, 0.12 mmol) in a 20 mL vial. After that, 219 mg of MP-cyanoborohydride resin (Biotage®, 2.17 mmol/g loading) was added and the resulting mixture was shaken at room temperature for 4 days. The reaction was filtered, and the filtrate was concentrated. The residue was dissolved in 1:1 dimethyl sulfoxide/methanol (1.4 mL) and purified by reverse phase HPLC [column: Phenomenex® Luna® AXIA™ C8(2) 5 μm 100 Å (30 mm×75 mm); eluent: acetonitrile-0.1% trifluoroacetic acid in water—10%-100% gradient] to give the titled compound as a trifluoroacetate salt. $^1$H NMR (pyridine-$d_5$) δ ppm 1.56 (d, J=6.9 Hz, 3H), 2.16-2.22 (m, 3H), 3.22-3.27 (m, 6H), 4.01-4.07 (m, 4H), 4.42-4.53 (m, 1H), 7.00-7.08 (m, 1H), 7.18-7.24 (m, 2H), 7.25-7.44 (m, 13H), 7.90-7.95 (m, 1H); MS (ESI+) m/z 560 (M+H)$^+$.

Example 8

1-(2,4-dimethoxyphenyl)-N,N-bis{[1-(1,3,4-thiadiazol-2-yl)-1H-pyrrol-2-yl]methyl}methanamine A mixture of 1-(1,3,4-thiadiazol-2-yl)-1H-pyrrole-2-carbaldehyde (37.59 mg, 0.21 mmol), (2,4-dimethoxyphenyl)methanamine hydrochloride (11.15 mg, 0.052 mmol), acetic acid (10 equivalents, 30.02 L, 0.52 mmol) and Biotage® MP-(CN)BH3 resin (2.17 mmol/g loading, 120.85 mg, macro-porous) in 1 mL of dichloromethane/methanol (1:1) was stirred at 80° C. for 16 hours in a capped vial. After completion, the crude reaction mixture was filtered using a fritted column cartridge, and the collected material was washed twice with methanol. The filtrate and washes were then concentrated, and the residue was purified on reverse phase HPLC [column: Phenomenex® Luna® AXIA™ C8(2) 5 μm 100 Å (30 mm×75 mm); eluent: acetonitrile-0.1% trifluoroacetic acid in water—10%-100% gradient] to afford the titled compound (13.7 mg, 41.22% yield) as a trifluoroacetate salt. $^1$H NMR (400 MHz, pyridine-$d_5$) δ ppm 3.57 (s, 3H), 3.68 (s, 3H), 3.72 (s, 2H), 3.99 (s, 4H), 6.29 (t, J=3.3 Hz, 2H), 6.39 (dd, J=3.5, 1.7 Hz, 2H), 6.46 (dd, J=8.3, 2.4 Hz, 1H), 6.51 (d, J=2.4 Hz, 1H), 7.06 (d, J=8.3 Hz, 1H), 7.38-7.47 (m, 2H), 9.12 (s, 2H); MS (ESI+) m/z 491.1 (M+H)$^+$.

Example 9

1-methyl-N,N-bis{[1-(1,3,4-thiadiazol-2-yl)-1H-pyrrol-2-yl]methyl}-1H-pyrazol-5-amine The titled compound was prepared as a trifluoroacetate salt according to the procedure described for the preparation of Example 8 using 1-methyl-1H-pyrazol-5-amine instead of (2,4-dimethoxyphenyl)methanamine hydrochloride. $^1$H NMR (400 MHz, pyridine-$d_5$) δ ppm 3.24 (s, 3H), 4.50 (s, 4H), 5.84 (d, J=2.0 Hz, 1H), 6.25 (d, J=2.7 Hz, 4H), 7.24 (t, J=2.4 Hz, 2H), 7.32 (d, J=2.0 Hz, 1H), 9.23 (s, 2H); MS (ESI) m/z 424.1 (M+H)$^+$.

Example 10

1-phenyl-N,N-bis{[1-(1,3,4-thiadiazol-2-yl)-1H-pyrrol-2-yl]methyl}methanamine

The titled compound was prepared as a trifluoroacetate salt according to the procedure described for the preparation of Example 8 using phenylmethanamine hydrochloride instead of (2,4-dimethoxyphenyl)methanamine hydrochloride. $^1$H NMR (400 MHz, pyridine-$d_5$) δ ppm 3.65 (s, 2H), 3.99 (s, 4H), 6.28 (t, J=3.3 Hz, 2H), 6.35 (t, J=2.3 Hz, 2H), 7.10-7.14 (m, 2H), 7.18 (d, J=7.0 Hz, 2H), 7.31-7.38 (m, 2H), 9.17 (s, 2H); MS (ESI$^+$) m/z 434.0 (M+H)$^+$.

Example 11

1-[(1R,4S)-bicyclo[2.2.1]hept-2-yl]-N,N-bis{[1-(1,3,4-thiadiazol-2-yl)-1H-pyrrol-2-yl]methyl}methanamine The titled compound was prepared as a trifluoroacetate salt according to the procedure described for the preparation of Example 8 using rac-(1R,4S)-bicyclo[2.2.1]heptan-2-ylmethanamine hydrochloride instead of (2,4-dimethoxyphenyl)methanamine hydrochloride. $^1$H NMR (400 MHz, pyridine-$d_5$) δ ppm 0.82-0.91 (m, 1H), 0.94-1.18 (m, 4H), 1.20-1.36 (m, 2H), 1.40-1.58 (m, 1H), 1.85-2.00 (m, 2H), 2.35-2.61 (m, 2H), 3.89-4.10 (m, 4H), 6.31 (td, J=3.4, 1.5 Hz, 2H), 6.32-6.35 (m, 2H), 7.35 (q, J=2.7 Hz, 2H), 9.25 (s, 2H); MS (ESI$^+$) m/z 452.1 (M+H)$^+$.

Example 12

1-(2-methylphenyl)-N,N-bis{[1-(1,3,4-thiadiazol-2-yl)-1H-pyrrol-2-yl]methyl}methanamine The titled compound was prepared as a trifluoroacetate salt according to the procedure described for the preparation of Example 8 using o-tolylmethanamine instead of (2,4-dimethoxyphenyl)methanamine hydrochloride. $^1$H NMR (400 MHz, pyridine-$d_5$) δ ppm 1.92 (s, 3H), 3.57 (s, 2H), 3.93 (s, 4H), 6.30 (t, J=3.3 Hz, 2H), 6.39 (dd, J=3.5, 1.7 Hz, 2H), 6.96-7.01 (m, 1H), 7.07 (td, J=6.9, 1.8 Hz, 2H), 7.13 (d, J=2.2 Hz, 1H), 7.36-7.41 (m, 2H), 9.11 (s, 2H); MS (ESI) m/z 448.1 (M+H)$^+$.

Example 13

(1R)-1-(4-fluorophenyl)-N,N-bis{[1-(1,3,4-thiadiazol-2-yl)-1H-pyrrol-2-yl]methyl}ethanamine The titled compound was prepared as a trifluoroacetate salt according to the procedure described for the preparation of Example 8 using (R)-1-(4-fluorophenyl)ethanamine instead of (2,4-dimethoxyphenyl)methanamine hydrochloride. $^1$H NMR (400 MHz, pyridine-$d_5$) δ ppm 1.29 (d, J=6.9 Hz, 3H), 3.97-4.10 (m, 5H), 6.26 (t, J=3.3 Hz, 2H), 6.30-6.34 (m, 2H), 6.95 (t, J=8.7 Hz, 2H), 7.17-7.21 (m, 2H), 7.21-7.24 (m, 2H), 9.22 (s, 2H); MS (ESI$^+$) m/z 466.1 (M+H)$^+$.

Example 14

1-(3,5-dichloropyridin-2-yl)-N,N-bis{[1-(1,3,4-thiadiazol-2-yl)-1H-pyrrol-2-yl]methyl}methanamine The titled compound was prepared as a trifluoroacetate salt according to the procedure described for the preparation of Example 8 using (3,5-dichloropyridin-2-yl)methanamine instead of (2,4-dimethoxyphenyl)methanamine hydrochloride. $^1$H NMR (400 MHz, pyridine-$d_5$) δ ppm 3.94 (s, 2H), 4.19 (s, 4H), 6.27 (t, J=3.3 Hz, 2H), 6.35 (dd, J=3.5, 1.7 Hz, 2H), 7.34-7.39 (m, 2H), 7.62 (d, J=2.2 Hz, 1H), 8.37 (d, J=2.0 Hz, 1H), 9.16 (s, 2H); MS (ESI) m/z 503.0 (M+H)$^+$.

Example 15

1-(2-fluorophenyl)-N,N-bis{[1-(1,3,4-thiadiazol-2-yl)-1H-pyrrol-2-yl]methyl}methanamine The titled compound was prepared as a trifluoroacetate salt according to the procedure described for the preparation of Example 8 using (2-fluorophenyl)methanamine instead of (2,4-dimethoxyphenyl)methanamine hydrochloride. $^1$H NMR (400 MHz, pyridine-$d_5$) δ ppm 3.75 (s, 2H), 4.02 (s, 4H), 6.27 (t, J=3.2 Hz, 2H), 6.33-6.39 (m, 2H), 6.95 (td, J=9.0, 8.2, 4.4 Hz, 2H), 7.07-7.14 (m, 2H), 7.30-7.38 (m, 2H), 9.16 (s, 2H); MS (ESI) m/z 452.1 (M+H)$^+$.

Example 16

1-[1-(1,3,4-thiadiazol-2-yl)-1H-pyrrol-2-yl]-N-{[1-(1,3,4-thiadiazol-2-yl)-1H-pyrrol-2-yl]methyl}-N-[3-(trifluoromethyl)benzyl]methanamine The titled compound was prepared as a trifluoroacetate salt according to the procedure described for the preparation of Example 8 using (3-(trifluoromethyl)phenyl)methanamine instead of (2,4-dimethoxyphenyl)methanamine hydrochloride. $^1$H NMR (400 MHz, pyridine-$d_5$) δ ppm 3.70 (s, 2H), 4.05 (s, 4H), 6.26 (t, J=3.3 Hz, 2H), 6.33 (t, J=2.4 Hz, 2H), 7.24 (d, J=6.4 Hz, 2H), 7.27 (dd, J=5.1, 2.9 Hz, 2H), 7.36-7.43 (m, 2H), 9.20 (s, 2H); MS (ESI) m/z 502.0 (M+H)$^+$.

Example 17

1-(3,4-dichlorophenyl)-N,N-bis{[1-(1,3,4-thiadiazol-2-yl)-1H-pyrrol-2-yl]methyl}ethanamine The titled compound was prepared as a trifluoroacetate salt according to the procedure described for the preparation of Example 8 using 1-(3,4-dichlorophenyl)ethanamine instead of (2,4-dimethoxyphenyl)methanamine hydrochloride. $^1$H NMR (400 MHz, pyridine-$d_5$) δ ppm 4.00 (q, J=6.7 Hz, 2H), 4.06 (s, 4H), 6.26 (t, J=3.3 Hz, 2H), 6.29-6.33 (m, 2H), 7.02 (dd, J=8.4, 2.0 Hz, 1H), 7.18-7.21 (m, 2H), 7.27 (d, J=8.3 Hz, 1H), 7.31 (d, J=2.0 Hz, 1H), 9.24 (s, 2H); MS (ESI) m/z 515.9 (M+H)$^+$.

Example 18

1-(2-chlorophenyl)-N,N-bis{[1-(1,3,4-thiadiazol-2-yl)-1H-pyrrol-2-yl]methyl}methanamine The titled compound was prepared as a trifluoroacetate salt according to the procedure described for the preparation of Example 8 using (2-chlorophenyl)methanamine instead of (2,4-dimethoxyphenyl)methanamine hydrochloride. $^1$H NMR (400 MHz, pyridine-$d_5$) δ ppm 3.81 (s, 2H), 4.05 (s, 4H), 6.27 (t, J=3.2 Hz, 2H), 6.38 (d, J=3.1 Hz, 2H), 7.02-7.08 (m, 2H), 7.17-7.25 (m, 2H), 7.30-7.34 (m, 2H), 9.15 (s, 2H); MS (ESI$^+$) m/z 468.0 (M+H)$^+$.

Example 19

(1R)-1-(2-chlorophenyl)-N,N-bis{[1-(1,3,4-thiadiazol-2-yl)-1H-pyrrol-2-yl]methyl}ethanamine The titled compound was prepared as a trifluoroacetate salt according to the procedure described for the preparation of Example 8 using (R)-1-(2-chlorophenyl)ethanamine instead of (2,4-dimethoxyphenyl)methanamine hydrochloride. $^1$H NMR (400 MHz, pyridine-$d_5$) δ ppm 1.33 (d, J=7.0 Hz, 3H), 4.06 (s, 2H), 4.27 (d, J=15.2 Hz, 2H), 4.67 (d, J=6.9 Hz, 1H), 6.25 (t, J=3.3 Hz, 2H), 6.34-6.37 (m, 2H), 7.06 (dd, J=7.6, 1.7 Hz, 1H), 7.22-7.26 (m, 3H), 7.43 (d, J=7.8 Hz, 1H), 9.15 (s, 1H); MS (ESI$^+$) m/z 482.0 (M+H)$^+$.

Example 20

(1S)-1-(2-chlorophenyl)-N,N-bis{[1-(1,3,4-thiadiazol-2-yl)-1H-pyrrol-2-yl]methyl}ethanamine The titled compound was prepared as a trifluoroacetate salt according to the procedure described for the preparation of Example 8 using (S)-1-(2-chlorophenyl)ethanamine instead of (2,4-dimethoxyphenyl)methanamine hydrochloride. $^1$H NMR (400 MHz, pyridine-$d_5$) δ ppm 1.33 (d, J=7.0 Hz, 3H), 4.06 (s, 2H), 4.27 (d, J=15.3 Hz, 2H), 4.62-4.71 (m, 1H), 6.25 (t, J=3.3 Hz, 2H), 6.36 (d, J=3.1 Hz, 2H), 7.05 (t, J=7.8 Hz, 1H), 7.21-7.27 (m, 3H), 7.43 (d, J=7.8 Hz, 1H), 9.15 (s, 2H); MS (ESI$^+$) m/z 482.0 (M+H)$^+$.

Example 21

2-[1-(pyridin-2-yl)cyclopropyl]-N,N-bis{[1-(1,3,4-thiadiazol-2-yl)-1H-pyrrol-2-yl]methyl}ethanamine The titled compound was prepared as a trifluoroacetate salt according to the procedure described for the preparation of Example 8 using 2-(1-(pyridin-2-yl)cyclopropyl)ethanamine instead of (2,4-dimethoxyphenyl)methanamine hydrochloride. $^1$H NMR (400 MHz, pyridine-$d_5$) δ ppm 0.70-0.74 (m, 2H), 1.15-1.19 (m, 2H), 1.86-1.92 (m, 2H), 2.71-2.78 (m, 2H), 3.99 (s, 4H), 6.29 (t, J=3.3 Hz, 2H), 6.31-6.33 (m, 2H), 6.93 (dd, J=7.7, 5.0 Hz, 1H), 7.09 (d, J=8.0 Hz, 1H), 7.38-7.41 (m, 2H), 7.47 (td, J=7.7, 1.9 Hz, 1H), 8.46-8.49 (m, 1H), 9.19 (s, 2H); MS (ESI) m/z 489.1 (M+H)$^+$.

Example 22

N,N-bis{[1-(1,3,4-thiadiazol-2-yl)-1H-pyrrol-2-yl]methyl}aniline

The titled compound was prepared as a trifluoroacetate salt according to the procedure described for the preparation of Example 8 using aniline instead of (2,4-dimethoxyphenyl)methanamine hydrochloride. $^1$H NMR (400 MHz, pyridine-$d_5$) δ ppm 5.02 (s, 4H), 6.18-6.21 (m, 2H), 6.23 (t, J=3.3 Hz, 2H), 6.78 (t, J=7.3 Hz, 1H), 6.94 (s, 2H), 6.96 (d, J=8.2 Hz, 2H), 7.17-7.22 (m, 4H), 9.17 (s, 2H); MS (ESI$^+$) m/z 420.0 (M+H)$^+$.

Example 23

1-(4,4-difluorocyclohexyl)-N,N-bis{[1-(1,3,4-thiadiazol-2-yl)-1H-pyrrol-2-yl]methyl}methanamine The titled compound was prepared as a trifluoroacetate salt according to the procedure described for the preparation of Example 8 using (4,4-difluorocyclohexyl)methanamine instead of (2,4-dimethoxyphenyl)methanamine hydrochloride. $^1$H NMR (400 MHz, pyridine-$d_5$) δ ppm 0.92 (dt, J=12.5, 9.3 Hz, 2H), 1.35 (ddt, J=14.4, 10.8, 4.9 Hz, 1H), 1.47 (dt, J=13.2, 3.6 Hz, 2H), 1.53-1.71 (m, 2H), 1.86 (dt, J=12.9, 9.1 Hz, 2H), 2.29 (d, J=7.0 Hz, 2H), 3.99 (s, 4H), 6.31 (t, J=3.3 Hz, 2H), 6.32-6.35 (m, 2H), 7.26-7.33 (m, 2H), 9.27 (s, 2H); MS (ESI$^+$) m/z 476.1 (M+H)$^+$.

Example 24

2-[1-(pyridin-3-yl)cyclopropyl]-N,N-bis{[1-(1,3,4-thiadiazol-2-yl)-1H-pyrrol-2-yl]methyl}ethanamine The titled compound was prepared as a trifluoroacetate salt according to the procedure described for the preparation of Example 8 using 2-(1-(pyridin-3-yl)cyclopropyl)ethanamine instead of (2,4-dimethoxyphenyl)methanamine hydrochloride. $^1$H NMR (400 MHz, pyridine-$d_5$) δ ppm 0.64 (d, J=25.7 Hz, 4H), 1.54-1.66 (m, 2H), 2.52-2.61 (m, 2H), 3.88 (s, 4H), 6.22 (d, J=3.2 Hz, 2H), 6.26 (t, J=3.4 Hz, 2H), 7.10 (dd, J=7.8, 4.7 Hz, 1H), 7.33-7.37 (m, 2H), 7.41 (d, J=8.1 Hz, 1H), 8.49 (d, J=4.5 Hz, 1H), 8.60 (d, J=2.2 Hz, 1H), 9.19 (s, 2H); MS (ESI$^+$) m/z 489.1 (M+H)$^+$.

Example 25

N,N-bis{[1-(1,3,4-thiadiazol-2-yl)-1H-pyrrol-2-yl]methyl}-1-(thiophen-2-yl)propan-2-amine The titled compound was prepared as a trifluoroacetate salt according to the procedure described for the preparation of Example 8 using 1-(thiophen-2-yl)propan-2-amine instead of (2,4-dimethoxyphenyl)methanamine hydrochloride. $^1$H NMR (400 MHz, pyridine-$d_5$) δ ppm 0.95 (d, J=6.6 Hz, 3H), 2.69 (dd, J=14.5, 9.2 Hz, 1H), 3.05 (dd, J=14.4, 4.7 Hz, 1H), 3.23 (ddd, J=9.3, 6.9, 4.8 Hz, 1H), 4.11 (d, J=9.5

Hz, 4H), 6.28 (t, J=3.3 Hz, 2H), 6.31-6.34 (m, 2H), 6.71 (d, J=3.4 Hz, 1H), 6.85 (dd, J=5.2, 3.4 Hz, 1H), 7.10 (d, J=5.2 Hz, 1H), 7.25-7.30 (m, 2H), 9.22 (s, 2H) MS (ESI$^+$) m/z 468.1 (M+H)$^+$.

Example 26

1-[1-(pyridin-3-yl)cyclopropyl]-N,N-bis{[1-(1,3,4-thiadiazol-2-yl)-1H-pyrrol-2-yl]methyl}methanamine The titled compound was prepared as a trifluoroacetate salt according to the procedure described for the preparation of Example 8 using (1-(pyridin-3-yl)cyclopropyl)methanamine instead of (2,4-dimethoxyphenyl)methanamine hydrochloride. $^1$H NMR (400 MHz, pyridine-d$_5$) δ ppm 0.66 (d, J=5.2 Hz, 3H), 0.74 (d, J=4.5 Hz, 2H), 2.86 (s, 2H), 4.07 (s, 4H), 6.19 (d, J=3.2 Hz, 2H), 6.27 (t, J=3.3 Hz, 2H), 7.01 (dd, J=7.8, 4.7 Hz, 1H), 7.27-7.30 (m, 2H), 7.30 (d, J=1.9 Hz, 1H), 7.32 (q, J=3.5, 2.8 Hz, 1H), 8.41 (d, J=5.2 Hz, 1H), 8.50 (d, J=2.2 Hz, 1H), 9.16 (s, 2H); MS (ESI$^+$) m/z 475.0 (M+H)$^+$.

Example 27

2-[1-(pyridin-4-yl)cyclopropyl]-N,N-bis{[1-(1,3,4-thiadiazol-2-yl)-1H-pyrrol-2-yl]methyl}ethanamine The titled compound was prepared as a trifluoroacetate salt according to the procedure described for the preparation of Example 8 using 2-(1-(pyridin-4-yl)cyclopropyl)ethanamine instead of (2,4-dimethoxyphenyl)methanamine hydrochloride. $^1$H NMR (400 MHz, pyridine-d$_5$) δ ppm 0.67 (d, J=4.3 Hz, 2H), 0.72 (d, J=4.1 Hz, 2H), 1.60-1.68 (m, 2H), 2.52-2.61 (m, 2H), 3.93 (s, 4H), 6.27 (dd, J=7.2, 3.2 Hz, 4H), 6.99 (d, J=5.4 Hz, 2H), 7.35 (s, 2H), 7.34-7.40 (m, 2H), 8.54 (d, J=5.3 Hz, 2H), 9.21 (s, 2H); MS (ESI$^+$) m/z 489.1 (M+H)$^+$.

Example 28

4-[(bis{[1-(1,3,4-thiadiazol-2-yl)-1H-pyrrol-2-yl]methyl}amino)methyl]thiophene-2-carbonitrile The titled compound was prepared as a trifluoroacetate salt according to the procedure described for the preparation of Example 8 using 4-(aminomethyl)thiophene-2-carbonitrile instead of (2,4-dimethoxyphenyl)methanamine hydrochloride. $^1$H NMR (400 MHz, pyridine-d$_5$) δ ppm 3.61 (s, 2H), 4.00 (s, 4H), 6.28 (t, J=3.3 Hz, 2H), 6.32 (t, J=2.4 Hz, 2H), 7.26-7.30 (m, 4H), 9.23 (s, 2H); MS (ESI$^+$) m/z 465.0 (M+H)$^+$.

Example 29

1-(2,4-dichlorophenyl)-N,N-bis{[1-(1,3-thiazol-2-yl)-1H-pyrrol-2-yl]methyl}methanamine The titled compound was prepared as a trifluoroacetate salt according to the procedure described for the preparation of Example 8 using (2,4-dichlorophenyl)methanamine instead of (2,4-dimethoxyphenyl)methanamine hydrochloride and 1-(thiazol-2-yl)-1H-pyrrole-2-carbaldehyde (Aldrich) instead of 1-(1,3,4-thiadiazol-2-yl)-1H-pyrrole-2-carbaldehyde. $^1$H NMR (400 MHz, pyridine-d$_5$) δ ppm 3.78 (s, 2H), 4.14 (s, 4H), 6.23 (t, J=3.3 Hz, 2H), 6.34 (dd, J=3.5, 1.7 Hz, 2H), 7.05 (dd, J=8.4, 2.1 Hz, 1H), 7.13 (d, J=3.6 Hz, 2H), 7.19-7.22 (m, 2H), 7.27 (d, J=2.1 Hz, 1H), 7.45 (d, J=3.5 Hz, 2H); MS (ESI$^+$) m/z 499.9 (M+H)$^+$.

Example 30

1-(2,4-dimethoxyphenyl)-N,N-bis{[1-(1,3-thiazol-2-yl)-1H-pyrrol-2-yl]methyl}methanamine The titled compound was prepared as a trifluoroacetate salt according to the procedure described for the preparation of Example 8 using (2,4-dimethoxyphenyl)methanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-d$_5$) δ ppm 3.57 (s, 3H), 3.90 (s, 2H), 4.22 (s, 4H), 6.27 (t, J=3.3 Hz, 2H), 6.42-6.45 (m, 2H), 6.45-6.54 (m, 3H), 7.10 (d, J=3.5 Hz, 2H), 7.19 (d, J=8.3 Hz, 1H), 7.27-7.31 (m, 2H), 7.40 (d, J=3.5 Hz, 2H); MS (ESI$^+$) m/z 492.1 (M+H)$^+$.

Example 31

1-phenyl-N,N-bis{[1-(1,3-thiazol-2-yl)-1H-pyrrol-2-yl]methyl}methanamine

The titled compound was prepared as a trifluoroacetate salt according to the procedure described for the preparation of Example 8 using benzylamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-d$_5$) δ ppm 3.74 (s, 2H), 4.13 (s, 4H), 6.25 (t, J=3.2 Hz, 2H), 6.37 (dd, J=3.3, 1.7 Hz, 2H), 7.12 (d, J=3.5 Hz, 2H), 7.19 (d, J=4.3 Hz, 3H), 7.23-7.26 (m, 2H), 7.46 (d, J=3.6 Hz, 2H); MS (ESI$^+$) m/z 432.1 (M+H)$^+$.

Example 32

1-[(1R,4S)-bicyclo[2.2.1]hept-2-yl]-N,N-bis{[1-(1,3-thiazol-2-yl)-1H-pyrrol-2-yl]methyl}methanamine The titled compound was prepared as a trifluoroacetate salt according to the procedure described for the preparation of Example 8 using rac-(1R,4S)-bicyclo[2.2.1]heptan-2-ylmethanamine hydrochloride instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-d$_5$) δ ppm 0.78-0.95 (m, 2H), 0.97-1.08 (m, 2H), 1.09-1.24 (m, 3H), 1.34 (td, J=7.6, 3.6 Hz, 2H), 1.47-1.60 (m, 1H), 1.95-2.07 (m, 2H), 2.61 (d, J=6.5 Hz, 1H), 4.15 (dd, J=14.6, 5.4 Hz, 2H), 4.23 (dd, J=18.0, 14.5 Hz, 2H), 6.28 (q, J=3.0 Hz, 2H), 6.35-6.41 (m, 2H), 7.20 (dd, J=3.5, 2.0 Hz, 2H), 7.26 (q, J=2.4 Hz, 2H), 7.50 (t, J=4.3 Hz, 2H); MS (ESI$^+$) m/z 450.1 (M+H)$^+$.

Example 33

1-(tetrahydrofuran-2-yl)-N,N-bis{[1-(1,3-thiazol-2-yl)-1H-pyrrol-2-yl]methyl}methanamine The titled compound was prepared as a trifluoroacetate salt according to the procedure described for the preparation of Example 8 using (tetrahydrofuran-2-yl)methanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-$d_5$) δ ppm 1.25 (dt, J=7.2, 3.6 Hz, 1H), 1.58 (p, J=7.3 Hz, 2H), 1.62-1.72 (m, 1H), 2.76-2.81 (m, 2H), 3.56 (q, J=7.3 Hz, 1H), 3.68 (q, J=7.1 Hz, 1H), 3.98 (p, J=6.4 Hz, 1H), 4.16 (d, J=14.7 Hz, 2H), 4.32 (d, J=14.6 Hz, 2H), 6.26 (t, J=3.2 Hz, 2H), 6.35-6.39 (m, 2H), 7.26-7.30 (m, 2H), 7.50 (d, J=3.6 Hz, 2H); MS (ESI$^+$) m/z 426.1 (M+H)$^+$.

Example 34

1-[1-(1,3-thiazol-2-yl)-1H-pyrrol-2-yl]-N-{[1-(1,3-thiazol-2-yl)-1H-pyrrol-2-yl]methyl}-N-[4-(trifluoromethyl)benzyl]methanamine The titled compound was prepared as a trifluoroacetate salt according to the procedure described for the preparation of Example 8 using (4-(trifluoromethyl)phenyl)methanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-$d_5$) δ ppm 3.69 (s, 2H), 4.11 (s, 4H), 6.25 (t, J=3.2 Hz, 2H), 6.33 (dd, J=3.4, 1.7 Hz, 2H), 7.18 (s, 1H), 7.20-7.23 (m, 3H), 7.44 (d, J=8.0 Hz, 2H), 7.47 (d, J=3.5 Hz, 1H); MS (ESI$^+$) m/z 500.0 (M+H)$^+$.

Example 35

3-methyl-1-phenyl-N,N-bis{[1-(1,3-thiazol-2-yl)-1H-pyrrol-2-yl]methyl}-1H-pyrazol-5-amine The titled compound was prepared as a trifluoroacetate salt according to the procedure described for the preparation of Example 8 using 3-methyl-1-phenyl-1H-pyrazol-5-amine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-$d_5$) δ ppm 2.17 (s, 3H), 4.09 (s, 2H), 4.28 (s, 2H), 5.95 (d, J=3.3 Hz, 1H), 5.98-6.03 (m, 1H), 6.14 (t, J=3.3 Hz, 1H), 6.22 (t, J=3.3 Hz, 1H), 7.01 (d, J=3.6 Hz, 2H), 7.16-7.22 (m, 3H), 7.32 (d, J=3.7 Hz, 1H), 7.34-7.39 (m, 3H), 7.59 (d, J=3.6 Hz, 1H), 7.91 (d, J=7.9 Hz, 2H); MS (ESI$^+$) m/z 498.1 (M+H)$^+$.

Example 36

1-(2,6-dichlorophenyl)-N,N-bis{[1-(1,3-thiazol-2-yl)-1H-pyrrol-2-yl]methyl}methanamine The titled compound was synthesized as a trifluoroacetate salt according to the procedure described for the preparation of Example 8 using (2,6-dichlorophenyl)methanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-$d_5$) δ ppm 3.93 (d, J=1.8 Hz, 2H), 4.11 (d, J=1.6 Hz, 4H), 6.25 (t, J=3.3 Hz, 2H), 6.36 (dd, J=3.5, 1.7 Hz, 2H), 6.99-7.04 (m, 3H), 7.18 (d, J=8.0 Hz, 2H), 7.25-7.28 (m, 2H), 7.34 (d, J=3.5 Hz, 2H); MS (ESI$^+$) m/z 500.0 (M+H)$^+$.

Example 37

1-(2-methylphenyl)-N,N-bis{[1-(1,3-thiazol-2-yl)-1H-pyrrol-2-yl]methyl}methanamine The titled compound was synthesized as a trifluoroacetate salt according to the procedure described for the preparation of Example 8 using o-tolylmethanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-$d_5$) δ ppm 1.98 (d, J=1.8 Hz, 3H), 3.65 (s, 2H), 4.08 (s, 4H), 6.26 (t, J=3.2 Hz, 2H), 6.37 (dd, J=3.5, 1.7 Hz, 2H), 7.00 (dd, J=6.6, 2.2 Hz, 1H), 7.03-7.11 (m, 4H), 7.21-7.28 (m, 3H), 7.41 (d, J=3.5 Hz, 2H); MS (ESI$^+$) m/z 446.1 (M+H)$^+$.

Example 38

1-(3,5-dichloropyridin-2-yl)-N,N-bis{[1-(1,3-thiazol-2-yl)-1H-pyrrol-2-yl]methyl}methanamine The titled compound was prepared as a trifluoroacetate salt according to the procedure described for the preparation of Example 8 using (3,5-dichloropyridin-2-yl)methanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-$d_5$) δ ppm 3.99 (s, 2H), 4.27 (s, 4H), 6.24 (t, J=3.3 Hz, 2H), 6.31-6.40 (m, 2H), 7.09 (d, J=3.5 Hz, 2H), 7.25-7.29 (m, 2H), 7.44 (d, J=3.6 Hz, 2H), 7.61 (d, J=2.2 Hz, 1H), 8.36 (d, J=2.1 Hz, 1H); MS (ESI$^+$) m/z 501.0 (M+H)$^+$.

Example 39

2-methyl-N,N-bis{[1-(1,3-thiazol-2-yl)-1H-pyrrol-2-yl]methyl}propan-1-amine

The titled compound was prepared as a trifluoroacetate salt according to the procedure described for the preparation of Example 8 using isobutylamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-$d_5$) δ ppm 0.65-0.69 (m, 6H), 1.60 (dp, J=13.4, 6.7 Hz, 1H), 2.34 (d, J=7.1 Hz, 2H), 4.13 (s, 4H), 6.27 (t, J=3.2 Hz, 2H), 6.35 (dd, J=3.5, 1.7 Hz, 2H), 7.18 (d, J=3.6 Hz, 2H), 7.24-7.26 (m, 2H), 7.51 (s, 2H); MS (ESI$^+$) m/z 398.1 (M+H)$^+$.

Example 40

1-(2-fluorophenyl)-N,N-bis{[1-(1,3-thiazol-2-yl)-1H-pyrrol-2-yl]methyl}methanamine The titled compound was prepared as a trifluoroacetate salt according to the procedure described for the preparation of Example 8 using (2-fluorophenyl)methanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-$d_5$) δ ppm 3.81 (s, 2H), 4.12 (s, 4H), 6.24 (t, J=3.3 Hz, 2H), 6.33-6.37 (m, 2H), 6.90-6.98 (m, 2H), 7.10 (d, J=3.5 Hz, 2H), 7.23 (dd, J=3.1, 1.7 Hz, 3H), 7.46 (d, J=3.6 Hz, 2H); MS (ESI) m/z 450.1 (M+H)$^+$.

Example 41

1-[1-(3-fluorophenyl)-5-methyl-1H-pyrazol-4-yl]-N-[(1-methyl-5-phenyl-1H-imidazol-2-yl)methyl]-N-{[1-(1,3-thiazol-2-yl)-1H-pyrrol-2-yl]methyl}ethanamine The titled compound was prepared as a trifluoroacetate salt according to the procedure described for the preparation of Example 5 using 1-methyl-4-phenyl-1H-imidazole-2-carbaldehyde instead of 4-chloro-2-(2-(trifluoromethyl)pyrimidin-4-yl)benzaldehyde. $^1$H NMR (pyridine-$d_5$) δ ppm 1.42 (d, J=6.9 Hz, 3H), 2.09 (s, 3H), 2.39-2.47 (m, 2H), 3.13 (s, 3H), 4.04-4.42 (m, 1H), 6.27-6.42 (m, 2H), 6.94 (s, 2H), 7.00-7.08 (m, 2H), 7.29-7.41 (m, 9H), 7.72 (s, 1H); MS (ESI$^+$) m/z 552 (M+H)$^+$.

Example 42

1-(2,4-dichlorophenyl)-N,N-bis{[1-(1,3,4-thiadiazol-2-yl)-1H-pyrrol-2-yl]methyl}methanamine The titled compound was prepared as a trifluoroacetate salt according to the procedure described for the preparation of Example 8 using (2,4-dichlorophenyl)methanamine instead of (2,4-dimethoxyphenyl)methanamine hydrochloride. $^1$H NMR (400 MHz, pyridine-$d_5$) δ ppm 3.74 (s, 2H), 4.06 (s, 4H), 6.27 (t, J=3.3 Hz, 2H), 6.33-6.39 (m, 2H), 7.05-7.09 (m, 2H), 7.25-7.31 (m, 3H), 9.20 (s, 2H); MS (ESI$^+$) m/z 502.0 (M+H)$^+$.

Example 43

1-(4-fluorophenyl)-3-methyl-N,N-bis{[1-(1,3,4-thiadiazol-2-yl)-1H-pyrrol-2-yl]methyl}-1H-pyrazol-5-amine The titled compound was prepared as a trifluoroacetate salt according to the procedure described for the preparation of Example 8 using 1-(4-fluorophenyl)-3-methyl-1H-pyrazol-5-amine instead of (2,4-dimethoxyphenyl)methanamine hydrochloride. $^1$H NMR (400 MHz, pyridine-$d_5$) δ ppm 2.16 (s, 3H), 4.56 (s, 4H), 5.79 (s, 1H), 6.24 (dd, J=7.2, 4.1 Hz, 4H), 6.88-6.96 (m, 3H), 7.34-7.40 (m, 3H), 9.24 (s, 2H); MS (ESI$^+$) m/z 518.1 (M+H)$^+$.

Example 44

1-[1-(1,3-thiazol-2-yl)-1H-pyrrol-2-yl]-N-{[1-(1,3-thiazol-2-yl)-1H-pyrrol-2-yl]methyl}-N-[3-(trifluoromethyl)benzyl]methanamine The titled compound was prepared as a trifluoroacetate salt according to the procedure described for the preparation of Example 8 using (3-(trifluoromethyl)phenyl)methanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-$d_5$) δ ppm 3.70 (s, 2H), 4.11 (s, 4H), 6.23 (t, J=3.2 Hz, 2H), 6.31 (dd, J=3.5, 1.7 Hz, 2H), 7.13 (d, J=3.5 Hz, 2H), 7.20-7.22 (m, 2H), 7.23-7.29 (m, 2H), 7.41 (d, J=7.2 Hz, 1H), 7.45 (s, 1H), 7.47 (d, J=3.6 Hz, 2H); MS (ESI$^+$) m/z 500.1 (M+H)$^+$.

Example 45

4-[(bis{[1-(1,3-thiazol-2-yl)-1H-pyrrol-2-yl]methyl}amino)methyl]benzonitrile

The titled compound was synthesized according to the procedure described for the preparation of Example 8 using 4-(aminomethyl)benzonitrile instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-$d_5$) δ ppm 3.66 (s, 2H), 4.09 (s, 4H), 6.20-6.25 (m, 2H), 6.30 (t, J=2.4 Hz, 2H), 7.11 (d, J=7.7 Hz, 3H), 7.16 (d, J=3.5 Hz, 2H), 7.19-7.22 (m, 2H), 7.40 (d, J=8.1 Hz, 2H), 7.48 (d, J=3.6 Hz, 2H); MS (ESI$^+$) m/z 457.1 (M+H)$^+$.

Example 46

1-(3,4-dichlorophenyl)-N,N-bis{[1-(1,3-thiazol-2-yl)-1H-pyrrol-2-yl]methyl}ethanamine The titled compound was prepared as a trifluoroacetate salt according to the procedure described for the preparation of Example 8 using 1-(3,4-dichlorophenyl)ethanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-$d_5$) δ ppm 1.27 (d, J=6.9 Hz, 3H), 4.01 (q, J=6.8 Hz, 1H), 4.05-4.17 (m, 4H), 6.23 (t, J=3.2 Hz, 2H), 6.29-6.34 (m, 2H), 7.04 (dd, J=8.4, 2.0 Hz, 1H), 7.17 (d, J=3.6 Hz, 2H), 7.26 (d, J=8.3 Hz, 1H), 7.35 (d, J=2.0 Hz, 1H), 7.50 (d, J=3.6 Hz, 2H); MS (ESI$^+$) m/z 514.0 (M+H)$^+$.

Example 47

1-(2-chlorophenyl)-N,N-bis{[1-(1,3-thiazol-2-yl)-1H-pyrrol-2-yl]methyl}methanamine The titled compound was prepared as a trifluoroacetate salt according to the procedure described for the preparation of Example 8 using (2-chlorophenyl)methanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-$d_5$) δ ppm 3.88 (s, 2H), 4.17 (s, 4H), 6.23 (t, J=3.2 Hz, 2H), 6.37 (dd, J=3.4, 1.6 Hz, 2H), 7.04 (tt, J=7.4, 5.4 Hz, 2H), 7.10 (d, J=3.6 Hz, 2H), 7.21-7.25 (m, 3H), 7.31 (dd, J=7.0, 2.3 Hz, 1H), 7.44 (d, J=3.5 Hz, 2H); MS (ESI$^+$) m/z 466.1 (M+H)$^+$.

Example 48

(1R)-1-(2-chlorophenyl)-N,N-bis{[1-(1,3-thiazol-2-yl)-1H-pyrrol-2-yl]methyl}ethanamine The titled compound was prepared as a trifluoroacetate salt according to the procedure described for the preparation of Example 8 using (R)-1-(2-chlorophenyl)ethanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-$d_5$) δ ppm 1.34 (d, J=6.9 Hz, 3H), 4.17 (d, J=15.2 Hz, 2H), 4.39 (d, J=15.2 Hz, 2H), 4.71 (q, J=6.9 Hz, 1H), 6.22 (t, J=3.3 Hz, 2H), 6.33-6.41 (m, 2H), 7.04 (td, J=7.6, 1.7 Hz, 1H), 7.10 (d, J=3.5 Hz, 2H), 7.14 (s, 3H), 7.25 (d, J=7.9 Hz, 1H), 7.44-7.50 (m, 3H); MS (ESI$^+$) m/z 480.1 (M+H)$^+$.

Example 49

(1S)-1-(2-chlorophenyl)-N,N-bis{[1-(1,3-thiazol-2-yl)-1H-pyrrol-2-yl]methyl}ethanamine The titled compound was prepared as a trifluoroacetate salt according to the procedure described for the preparation of Example 8 using (S)-1-(2-chlorophenyl)ethanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-d$_5$) δ ppm 1.34 (d, J=6.9 Hz, 3H), 4.17 (d, J=15.3 Hz, 2H), 4.39 (d, J=15.3 Hz, 2H), 4.71 (q, J=6.9 Hz, 1H), 6.22 (t, J=3.3 Hz, 2H), 6.37 (dd, J=3.4, 1.7 Hz, 2H), 7.04 (td, J=7.6, 1.8 Hz, 1H), 7.09-7.12 (m, 2H), 7.14 (s, 3H), 7.25 (dd, J=7.9, 1.3 Hz, 1H), 7.45 (d, J=3.6 Hz, 2H), 7.48 (dd, J=7.8, 1.8 Hz, 1H); MS (ESI) m/z 480.0 (M+H)$^+$.

Example 50

N,N-bis{[1-(1,3-thiazol-2-yl)-1H-pyrrol-2-yl]methyl}pyridazin-3-amine

The titled compound was prepared as a trifluoroacetate salt according to the procedure described for the preparation of Example 8 using pyridazin-3-ylmethanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-d$_5$) δ ppm 5.11 (s, 4H), 6.23 (t, J=3.3 Hz, 2H), 6.45 (dd, J=2.9, 1.5 Hz, 2H), 6.77 (d, J=8.6 Hz, 2H), 6.99 (dd, J=9.0, 4.4 Hz, 2H), 7.10 (d, J=3.6 Hz, 2H), 7.17 (d, J=1.9 Hz, 2H), 7.48 (d, J=3.6 Hz, 2H), 8.57 (d, J=4.3 Hz, 2H); MS (ESI$^+$) m/z (M+H)$^+$.

Example 51

2-[1-(pyridin-2-yl)cyclopropyl]-N,N-bis{[1-(1,3-thiazol-2-yl)-1H-pyrrol-2-yl]methyl}ethanamine The titled compound was prepared as a trifluoroacetate salt according to the procedure described for the preparation of Example 8 using 2-(1-(pyridin-2-yl)cyclopropyl)ethanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-d$_5$) δ ppm 0.72-0.76 (m, 2H), 1.14-1.18 (m, 2H), 1.96-2.02 (m, 2H), 2.89-2.96 (m, 2H), 4.23 (s, 4H), 6.26 (t, J=3.3 Hz, 2H), 6.39 (dd, J=3.3, 1.7 Hz, 2H), 6.93 (dd, J=7.4, 4.8 Hz, 1H), 7.07 (d, J=8.0 Hz, 1H), 7.15 (s, 2H), 7.16 (s, 1H), 7.29 (dd, J=3.1, 1.7 Hz, 2H), 7.45-7.48 (m, 2H), 8.44 (dd, J=4.9, 1.8 Hz, 1H); MS (ESI$^+$) m/z 487.1 (M+H)$^+$.

Example 52

N,N-bis{[1-(1,3-thiazol-2-yl)-1H-pyrrol-2-yl]methyl}cyclohexanamine

The titled compound was prepared as a trifluoroacetate salt according to the procedure described for the preparation of Example 8 using cyclohexylamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-d$_5$) δ ppm 1.02 (dq, J=24.9, 12.4 Hz, 3H), 1.26 (td, J=13.1, 10.1 Hz, 2H), 1.46 (d, J=12.1 Hz, 1H), 1.60-1.77 (m, 4H), 1.75 (s, 1H), 2.73 (s, 1H), 4.21 (s, 4H), 6.25 (t, J=3.3 Hz, 2H), 6.32-6.40 (m, 2H), 7.18 (d, J=3.6 Hz, 2H), 7.20-7.22 (m, 2H), 7.51-7.52 (s, 2H); MS (ESI$^+$) m/z 424.1 (M+H)$^+$.

Example 53

N,N-bis{[1-(1,3-thiazol-2-yl)-1H-pyrrol-2-yl]methyl}aniline

The titled compound was prepared as a trifluoroacetate salt according to the procedure described for the preparation of Example 8 using aniline instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-d$_5$) δ ppm 5.06 (s, 4H), 6.19 (d, J=3.0 Hz, 4H), 6.74 (t, J=7.3 Hz, 1H), 6.96 (d, J=8.3 Hz, 2H), 7.09 (d, J=3.6 Hz, 2H), 7.16-7.20 (m, 4H), 7.49 (d, J=3.6 Hz, 2H); MS (ESI$^+$) m/z 418.0 (M+H)$^+$.

Example 54

1-[1-(1,3,4-thiadiazol-2-yl)-1H-pyrrol-2-yl]-N-{[1-(1,3,4-thiadiazol-2-yl)-1H-pyrrol-2-yl]methyl}-N-[4-(trifluoromethyl)benzyl]methanamine The titled compound was prepared as a trifluoroacetate salt according to the procedure described for the preparation of Example 8 using (4-(trifluoromethyl)phenyl)methanamine instead of (2,4-dimethoxyphenyl)methanamine hydrochloride. $^1$H NMR (400 MHz, pyridine-d$_5$) δ ppm 3.68 (s, 2H), 4.04 (s, 4H), 6.28 (t, J=3.2 Hz, 2H), 6.32-6.38 (m, 2H), 7.17 (s, 1H), 7.26-7.31 (m, 2H), 7.45 (d, J=7.9 Hz, 2H), 9.21 (s, 2H); MS (ESI$^+$) m/z 502.0 (M+H)$^+$.

Example 55

1-(2,6-dichlorophenyl)-N,N-bis{[1-(1,3,4-thiadiazol-2-yl)-1H-pyrrol-2-yl]methyl}methanamine The titled compound was prepared as a trifluoroacetate salt according to the procedure described for the preparation of Example 8 using (2,6-dichlorophenyl)methanamine instead of (2,4-dimethoxyphenyl)methanamine hydrochloride. $^1$H NMR (400 MHz, pyridine-d$_5$) δ ppm 3.98 (m, 6H) 6.41 (q, J=2.6 Hz, 2H), 7.21 (dt, J=3.3, 1.6 Hz, 2H), 7.75 (d, J=2.7 Hz, 2H), 9.39 (s, 2H), 9.89 (d, J=1.6 Hz, 2H); MS (ESI$^+$) m/z (M+H)$^+$.

Example 56

4-[(bis{[1-(1,3,4-thiadiazol-2-yl)-1H-pyrrol-2-yl]methyl}amino)methyl]benzonitrile The titled compound was prepared as a trifluoroacetate salt according to the procedure described for the preparation of Example 8 using 4-(aminomethyl)benzonitrile instead of (2,4-dimethoxyphenyl)methanamine hydrochloride. $^1$H NMR (400 MHz, pyridine-d$_5$) δ ppm 3.65 (s, 2H), 4.03 (s, 4H), 6.26 (t, J=3.3 Hz, 2H), 6.33 (d, J=3.2 Hz, 2H), 7.08 (d, J=7.7 Hz, 2H), 7.23-7.30 (m, 2H), 7.41 (d, J=7.7 Hz, 2H), 9.24 (s, 1H); MS (ESI$^+$) m/z 459.1 (M+H)$^+$.

Example 57

1-(4,4-difluorocyclohexyl)-N,N-bis{[1-(1,3-thiazol-2-yl)-1H-pyrrol-2-yl]methyl}methanamine The titled compound was prepared as a trifluoroacetate salt according to the procedure described for the preparation of Example 8 using (4,4-difluorocyclohexyl)methanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-d$_5$) δ ppm 0.89-1.02 (m, 2H), 1.26 (dd, J=10.6, 5.8 Hz, 1H), 1.52 (dp, J=13.2, 4.7 Hz, 3H), 1.60 (q, J=4.7, 3.9 Hz, 1H), 1.86 (qd, J=12.2, 11.5, 7.1 Hz, 2H), 2.33 (dd, J=7.1, 1.7 Hz, 2H), 4.06 (s, 4H), 6.27 (t, J=3.3

Hz, 2H), 6.29-6.32 (m, 2H), 7.21 (d, J=3.6 Hz, 2H), 7.22-7.25 (m, 2H), 7.56 (d, J=3.5 Hz, 2H); MS (ESI⁺) m/z 474.1 (M+H)⁺.

Example 58

1-[1-(1,3-thiazol-2-yl)-1H-pyrrol-2-yl]-N-{[1-(1,3-thiazol-2-yl)-1H-pyrrol-2-yl]methyl}-N-{[1-(2,2,2-trifluoroethyl)-1H-pyrazol-4-yl]methyl}methanamine The titled compound was prepared as a trifluoroacetate salt according to the procedure described for the preparation of Example 8 using (1-(2,2,2-trifluoroethyl)-1H-pyrazol-4-yl)methanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. ¹H NMR (400 MHz, pyridine-d₅) δ ppm 3.65 (s, 2H), 4.07 (s, 4H), 4.93 (q, J=8.8 Hz, 2H), 6.25 (t, J=3.3 Hz, 2H), 6.29-6.32 (m, 2H), 7.12 (d, J=3.5 Hz, 2H), 7.27-7.29 (m, 2H), 7.48 (s, 1H), 7.50 (d, J=3.3 Hz, 3H); MS (ESI⁺) m/z 504.1 (M+H)⁺.

Example 59

1-[1-(difluoromethyl)-1H-imidazol-2-yl]-N,N-bis{[1-(1,3-thiazol-2-yl)-1H-pyrrol-2-yl]methyl}methanamine The titled compound was prepared as a trifluoroacetate salt according to the procedure described for the preparation of Example 8 using (1-(difluoromethyl)-1H-imidazol-2-yl)methanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. ¹H NMR (400 MHz, pyridine-d₅) δ ppm 3.92 (s, 2H), 4.12 (s, 4H), 6.25 (t, J=3.3 Hz, 2H), 6.34 (dd, J=3.4, 1.7 Hz, 2H), 7.06 (d, J=1.5 Hz, 1H), 7.12 (d, J=3.6 Hz, 2H), 7.22-7.24 (m, 2H), 7.27 (d, J=1.6 Hz, 1H), 7.47 (d, J=3.5 Hz, 2H); MS (ESI⁺) m/z 472.1 (M+H)⁺.

Example 60

2-[1-(pyridin-3-yl)cyclopropyl]-N,N-bis{[1-(1,3-thiazol-2-yl)-1H-pyrrol-2-yl]methyl}ethanamine The titled compound was prepared as a trifluoroacetate salt according to the procedure described for the preparation of Example 8 using 2-(1-(pyridin-3-yl)cyclopropyl)ethanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. ¹H NMR (400 MHz, pyridine-d₅) δ ppm 0.58-0.64 (m, 2H), 0.65-0.71 (m, 2H), 1.61-1.72 (m, 2H), 2.62-2.68 (m, 2H), 4.04 (s, 4H), 6.20-6.26 (m, 4H), 7.06-7.12 (m, 1H), 7.14 (s, 1H), 7.24-7.28 (m, 2H), 7.41 (dt, J=7.8, 2.0 Hz, 1H), 7.49 (d, J=3.5 Hz, 2H), 8.60 (d, J=2.2 Hz, 1H); MS (ESI⁺) m/z 487.1 (M+H)⁺.

Example 61

1-[(3R)-tetrahydrofuran-3-yl]-N,N-bis{[1-(1,3,4-thiadiazol-2-yl)-1H-pyrrol-2-yl]methyl}methanamine The titled compound was prepared as a trifluoroacetate salt according to the procedure described for the preparation of Example 8 using (R)-(tetrahydrofuran-3-yl)methanamine instead of (2,4-dimethoxyphenyl)methanamine hydrochloride. ¹H NMR (400 MHz, pyridine-d₅) δ ppm 1.21 (dq, J=13.5, 7.0 Hz, 1H), 1.67 (dq, J=13.5, 7.0 Hz, 1H), 2.25 (p, J=6.9 Hz, 1H), 2.46 (t, J=6.4 Hz, 2H), 3.18 (dd, J=8.3, 6.0 Hz, 1H), 3.60 (dt, J=36.0, 7.7 Hz, 3H), 3.99 (s, 4H), 6.21-6.36 (m, 4H), 7.32 (t, J=2.3 Hz, 2H), 9.24 (s, 2H); MS (ESI⁺) m/z 428.1 (M+H)⁺.

Example 62

(1R)-1-(4-fluorophenyl)-N,N-bis{[1-(1,3-thiazol-2-yl)-1H-pyrrol-2-yl]methyl}ethanamine The titled compound was prepared as a trifluoroacetate salt according to the procedure described for the preparation of Example 8 using (R)-1-(4-fluorophenyl)ethanamine instead of (2,4-dimethoxyphenyl)methanamine hydrochloride. ¹H NMR (400 MHz, pyridine-d₅) δ ppm 1.30 (d, J=6.9 Hz, 3H), 4.05-4.18 (m, 6H), 6.24 (t, J=3.2 Hz, 2H), 6.32-6.38 (m, 2H), 6.94 (t, J=8.8 Hz, 2H), 7.15-7.17 (m, 3H), 7.23 (dd, J=8.5, 5.7 Hz, 2H), 7.50 (s, 1H); MS (ESI⁺) m/z 464.1 (M+H)⁺.

Example 63

1-(furan-2-yl)-N,N-bis{[1-(1,3-thiazol-2-yl)-1H-pyrrol-2-yl]methyl}methanamine

The titled compound was prepared as a trifluoroacetate salt according to the procedure described for the preparation of Example 8 using furan-2-ylmethanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. ¹H NMR (400 MHz, pyridine-d₅) δ ppm 3.76 (s, 2H), 4.08 (s, 4H), 6.15 (d, J=3.1 Hz, 1H), 6.26 (t, J=3.3 Hz, 2H), 6.28-6.30 (m, 1H), 6.33-6.36 (m, 2H), 7.09 (d, J=3.6 Hz, 2H), 7.30-7.34 (m, 2H), 7.39 (d, J=1.8 Hz, 1H), 7.49 (d, J=3.6 Hz, 2H); MS (ESI⁺) m/z 422.1 (M+H)⁺.

Example 64

N,N-bis{[1-(1,3-thiazol-2-yl)-1H-pyrrol-2-yl]methyl}-1-(thiophen-2-yl)propan-2-amine The titled compound was prepared as a trifluoroacetate salt according to the procedure described for the preparation of Example 8 using 1-(thiophen-2-yl)propan-2-amine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. ¹H NMR (400 MHz, pyridine-d₅) δ ppm 0.98 (d, J=6.7 Hz, 3H), 2.72 (dd, J=14.4, 9.4 Hz, 1H), 3.09 (dd, J=14.4, 4.6 Hz, 1H), 3.23-3.34 (m, 1H), 4.13-4.25 (m, 4H), 6.25 (t, J=3.3 Hz, 2H), 6.33 (dd, J=3.3, 1.7 Hz, 2H), 6.72 (d, J=3.3 Hz, 1H), 6.86 (dd, J=5.1, 3.5 Hz, 1H), 7.11 (d, J=4.9 Hz, 1H), 7.16 (d, J=3.5 Hz, 2H), 7.19-7.22 (m, 2H), 7.54 (d, J=3.6 Hz, 2H); MS (ESI⁺) m/z 466.1 (M+H)⁺.

Example 65

1-[1-(pyridin-3-yl)cyclopropyl]-N,N-bis{[1-(1,3-thiazol-2-yl)-1H-pyrrol-2-yl]methyl}methanamine The titled compound was prepared as a trifluoroacetate salt according to the procedure described for the preparation of Example 8 using (1-(pyridin-3-yl)cyclopropyl)methanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-d$_5$) δ ppm 0.64-0.69 (m, 2H), 0.70-0.76 (m, 2H), 2.91 (s, 2H), 4.16 (s, 4H), 6.15-6.20 (m, 2H), 6.23 (t, J=3.3 Hz, 2H), 7.03 (dd, J=7.9, 4.8 Hz, 1H), 7.11 (d, J=3.6 Hz, 2H), 7.19-7.22 (m, 2H), 7.37 (dd, J=8.0, 2.1 Hz, 1H), 7.49 (d, J=3.6 Hz, 2H), 8.45 (dd, J=4.7, 1.7 Hz, 1H), 8.56 (d, J=2.2 Hz, 1H); MS (ESI$^+$) m/z 473.1 (M+H)$^+$.

Example 66

2-[1-(pyridin-4-yl)cyclopropyl]-N,N-bis{[1-(1,3-thiazol-2-yl)-1H-pyrrol-2-yl]methyl}ethanamine The titled compound was prepared as a trifluoroacetate salt according to the procedure described for the preparation of Example 8 using 2-(1-(pyridin-4-yl)cyclopropyl)ethanamine instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-d$_5$) δ ppm 0.64-0.70 (m, 2H), 0.71-0.76 (m, 2H), 1.67-1.76 (m, 2H), 2.60-2.72 (m, 2H), 4.09 (s, 4H), 6.25 (t, J=3.3 Hz, 2H), 6.27-6.30 (m, 2H), 6.97-7.01 (m, 2H), 7.16 (d, J=3.6 Hz, 2H), 7.26-7.28 (m, 2H), 7.50 (d, J=3.5 Hz, 2H), 8.49-8.57 (m, 2H); MS (ESI$^+$) m/z 487.1 (M+H)$^+$.

Example 67

4-[(bis{[1-(1,3-thiazol-2-yl)-1H-pyrrol-2-yl]methyl}amino)methyl]thiophene-2-carbonitrile The titled compound was prepared as a trifluoroacetate salt according to the procedure described for the preparation of Example 8 using 4-(aminomethyl)thiophene-2-carbonitrile instead of (2,4-dimethoxyphenyl)methanamine hydrochloride and 1-(thiazol-2-yl)-1H-pyrrole-2-carbaldehyde instead of 1-(1,3,4-thiadiazol-2-yl)-1H-pyrrole-2-carbaldehyde. $^1$H NMR (400 MHz, pyridine-d) δ ppm 3.59 (s, 2H), 4.04 (s, 4H), 6.25 (t, J=3.2 Hz, 2H), 6.25-6.30 (m, 2H), 7.17 (d, J=3.5 Hz, 3H), 7.20-7.23 (m, 2H), 7.24 (s, 1H), 7.50 (d, J=3.6 Hz, 2H); MS (ESI$^+$) m/z 463.0 (M+H)$^+$.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

What is claimed is:

1. A compound having formula (A), or a pharmaceutically acceptable salt thereof,

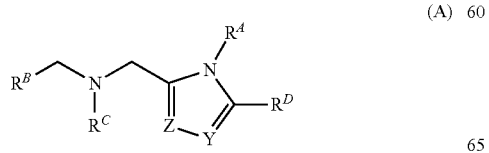
(A)

wherein,

R$^A$ is selected from the group consisting of 1,3-thiazol-2-yl and 1,3,4-thiadiazol-2-yl;

R$^B$ is selected from the group consisting of

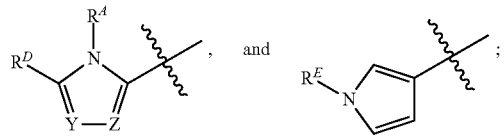

R$^C$ is selected from the group consisting of:
  branched-C$_4$-C$_8$alkyl, branched-C$_3$-C$_8$haloalkyl and —C(R$^{1a}$R$^{1b}$)—O—C$_1$-C$_6$alkyl, wherein R$^{1a}$ is hydrogen or C$_1$-C$_6$alkyl, and R$^{1b}$ is C$_1$-C$_6$alkyl;
  C$_5$-C$_7$cycloalkyl, wherein the C$_5$-C$_7$cycloalkyl is optionally substituted with 1 or 2 substituents selected from the group consisting of C$_1$-C$_6$alkyl, C$_1$-C$_6$haloalkyl and halogen;
  phenyl or 5- or 6-membered heteroaryl, wherein the phenyl or 5- or 6-membered heteroaryl are each independently optionally substituted with 1, 2 or 3 substituents selected from the group consisting of C$_1$-C$_4$alkyl, C$_1$-C$_4$alkoxy, haloC$_1$-C$_4$alkyl, haloC$_1$-C$_4$alkoxy, halogen and phenyl;
  monocyclic C$_5$-C$_7$cycloalkylC$_1$-C$_3$alkyl or bicyclic C$_6$-C$_{10}$cycloalkylC$_1$-C$_3$alkyl, wherein the monocyclic C$_5$-C$_7$cycloalkyl of monocyclic C$_5$-C$_7$cycloalkylC$_1$-C$_3$alkyl and the bicyclic C$_6$-C$_{10}$cycloalkyl of bicyclic C$_6$-C$_{10}$cycloalkylC$_1$-C$_3$alkyl are each independently optionally substituted with 1 or 2 substituents selected from the group consisting of C$_1$-C$_6$alkyl, C$_1$-C$_6$alkoxy, C$_1$-C$_6$haloalkyl, C$_1$-C$_6$haloalkoxy and halogen;

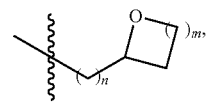

wherein the cyclic ether group is optionally substituted with 1, 2 or 3 substituents selected from the group consisting of C$_1$-C$_6$alkyl, C$_1$-C$_6$haloalkyl, C$_1$-C$_6$alkoxy, and halogen, and wherein m is 1, 2 or 3 and n is 1, 2 or 3;
  phenylC$_1$-C$_3$alkyl, wherein the phenyl of phenylC$_1$-C$_3$alkyl is optionally substituted with 1, 2 or 3 substituents selected from the group consisting of C$_1$-C$_3$alkyl, C$_1$-C$_6$haloalkyl, C$_1$-C$_6$alkoxy, haloC$_1$-C$_6$alkoxy, cyano and halogen;
  5- or 6-membered heteroarylC$_1$-C$_3$alkyl, wherein the 5- or 6-membered heteroaryl of 5- or 6-membered heteroarylC$_1$-C$_3$alkyl is optionally substituted with 1, 2 or 3 substituents selected from the group consisting of C$_1$-C$_6$alkyl, C$_1$-C$_6$haloalkyl, C$_1$-C$_6$alkoxy, cyano, halogen and phenyl, and wherein said phenyl is optionally substituted with 1, 2 or 3 substituents selected from the group consisting of C$_1$-C$_6$alkyl, C$_1$-C$_6$haloalkyl, C$_1$-C$_6$alkoxy, haloC$_1$-C$_6$alkoxy, cyano, and halogen; and

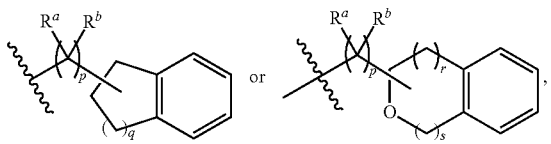

wherein
- $R^a$ and $R^b$ are at each occurrence independently selected from the group consisting of hydrogen and $C_1$-$C_6$alkyl, or
- $R^a$ and $R^b$ are taken together with the carbon atom to which they are attached to form a cyclopropyl, and wherein
- p is 0, 1 or 2;
- q is 1 or 2;
- r is 1 or 2; and
- s is 0 or 1;

$R^D$ is hydrogen or phenyl;
$R^E$ is phenyl optionally substituted with 1 or 2 substituents selected from the group consisting of $C_1$-$C_6$alkyl, $C_1$-$C_6$haloalkyl and halogen; and Y and Z are each independently selected from the group consisting of CH or N;
wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

2. The compound of claim 1, wherein
$R^D$ is hydrogen; and
each of Y and Z are CH.

3. A compound having formula (A), or a pharmaceutically acceptable salt thereof, (A)

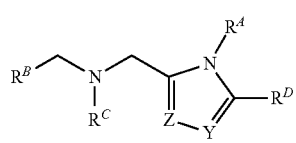

wherein,
$R^A$ is selected from the group consisting of $C_1$-$C_6$alkyl, $C_1$-$C_6$alkoxyalkyl, cyano$C_1$-$C_6$alkyl and $C_1$-$C_6$haloalkyl;
$R^B$ is selected from the group consisting of

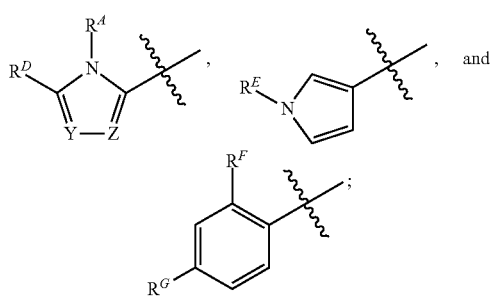

$R^C$ is selected from the group consisting of:
- branched-$C_4$-$C_8$alkyl, branched-$C_3$-$C_8$haloalkyl and —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl;
- $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen;
- phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl;
- monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

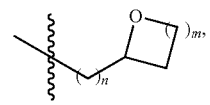

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3;
phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen;
5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and

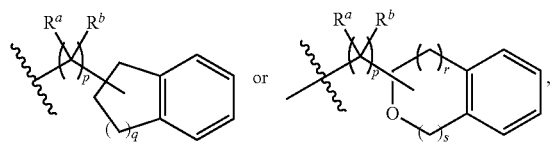

wherein
- $R^a$ and $R^b$ are at each occurrence independently selected from the group consisting of hydrogen and $C_1$-$C_6$alkyl, or
- $R^a$ and $R^b$ are taken together with the carbon atom to which they are attached to form a cyclopropyl, and wherein
- p is 0, 1 or 2;

q is 1 or 2;
r is 1 or 2; and
s is 0 or 1;
$R^D$ is phenyl;
$R^E$ is phenyl optionally substituted with 1 or 2 substituents selected from the group consisting of $C_1$-$C_6$alkyl, $C_1$-$C_6$haloalkyl and halogen;
$R^F$ is selected from the group consisting of $C_1$-$C_6$alkyl; $C_1$-$C_6$alkoxy; halo$C_1$-$C_6$alkyl; halo$C_1$-$C_6$alkoxy; and 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen;
$R^G$ is selected from the group consisting of hydrogen, $C_1$-$C_6$alkyl, $C_1$-$C_6$alkoxy, $C_1$-$C_6$haloalkyl, $C_1$-$C_6$haloalkoxy and halogen; and
each Y is CH; and
each Z is N;
wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

4. The compound of claim 1, wherein
$R^A$ is 1,3-thiazol-2-yl;
$R^D$ is hydrogen; and
each Y and each Z is CH.

5. The compound of claim 3, wherein
$R^F$ is selected from the group consisting of $C_1$-$C_6$alkyl, $C_1$-$C_6$alkoxy, halo$C_1$-$C_6$alkyl and halo$C_1$-$C_6$alkoxy; and
$R^G$ is hydrogen.

6. The compound of claim 3, wherein
$R^F$ is 5-membered or 6-membered heteroaryl optionally substituted with a substituent selected from the group consisting of $C_1$-$C_4$alkyl, $C_1$-$C_4$alkoxy, $C_1$-$C_4$haloalkyl, $C_1$-$C_4$haloalkoxy and halogen; and
$R^G$ is selected from the group consisting of $C_1$-$C_6$alkyl, $C_1$-$C_6$alkoxy, $C_1$-$C_6$haloalkyl, $C_1$-$C_6$haloalkoxy and halogen.

7. The compound of claim 1, wherein
$R^C$ is selected from the group consisting of branched-$C_4$-$C_8$alkyl, branched-$C_3$-$C_8$haloalkyl, and —C($R^{1a}R^{1b}$)—O—$C_1$-$C_6$alkyl, wherein
$R^{1a}$ is hydrogen or $C_1$-$C_6$alkyl, and
$R^{1b}$ is $C_1$-$C_6$alkyl.

8. The compound of claim 1, wherein
$R^C$ is $C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen.

9. The compound of claim 1, wherein
$R^C$ is selected from the group consisting of phenyl, 5- or 6-membered heteroaryl, wherein the phenyl or 5- or 6-membered heteroaryl is optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy and phenyl.

10. The compound of claim 1, wherein
$R^C$ is selected from the group consisting of monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl is optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen.

11. The compound of claim 10, wherein the $C_1$-$C_3$alkyl of monocyclic $C_5$-$C_7$cycloalkyl$C_1$-$C_3$alkyl or bicyclic $C_6$-$C_{10}$cycloalkyl$C_1$-$C_3$alkyl is substituted with a methyl or a cyclopropyl, wherein one atom of the cyclopropyl is an atom on the $C_1$-$C_3$alkyl chain.

12. The compound of claim 1, wherein
$R^C$ is

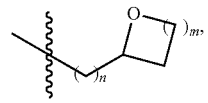

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy and halogen; wherein
m is 1, 2 or 3; and
n is 1, 2 or 3.

13. The compound of claim 1, wherein
$R^C$ is phenyl$C_1$-$C_3$alkyl wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen.

14. The compound of claim 13, wherein the $C_1$-$C_3$alkyl of phenyl$C_1$-$C_3$alkyl is substituted with a methyl or a cyclopropyl, wherein one atom of the cyclopropyl is an atom on the $C_1$-$C_3$alkyl chain.

15. The compound of claim 1, wherein
$R^C$ is selected from the group consisting of 5- or 6-membered heteroaryl$C_1$-$C_3$alkyl wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen.

16. The compound of claim 15, wherein the $C_1$-$C_3$alkyl of 5- or 6-membered heteroaryl$C_1$-$C_3$alkyl is substituted with a methyl or a cyclopropyl, wherein one atom of the cyclopropyl is an atom on the $C_1$-$C_3$alkyl chain.

17. The compound of claim 1, wherein $R^C$ is

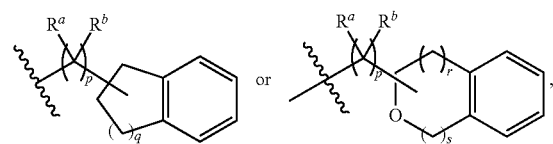

wherein
$R^a$ and $R^b$ are at each occurrence independently hydrogen or $C_1$-$C_6$alkyl, or
$R^a$ and $R^b$ are taken together with the carbon atom to which they are attached to form a cyclopropyl; and
wherein
p is 0, 1 or 2;
q is 1 or 2;
r is 1 or 2; and
s is 0 or 1.

18. The compound of claim 2, wherein $R^B$ is

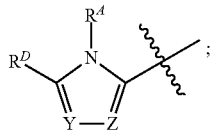

and $R^C$ is selected from the group consisting of:

branched-$C_4$-$C_8$alkyl, branched-$C_3$-$C_8$haloalkyl or —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl;

$C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen;

phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl;

monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen;

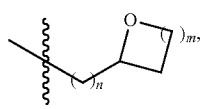

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3;

phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; and 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen;

wherein the $C_1$-$C_3$alkyl of monocyclic $C_5$-$C_7$cycloalkyl$C_1$-$C_3$alkyl, bicyclic $C_6$-$C_{10}$cycloalkyl$C_1$-$C_3$alkyl, phenyl$C_1$-$C_3$alkyl, or 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

19. The compound of claim 18, wherein $R^C$ is phenyl$C_1$-$C_3$alkyl, wherein the phenyl of phenyl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano and halogen; and wherein the $C_1$-$C_3$alkyl of phenyl$C_1$-$C_3$alkyl is optionally substituted with a methyl or a cyclopropyl, wherein one atom of the cyclopropyl is an atom on the $C_1$-$C_3$alkyl chain.

20. The compound of claim 19 having formula (II), or a pharmaceutically acceptable salt thereof,

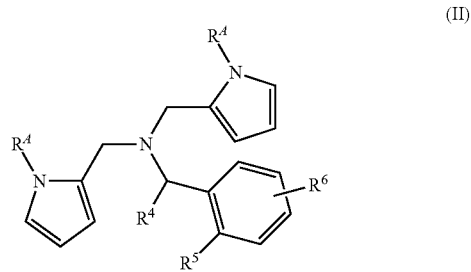

(II)

wherein, $R^4$ is hydrogen or methyl;

$R^5$ is selected from the group consisting of $C_1$-$C_6$alkyl, $C_1$-$C_6$haloalkyl, $C_1$-$C_6$alkoxy, halo$C_1$-$C_6$alkoxy, cyano and halogen; and $R^6$ is selected from the group consisting of hydrogen, $C_1$-$C_6$alkyl, $C_1$-$C_6$haloalkyl, $C_1$-$C_6$alkoxy, halo$C_1$-$C_6$alkoxy, and halogen.

21. The compound of claim 18, wherein $R^C$ is 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and wherein the $C_1$-$C_3$alkyl of the 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

22. The compound of claim 21 having formula (I), or a pharmaceutically acceptable salt thereof,

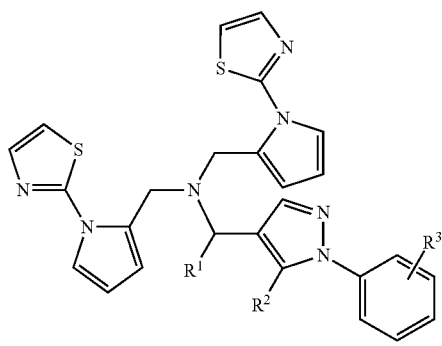

wherein,
R¹ is hydrogen or methyl;
R² is hydrogen or $C_1$-$C_6$-alkyl; and
R³ is hydrogen or halogen.

23. The compound of claim 21 having formula (III), or a pharmaceutically acceptable salt thereof,

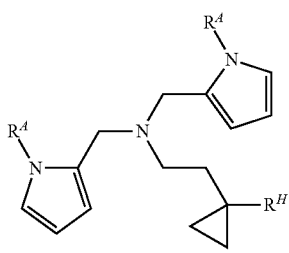

wherein, $R^H$ is 6-membered heteroaryl.

24. The compound of claim 18, wherein
$R^C$ is phenyl or 5- or 6-membered heteroaryl, wherein the phenyl or 5- or 6-membered heteroaryl are each independently optionally substituted with 1, 2 or 3 substituents selected from the group consisting of $C_1$-$C_4$alkyl, $C_1$-$C_4$alkoxy, halo$C_1$-$C_4$alkyl, halo$C_1$-$C_4$alkoxy, halogen and phenyl.

25. The compound of claim 24 having formula (IV), or a pharmaceutically acceptable salt thereof,

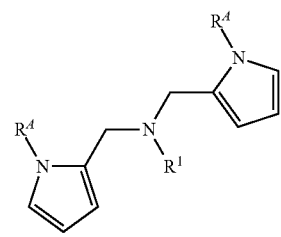

wherein, $R^I$ is 5-membered heteroaryl, wherein the 5-membered heteroaryl is optionally substituted with 1 or 2 substituents independently selected from the group consisting of $C_1$-$C_4$alkyl, $C_1$-$C_4$alkoxy, halo$C_1$-$C_4$alkyl, halo$C_1$-$C_4$alkoxy, halogen and phenyl.

26. The compound of claim 18, wherein
$R^C$ is selected from the group consisting of:
branched-$C_4$-$C_8$alkyl, branched-$C_3$-$C_8$haloalkyl or —C($R^{1a}R^{1b}$)—O—$C_1$-$C_6$alkyl, wherein $R^{1a}$ is hydrogen or $C_1$-$C_6$alkyl, and $R^{1b}$ is $C_1$-$C_6$alkyl;

$C_5$-$C_7$cycloalkyl, wherein the $C_5$-$C_7$cycloalkyl is optionally substituted with 1 or 2 substituents selected from the group consisting of $C_1$-$C_6$alkyl, $C_1$-$C_6$haloalkyl and halogen;
monocyclic $C_5$-$C_7$cycloalkyl$C_1$-$C_3$alkyl or bicyclic $C_6$-$C_{10}$cycloalkyl$C_1$-$C_3$alkyl, wherein the monocyclic $C_5$-$C_7$cycloalkyl of monocyclic $C_5$-$C_7$cycloalkyl$C_1$-$C_3$alkyl and the bicyclic $C_6$-$C_{10}$cycloalkyl of bicyclic $C_6$-$C_{10}$cycloalkyl$C_1$-$C_3$alkyl are each independently optionally substituted with 1 or 2 substituents selected from the group consisting of $C_1$-$C_6$alkyl, $C_1$-$C_6$alkoxy, $C_1$-$C_6$haloalkyl, $C_1$-$C_6$haloalkoxy and halogen; and

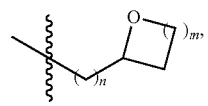

wherein the cyclic ether group is optionally substituted with 1, 2 or 3 substituents selected from the group consisting of $C_1$-$C_6$alkyl, $C_1$-$C_6$haloalkyl, $C_1$-$C_6$alkoxy, and halogen, and wherein m is 1, 2 or 3 and n is 1, 2 or 3.

27. The compound of claim 2, wherein
$R^B$ is

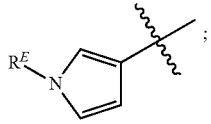

and
$R^C$ is 5- or 6-membered heteroaryl$C_1$-$C_3$alkyl, wherein the 5- or 6-membered heteroaryl of 5- or 6-membered heteroaryl$C_1$-$C_3$alkyl is optionally substituted with 1, 2 or 3 substituents selected from the group consisting of $C_1$-$C_6$alkyl, $C_1$-$C_6$haloalkyl, $C_1$-$C_6$alkoxy, cyano, halogen and phenyl, and wherein said phenyl is optionally substituted with 1, 2 or 3 substituents selected from the group consisting of $C_1$-$C_6$alkyl, $C_1$-$C_6$haloalkyl, $C_1$-$C_6$alkoxy, halo$C_1$-$C_6$alkoxy, cyano, and halogen; and
$R^E$ is phenyl optionally substituted with 1 or 2 substituents selected from the group consisting of $C_1$-$C_6$alkyl, $C_1$-$C_6$haloalkyl and halogen;
wherein the $C_1$-$C_3$alkyl of the 5- or 6-membered heteroaryl$C_1$-$C_3$alkyl is optionally substituted with a methyl or a cyclopropyl, wherein one atom of the cyclopropyl is an atom on the $C_1$-$C_3$alkyl chain.

28. The compound of claim 3, wherein
$R^B$ is

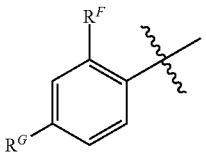

$R^C$ is 5- or 6-membered heteroaryl$C_1$-$C_3$alkyl, wherein the 5- or 6-membered heteroaryl of 5- or 6-membered heteroarylC$_1$-C$_3$alkyl is optionally substituted with 1, 2 or 3 substituents selected from the group consisting of C$_1$-C$_6$alkyl, C$_1$-C$_6$haloalkyl, C$_1$-C$_6$alkoxy, cyano, halogen and phenyl, and wherein said phenyl is optionally substituted with 1, 2 or 3 substituents selected from the group consisting of C$_1$-C$_6$alkyl, C$_1$-C$_6$haloalkyl, C$_1$-C$_6$alkoxy, haloC$_1$-C$_6$alkoxy, cyano, and halogen;

R$^F$ is selected from the group consisting of C$_1$-C$_6$alkyl; C$_1$-C$_6$alkoxy; haloC$_1$-C$_6$alkyl; haloC$_1$-C$_6$alkoxy; and 5-membered or 6-membered heteroaryl optionally substituted with a substituent selected from the group consisting of C$_1$-C$_4$alkyl, C$_1$-C$_4$alkoxy, C$_1$-C$_4$haloalkyl, C$_1$-C$_4$haloalkoxy and halogen; and R$^G$ is selected from the group consisting of hydrogen, C$_1$-C$_6$alkyl, C$_1$-C$_6$alkoxy, C$_1$-C$_6$haloalkyl, C$_1$-C$_6$haloalkoxy and halogen;

wherein the C$_1$-C$_3$alkyl of the 5- or 6-membered heteroarylC$_1$-C$_3$alkyl is optionally substituted with a methyl or a cyclopropyl, wherein one atom of the cyclopropyl is an atom on the C$_1$-C$_3$alkyl chain.

29. A compound having formula (V), or a pharmaceutically acceptable salt thereof,

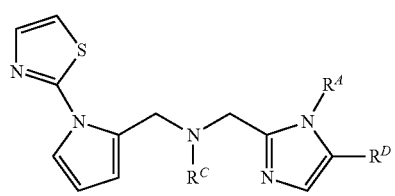

(V)

wherein,

R$^A$ is selected from the group consisting of C$_1$-C$_6$alkyl, C$_1$-C$_6$alkoxyalkyl, C$_1$-C$_6$alkyl, and C$_1$-C$_6$haloalkyl;

R$^C$ is 5- or 6-membered heteroarylC$_1$-C$_3$alkyl, wherein the 5- or 6-membered heteroaryl of 5- or 6-membered heteroarylC$_1$-C$_3$alkyl is optionally substituted with 1, 2 or 3 substituents selected from the group consisting of C$_1$-C$_6$alkyl, C$_1$-C$_6$haloalkyl, C$_1$-C$_6$alkoxy, cyano, halogen and phenyl, and wherein said phenyl is optionally substituted with 1, 2 or 3 substituents selected from the group consisting of C$_1$-C$_6$alkyl, C$_1$-C$_6$haloalkyl, C$_1$-C$_6$alkoxy, haloC$_1$-C$_6$alkoxy, cyano, and halogen; and R$^D$ is hydrogen or phenyl;

wherein the C$_1$-C$_3$alkyl of the 5- or 6-membered heteroarylC$_1$-C$_3$alkyl is optionally substituted with a methyl or a cyclopropyl, wherein one atom of the cyclopropyl is an atom on the C$_1$-C$_3$alkyl chain.

30. The compound of claim 3, wherein R$^B$ is

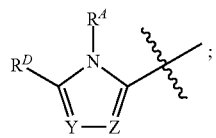

R$^C$ is 5- or 6-membered heteroarylC$_1$-C$_3$alkyl, wherein the 5- or 6-membered heteroaryl of 5- or 6-membered heteroarylC$_1$-C$_3$alkyl is optionally substituted with 1, 2 or 3 substituents selected from the group consisting of C$_1$-C$_6$alkyl, C$_1$-C$_6$haloalkyl, C$_1$-C$_6$alkoxy, cyano, halogen and phenyl, and wherein said phenyl is optionally substituted with 1, 2 or 3 substituents selected from the group consisting of C$_1$-C$_6$alkyl, C$_1$-C$_6$haloalkyl, C$_1$-C$_6$alkoxy, haloC$_1$-C$_6$alkoxy, cyano, and halogen;

wherein the C$_1$-C$_3$alkyl of the 5- or 6-membered heteroarylC$_1$-C$_3$alkyl is optionally substituted with a methyl or a cyclopropyl, wherein one atom of the cyclopropyl is an atom on the C$_1$-C$_3$alkyl chain.

31. A compound, wherein the compound is:
1-[1-(3-fluorophenyl)-5-methyl-1H-pyrazol-4-yl]-N,N-bis{[1-(1,3-thiazol-2-yl)-1H-pyrrol-2-yl]methyl}ethanamine;
(1S)-1-[1-(3-fluorophenyl)-5-methyl-1H-pyrazol-4-yl]-N,N-bis{[1-(1,3-thiazol-2-yl)-1H-pyrrol-2-yl]methyl}ethanamine;
(1R)-1-[1-(3-fluorophenyl)-5-methyl-1H-pyrazol-4-yl]-N,N-bis{[1-(1,3-thiazol-2-yl)-1H-pyrrol-2-yl]methyl}ethanamine;
1-[1-(3-fluorophenyl)-5-methyl-1H-pyrazol-4-yl]-N-(2-methoxybenzyl)-N-{[1-(1,3-thiazol-2-yl)-1H-pyrrol-2-yl]methyl}ethanamine;
N-{4-chloro-2-[2-(trifluoromethyl)pyrimidin-4-yl]benzyl}-1-[1-(3-fluorophenyl)-5-methyl-1H-pyrazol-4-yl]-N-{[1-(1,3-thiazol-2-yl)-1H-pyrrol-2-yl]methyl}ethanamine;
N-{[1-(2,6-dimethylphenyl)-1H-pyrrol-3-yl]methyl}-1-[1-(3-fluorophenyl)-5-methyl-1H-pyrazol-4-yl]-N-{[1-(1,3-thiazol-2-yl)-1H-pyrrol-2-yl]methyl}ethanamine;
1-[1-(3-fluorophenyl)-5-methyl-1H-pyrazol-4-yl]-N,N-bis[(1-methyl-5-phenyl-1H-imidazol-2-yl)methyl]ethanamine;
1-(2,4-dimethoxyphenyl)-N,N-bis{[1-(1,3,4-thiadiazol-2-yl)-1H-pyrrol-2-yl]methyl}methanamine;
1-methyl-N,N-bis{[1-(1,3,4-thiadiazol-2-yl)-1H-pyrrol-2-yl]methyl}-1H-pyrazol-5-amine;
1-phenyl-N,N-bis{[1-(1,3,4-thiadiazol-2-yl)-1H-pyrrol-2-yl]methyl}methanamine;
1-[(1R,4S)-bicyclo[2.2.1]hept-2-yl]-N,N-bis{[1-(1,3,4-thiadiazol-2-yl)-1H-pyrrol-2-yl]methyl}methanamine;
1-(2-methylphenyl)-N,N-bis{[1-(1,3,4-thiadiazol-2-yl)-1H-pyrrol-2-yl]methyl}methanamine;
(1R)-1-(4-fluorophenyl)-N,N-bis{[1-(1,3,4-thiadiazol-2-yl)-1H-pyrrol-2-yl]methyl}ethanamine;
1-(3,5-dichloropyridin-2-yl)-N, N-bis{[1-(1,3,4-thiadiazol-2-yl)-1H-pyrrol-2-yl]methyl}methanamine;
1-(2-fluorophenyl)-N,N-bis{[1-(1,3,4-thiadiazol-2-yl)-1H-pyrrol-2-yl]methyl}methanamine;
1-[1-(1,3,4-thiadiazol-2-yl)-1H-pyrrol-2-yl]-N-{[1-(1,3,4-thiadiazol-2-yl)-1H-pyrrol-2-yl]methyl}-N-[3-(trifluoromethyl)benzyl]methanamine;
1-(3,4-dichlorophenyl)-N,N-bis{[1-(1,3,4-thiadiazol-2-yl)-1H-pyrrol-2-yl]methyl}ethanamine;
1-(2-chlorophenyl)-N,N-bis{[1-(1,3,4-thiadiazol-2-yl)-1H-pyrrol-2-yl]methyl}methanamine;
(1R)-1-(2-chlorophenyl)-N, N-bis{[1-(1,3,4-thiadiazol-2-yl)-1H-pyrrol-2-yl]methyl}ethanamine;
(1S)-1-(2-chlorophenyl)-N,N-bis{[1-(1,3,4-thiadiazol-2-yl)-1H-pyrrol-2-yl]methyl}ethanamine;
2-[1-(pyridin-2-yl)cyclopropyl]-N,N-bis{[1-(1,3,4-thiadiazol-2-yl)-1H-pyrrol-2-yl]methyl}ethanamine;
N,N-bis{[1-(1,3,4-thiadiazol-2-yl)-1H-pyrrol-2-yl]methyl}aniline;
1-(4,4-difluorocyclohexyl)-N,N-bis{[1-(1,3,4-thiadiazol-2-yl)-1H-pyrrol-2-yl]methyl}methanamine;
2-[1-(pyridin-3-yl)cyclopropyl]-N,N-bis{[1-(1,3,4-thiadiazol-2-yl)-1H-pyrrol-2-yl]methyl}ethanamine;
N,N-bis{[1-(1,3,4-thiadiazol-2-yl)-1H-pyrrol-2-yl]methyl}-1-(thiophen-2-yl)propan-2-amine;
1-[1-(pyridin-3-yl)cyclopropyl]-N,N-bis{[1-(1,3,4-thiadiazol-2-yl)-1H-pyrrol-2-yl]methyl}methanamine;

2-[1-(pyridin-4-yl)cyclopropyl]-N,N-bis{[1-(1,3,4-thiadiazol-2-yl)-1H-pyrrol-2-yl]methyl}ethanamine;
4-[(bis{[1-(1,3,4-thiadiazol-2-yl)-1H-pyrrol-2-yl]methyl}amino)methyl]thiophene-2-carbonitrile;
1-(2,4-dichlorophenyl)-N,N-bis{[1-(1,3-thiazol-2-yl)-1H-pyrrol-2-yl]methyl}methanamine;
1-(2,4-dimethoxyphenyl)-N,N-bis{[1-(1,3-thiazol-2-yl)-1H-pyrrol-2-yl]methyl}methanamine;
1-phenyl-N,N-bis{[1-(1,3-thiazol-2-yl)-1H-pyrrol-2-yl]methyl}methanamine;
1-[(1R,4S)-bicyclo[2.2.1]hept-2-yl]-N, N-bis{[1-(1,3-thiazol-2-yl)-1H-pyrrol-2-yl]methyl}methanamine;
1-(tetrahydrofuran-2-yl)-N, N-bis{[1-(1,3-thiazol-2-yl)-1H-pyrrol-2-yl]methyl}methanamine;
1-[1-(1,3-thiazol-2-yl)-1H-pyrrol-2-yl]-N-{[1-(1,3-thiazol-2-yl)-1H-pyrrol-2-yl]methyl}-N-[4-(trifluoromethyl)benzyl]methanamine;
3-methyl-1-phenyl-N,N-bis{[1-(1,3-thiazol-2-yl)-1H-pyrrol-2-yl]methyl}-1H-pyrazol-5-amine;
1-(2,6-dichlorophenyl)-N,N-bis{[1-(1,3-thiazol-2-yl)-1H-pyrrol-2-yl]methyl}methanamine;
1-(2-methylphenyl)-N,N-bis{[1-(1,3-thiazol-2-yl)-1H-pyrrol-2-yl]methyl}methanamine;
1-(3,5-dichloropyridin-2-yl)-N, N-bis{[1-(1,3-thiazol-2-yl)-1H-pyrrol-2-yl]methyl}methanamine;
2-methyl-N,N-bis{[1-(1,3-thiazol-2-yl)-1H-pyrrol-2-yl]methyl}propan-1-amine;
1-(2-fluorophenyl)-N,N-bis{[1-(1,3-thiazol-2-yl)-1H-pyrrol-2-yl]methyl}methanamine;
1-[1-(3-fluorophenyl)-5-methyl-1H-pyrazol-4-yl]-N-[(1-methyl-5-phenyl-1H-imidazol-2-yl)methyl]-N-{[1-(1,3-thiazol-2-yl)-1H-pyrrol-2-yl]methyl}ethanamine;
1-(2,4-dichlorophenyl)-N,N-bis{[1-(1,3,4-thiadiazol-2-yl)-1H-pyrrol-2-yl]methyl}methanamine;
1-(4-fluorophenyl)-3-methyl-N,N-bis{[1-(1,3,4-thiadiazol-2-yl)-1H-pyrrol-2-yl]methyl}-1H-pyrazol-5-amine;
1-[1-(1,3-thiazol-2-yl)-1H-pyrrol-2-yl]-N-{[1-(1,3-thiazol-2-yl)-1H-pyrrol-2-yl]methyl}-N-[3-(trifluoromethyl)benzyl]methanamine;
4-[(bis{[1-(1,3-thiazol-2-yl)-1H-pyrrol-2-yl]methyl}amino)methyl]benzonitrile;
1-(3,4-dichlorophenyl)-N,N-bis{[1-(1,3-thiazol-2-yl)-1H-pyrrol-2-yl]methyl}ethanamine;
1-(2-chlorophenyl)-N,N-bis{[1-(1,3-thiazol-2-yl)-1H-pyrrol-2-yl]methyl}methanamine;
(1R)-1-(2-chlorophenyl)-N, N-bis{[1-(1,3-thiazol-2-yl)-1H-pyrrol-2-yl]methyl}ethanamine;
(1S)-1-(2-chlorophenyl)-N,N-bis{[1-(1,3-thiazol-2-yl)-1H-pyrrol-2-yl]methyl}ethanamine;
N,N-bis{[1-(1,3-thiazol-2-yl)-1H-pyrrol-2-yl]methyl}pyridazin-3-amine;
2-[1-(pyridin-2-yl)cyclopropyl]-N,N-bis{[1-(1,3-thiazol-2-yl)-1H-pyrrol-2-yl]methyl}ethanamine;
N,N-bis{[1-(1,3-thiazol-2-yl)-1H-pyrrol-2-yl]methyl}cyclohexanamine;
N,N-bis{[1-(1,3-thiazol-2-yl)-1H-pyrrol-2-yl]methyl}aniline;
1-[1-(1,3,4-thiadiazol-2-yl)-1H-pyrrol-2-yl]-N-{[1-(1,3,4-thiadiazol-2-yl)-1H-pyrrol-2-yl]methyl}-N-[4-(trifluoromethyl)benzyl]methanamine;
1-(2,6-dichlorophenyl)-N,N-bis{[1-(1,3,4-thiadiazol-2-yl)-1H-pyrrol-2-yl]methyl}methanamine;
4-[(bis{[1-(1,3,4-thiadiazol-2-yl)-1H-pyrrol-2-yl]methyl}amino)methyl]benzonitrile;
1-(4,4-difluorocyclohexyl)-N,N-bis{[1-(1,3-thiazol-2-yl)-1H-pyrrol-2-yl]methyl}methanamine;
1-[1-(1,3-thiazol-2-yl)-1H-pyrrol-2-yl]-N-{[1-(1,3-thiazol-2-yl)-1H-pyrrol-2-yl]methyl}-N-{[1-(2,2,2-trifluoroethyl)-1H-pyrazol-4-yl]methyl}methanamine;
1-[1-(difluoromethyl)-1H-imidazol-2-yl]-N,N-bis{[1-(1,3-thiazol-2-yl)-1H-pyrrol-2-yl]methyl}methanamine;
2-[1-(pyridin-3-yl)cyclopropyl]-N,N-bis{[1-(1,3-thiazol-2-yl)-1H-pyrrol-2-yl]methyl}ethanamine;
1-[(3R)-tetrahydrofuran-3-yl]-N,N-bis{[1-(1,3,4-thiadiazol-2-yl)-1H-pyrrol-2-yl]methyl}methanamine;
(1R)-1-(4-fluorophenyl)-N,N-bis{[1-(1,3-thiazol-2-yl)-1H-pyrrol-2-yl]methyl}ethanamine;
1-(furan-2-yl)-N,N-bis{[1-(1,3-thiazol-2-yl)-1H-pyrrol-2-yl]methyl}methanamine;
N,N-bis{[1-(1,3-thiazol-2-yl)-1H-pyrrol-2-yl]methyl}-1-(thiophen-2-yl)propan-2-amine;
1-[1-(pyridin-3-yl)cyclopropyl]-N,N-bis{[1-(1,3-thiazol-2-yl)-1H-pyrrol-2-yl]methyl}methanamine;
2-[1-(pyridin-4-yl)cyclopropyl]-N,N-bis{[1-(1,3-thiazol-2-yl)-1H-pyrrol-2-yl]methyl}ethanamine; and
4-[(bis{[1-(1,3-thiazol-2-yl)-1H-pyrrol-2-yl]methyl}amino)methyl]thiophene-2-carbonitrile.

32. A pharmaceutical composition comprising one or more compounds of claim 1 or pharmaceutically acceptable salts thereof; one or more excipients; and optionally one or more additional therapeutic agents.

33. A method of preventing and/or treating RSV infection, comprising administering a therapeutically effective amount of one or more compounds of claim 1 or pharmaceutically acceptable salts thereof, optionally in combination with one or more additional therapeutic agents to a subject in need thereof.

34. The method of claim 33, wherein the RSV infection is from an RSV virus of group A or B.

35. The method of claim 34, wherein the RSV infection is from a mutant of an RSV virus.

36. A method for inhibiting replication of a ribonucleic acid (RNA) virus, comprising exposing the virus to one or more compounds of claim 1 or pharmaceutically acceptable salts thereof, optionally in combination with one or more additional therapeutic agents.

37. A method for preparing a compound of claim 1, or a pharmaceutically acceptable salt thereof, comprising:
reacting an amine of formula (2-1) with an aldehyde of formula (2-2) in the presence of a reductant and an acid to give a compound of formula (3-1)

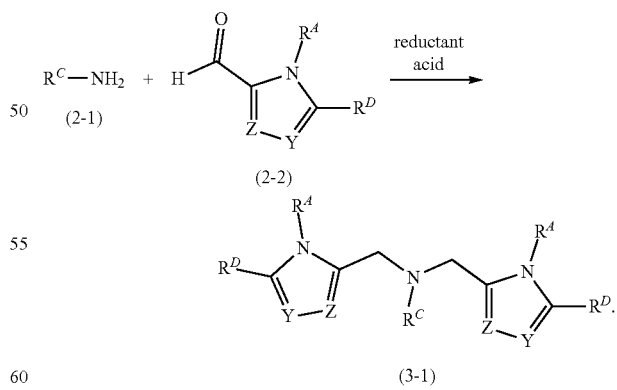

* * * * *